US012315637B2

(12) United States Patent
Groteke et al.

(10) Patent No.: US 12,315,637 B2
(45) Date of Patent: May 27, 2025

(54) INTEGRATED, AI-ENABLED VALUE-BASED CARE MEASUREMENT AND OBJECTIVE RISK ASSESSMENT CLINICAL AND FINANCIAL MANAGEMENT SYSTEM

(71) Applicant: My Medical HUB Corporation, Safety Harbor, FL (US)

(72) Inventors: Walter M Groteke, Safety Harbor, FL (US); Eric K Groteke, Safety Harbor, FL (US); Barry Fitch, Augusta, SC (US); Md. Al Mehedi Hasan, Rajshahi (BD); Rifaet Ullah, Rangpur (BD)

( * ) Notice: Subject to any disclaimer, the term of this patent is extended or adjusted under 35 U.S.C. 154(b) by 0 days.

(21) Appl. No.: 18/794,726

(22) Filed: Aug. 5, 2024

(65) Prior Publication Data

US 2024/0395410 A1 Nov. 28, 2024

Related U.S. Application Data

(63) Continuation-in-part of application No. 17/806,874, filed on Jun. 14, 2022, now Pat. No. 12,057,212, which is a continuation-in-part of application No. 16/913,236, filed on Jun. 26, 2020, now abandoned.

(60) Provisional application No. 63/582,544, filed on Sep. 14, 2023, provisional application No. 63/210,623, filed on Jun. 15, 2021, provisional application No. 62/866,786, filed on Jun. 26, 2019.

(51) Int. Cl.
*G16H 50/20* (2018.01)

(52) U.S. Cl.
CPC .................................. *G16H 50/20* (2018.01)

(58) Field of Classification Search
CPC ........ G16H 50/30; G16H 50/20; G16H 20/30; G16H 15/00; G16H 20/40
See application file for complete search history.

(56) References Cited

U.S. PATENT DOCUMENTS

| 2006/0015546 | A1 | 1/2006 | Sawadsky et al. |
|---|---|---|---|
| 2008/0147440 | A1 | 6/2008 | Kil |
| 2011/0166883 | A1 | 7/2011 | Palmer |

(Continued)

OTHER PUBLICATIONS

Albuquerque et al., "Remote Gait Type Classification System Using Markerless 2D Video.", Diagnostics 2021, Oct. 2, 2021.

(Continued)

*Primary Examiner* — Joseph D Burgess
(74) *Attorney, Agent, or Firm* — CIONCA IP Law P.C.

(57) ABSTRACT

A computer system for automatically performing medical diagnoses having a main portal configured to allow data communication with a user device, an AI bot in data communication with the main portal, the AI bot being configured to guide the user through a medical assessment, perform the medical assessment and diagnose the patient, wherein the AI bot is further configured to receive video data of the patient performing a physical activity, analyze each individual frame of the video using a custom trained model in order to diagnose the patient, a patient portal in data communication with a processing and communication module and the AI bot, a central database in data communication with the processing and communication module, an internal database, the AI bot and the patient portal, the central database being configured to facilitate an interconnection of the AI bot with the internal database and an external database.

5 Claims, 61 Drawing Sheets

(56) References Cited

U.S. PATENT DOCUMENTS

| | | | |
|---|---|---|---|
| 2014/0228712 A1* | 8/2014 | Elliott | G16H 20/30 |
| | | | 600/587 |
| 2020/0237291 A1 | 7/2020 | Sundaram | |
| 2020/0335222 A1 | 10/2020 | Winterbach | |
| 2021/0232361 A1 | 7/2021 | Brown et al. | |
| 2021/0386359 A1 | 12/2021 | Adeli-Mosabbeb et al. | |
| 2023/0402180 A1* | 12/2023 | Molero Leon | G06N 3/08 |

OTHER PUBLICATIONS

Cheng et al., "HigherHRNet: Scale-Aware Representation Learning for Bottom-Up Human Pose Estimation.", arXiv, Mar. 2, 2020.
Patent Cooperation Treaty, International Search Report, Jun. 28, 2023.

\* cited by examiner

| | Position 1 (Beginning) | Time in Video | Position 2 (Ending) | Time in Video | Duration (sec) |
|---|---|---|---|---|---|
| Stance Phase | Right Heel Strike | 1.50 | Right Toe Off | 2.16 | 0.66 |
| Swing Phase | Right Toe Off | 2.16 | Right Heel Strike | 2.60 | 0.44 |
| Stride | Right Toe Off | 2.16 | Right Toe Off | 3.26 | 1.1 |

| Image No. | Outcomes | Calculation |
|---|---|---|
| 6(a) | (R)HIP Flexion | 180 – 163 = 17 |
| | (R)KNEE Flexion | 180 – 175 = 5 |
| | (R)ANKLE Dorsiflexion | 90 – 80 = 10 |
| 6(b) | (R)HIP Extension | None (Since, 159 < 180) |
| | (R)KNEE Extension | None (Since, 175 < 180) |
| | (R)ANKLE Plantarflexion | 95 – 90 = 5 |

| MODEL | Hip Flexion | Hip Extension | Knee Flexion | Knee Extension | Ankle Dorsiflexion | Ankle Plantarflexion |
|---|---|---|---|---|---|---|
| G001HS | 27 | None | None | 8 | 19 | None |
| G002HS | 21 | None | 9 | None | 9 | None |
| G003HS | 17 | None | 9 | None | 4 | None |
| G004HS | 28 | None | 3 | None | 0(Neutral) | 0(Neutral) |
| G005HS | 5 | none | 3 | None | None | 5 |
| G006HS | 6 | None | None | 9 | 8 | None |
| G007HS | 7 | None | 5 | None | 10 | None |
| G008HS | 25 | None | 26 | None | 3 | None |
| G009HS | 6 | None | 14 | None | 9 | None |
| G010HS | 15 | None | 4 | None | 12 | None |
| G011HS | 19 | None | 13 | None | 8 | None |
| G012HS | 31 | None | 11 | None | 12 | None |
| G013HS | 31 | None | 2 | None | None | 2 |
| G014HS | 24 | None | 11 | None | None | 2 |
| G015HS | 21 | None | 5 | None | None | 5 |
| G016HS | 13 | None | None | 6 | 12 | None |
| G017HS | 12 | None | 4 | None | 12 | None |
| G018HS | 31 | None | 20 | None | None | 2 |
| G019HS | 42 | None | 30 | None | 21 | None |
| G020HS | 26 | None | 14 | None | 15 | None |

FIG. 6D

| PHASE | HIP | KNEE | ANKLE |
|---|---|---|---|
| HEEL STRIKE | 5 FLEX – 42 FLEX | 30 FLEX – 9 EXT | 21 DF – 5 PF |

FIG. 6E

Figure 7: Midstance Frame with annotated angles

| Image No. | Outcomes | Calculation |
|---|---|---|
| 7(a) | (R)HIP Flexion | 180 − 179 = 1 |
| | (R)KNEE Flexion | 180 − 168 = 12 |
| | (R)ANKLE Dorsiflexion | 90 − 82 = 8 |
| 7(b) | (R)HIP Extension | 192 − 180 = 12 |
| | (R)KNEE Extension | None (Since, 177 < 180) |
| | (R)ANKLE Plantarflexion | 93 − 90 = 3 |

| Model | Hip Flexion | Hip Extension | Knee Flexion | Knee Extension | Ankle Dorsiflexion | Ankle Plantarflexion |
|---|---|---|---|---|---|---|
| G001MS | 0(Neutral) | 0(Neutral) | 0(Neutral) | 0(Neutral) | 2 | None |
| G002MS | 0(Neutral) | 0(Neutral) | 10 | None | 0(Neutral) | 0(Neutral) |
| G003MS | 14 | None | 24 | None | 6 | None |
| G004MS | 1 | None | 18 | None | 4 | None |
| G005MS | 9 | None | 16 | None | None | 1 |
| G006MS | 12 | None | 8 | None | None | 4 |
| G007MS | 1 | None | 12 | None | 8 | None |
| G008MS | 0(Neutral) | 0(Neutral) | 5 | None | 13 | None |
| G009MS | 6 | None | 20 | None | 10 | None |
| G010MS | None | 1 | 6 | None | 10 | None |
| G011MS | 6 | None | 21 | None | 10 | None |
| G012MS | 12 | None | 25 | None | 9 | None |
| G013MS | 19 | None | 14 | None | 3 | None |
| G014MS | None | 3 | 14 | None | 4 | None |
| G015MS | None | 12 | None | 3 | None | 3 |
| G016MS | 11 | None | 13 | None | 12 | None |
| G017MS | None | 7 | 12 | None | 9 | None |
| G018MS | 8 | None | 15 | None | 7 | None |
| G019MS | 2 | None | 6 | None | 7 | None |
| G020MS | 15 | None | 22 | None | 16 | None |

FIG. 7D

| Phase | Hip | Knee | Ankle |
|---|---|---|---|
| MIDSTANCE | 19FLEX – 12 EXT | 25FLEX – 3 EXT | 16 DF – 4 PF |

FIG. 7E

| PHASE | HIP | KNEE | ANKLE |
|---|---|---|---|
| HEEL STRIKE | 5 FLEX – 42 FLEX | 30 FLEX – 9 EXT | 21 DF – 5 PF |
| MIDSTANCE | 19 FLEX – 12 EXT | 25 FLEX – 3 EXT | 16 DF – 4 PF |
| TOE-OFF | 17 FLEX – 35 EXT | 16 FLEX – 62 FLEX | 20 DF – 21 PF |
| MID SWING | 41 FLEX – 2 EXT | 24 FLEX – 86 FLEX | 15 DF – 9 PF |
FIG. 8
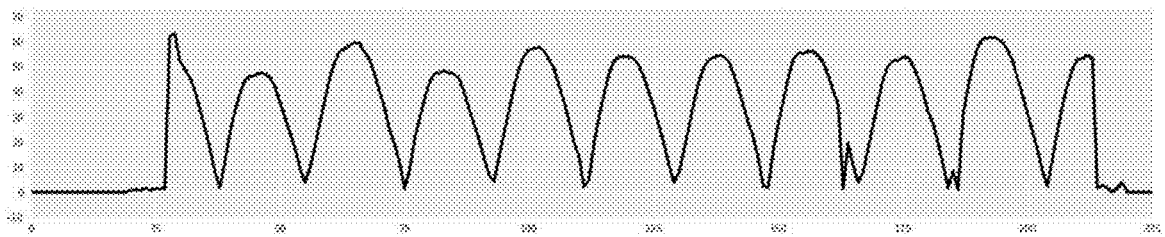
FIG. 9A
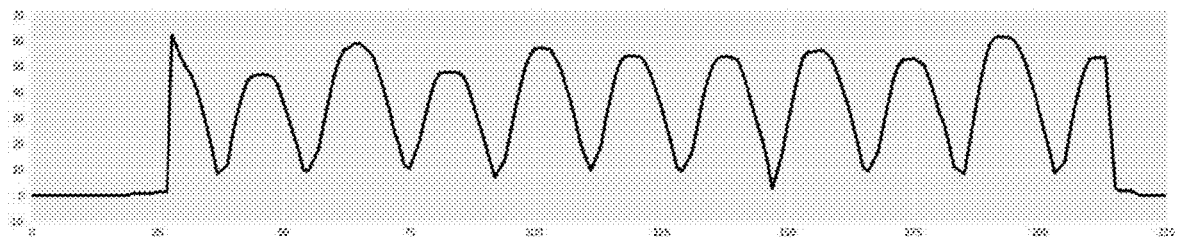
FIG. 9B
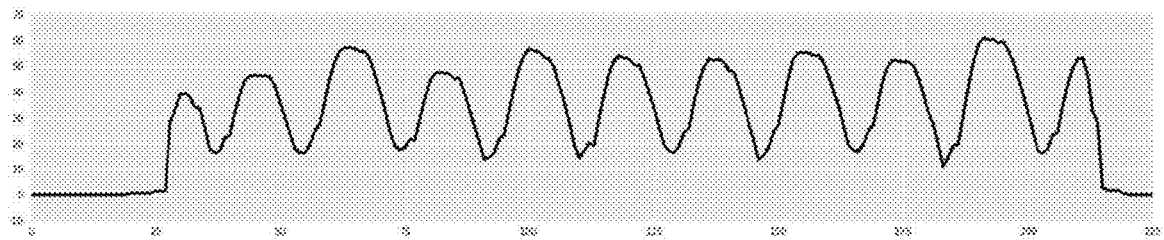
FIG. 9C

|  | Actual | | | Predicted by API | | |
|---|---|---|---|---|---|---|
|  | Average Stride Time (sec) | Average Stance Phase Duration (%) | Average Swing Phase Duration (%) | Average Stride Time (sec) | Average Stance Phase | Average Swing Phase Duration (%) |
| G018 | 1.26 | 65.87% | 34.13% | 1.27 | 66.14% | 33.86% |
| G019 | 1.17 | 63.52% | 36.48% | 1.12 | 66.96% | 33.03% |
| G020 | 1.14 | 63.44% | 36.56% | 1.15 | 67.83% | 33.17% |

FIG. 18

|  | Actual | | | Predicted | | |
|---|---|---|---|---|---|---|
| Test ID | Average Stance Percentage (%) | Average Swing Percentage (%) | Gait Classification | Average Stance Percentage (%) | Average Swing Percentage (%) | Gait Classification |
| IN-TEST-1615199380115 | 67.85% | 32.15% | Normal | 69.69% | 39.31% | Normal |
| IN-TEST-1614773282472 | 64.29% | 35.71% | Normal | 63.18% | 36.72% | Normal |
| IN-TEST-1617791661532 | 66.67% | 33.33% | Normal | 0.0% | 0.0% | Abnormal |
| IN-TEST-16125437096 36 | 61.95% | 38.05% | Normal | 67.16% | 32.84% | Normal |
| IN-TEST-161 24510341 96 | 65.52% | 34.48% | Normal | 50.0% | 50.0% | Abnormal |
| IN-TEST-16124511 21998 | 61.01% | 38.99% | Abnormal | 50.0% | 50.0% | Abnormal |
| IN-TEST-16124511 21999 | 57.43% | 42.57% | Abnormal | 50.0% | 50.0% | Abnormal |

FIG. 19

|  | Actual | | | Predicted | | |
| --- | --- | --- | --- | --- | --- | --- |
| Test Id | Average Stance Percentage | Average Swing Percentage | Gait Classification | Average Stance Percentage | Average Swing Percentage | Gait Classification |
| 000 | 70.15% | 29.85% | Normal | 65.13% | 34.87% | Normal |
| 001 | 70.10% | 29.90% | Normal | 62.45% | 37.54% | Normal |
| 002 | 70.96% | 29.04% | Normal | 63.79% | 36.20% | Normal |
| 003 | 70.33% | 29.66% | Normal | 78.36% | 21.64% | Normal |
| 004 | 68.19% | 31.80% | Normal | 62.95% | 37.04% | Normal |
| 005 | 71.14% | 28.85% | Normal | 66.39% | 33.61% | Normal |
| 006 | 67.13% | 32.86% | Normal | 54.17% | 45.82% | Normal |
| 008 | 69.74% | 30.26% | Normal | 61.09% | 38.90% | Normal |
| 010 | 66.67% | 33.34% | Normal | 57.23% | 42.76% | Normal |
| 012 | 69.97% | 30.02% | Normal | 69.88% | 30.12% | Normal |
| 013 | 67.37% | 32.63% | Normal | 83.46% | 16.53% | Normal |
| 014 | 66.76% | 33.23% | Normal | 62.24% | 37.75% | Normal |
| 016 | 72.28% | 27.71% | Normal | 67.04% | 32.96% | Normal |
| 017 | 74.12% | 25.89% | Normal | 57.47% | 42.53% | Normal |
| 018 | 67.14% | 32.85% | Normal | 57.97% | 42.02% | Normal |
| 020 | 66.48% | 33.52% | Normal | 54.97% | 45.02% | Normal |
| 022 | 72.05% | 27.94% | Normal | 64.78% | 35.22% | Normal |
| 024 | 66.67% | 33.33% | Normal | 58.09% | 41.91% | Normal |
| 026 | 67.20% | 32.80% | Normal | 64.21% | 35.78% | Normal |
| 027 | 73.33% | 26.67% | Normal | 66.67% | 33.34% | Normal |
| 028 | 69.24% | 30.75% | Normal | 58.57% | 41.43% | Normal |

FIG. 20

| Posture | Normal High / Low | Current Deviation | | |
|---|---|---|---|---|
| | | L-Deviation | Deviation | R-Deviation |
| Right deviation from midline | * | 6.97 | | 6.12 |
| Knee | | | 0.425 | |
| Hip | | | 1.10 | |
| Shoulder | | | 0.425 | |
| Nose | | | 0.18 | |

FIG. 22

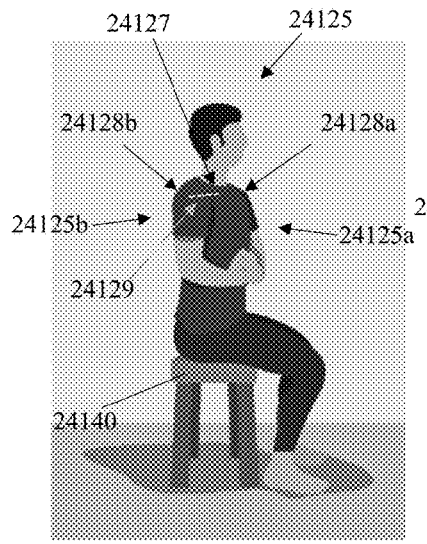
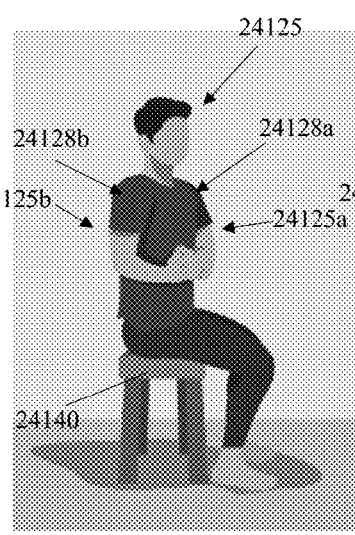
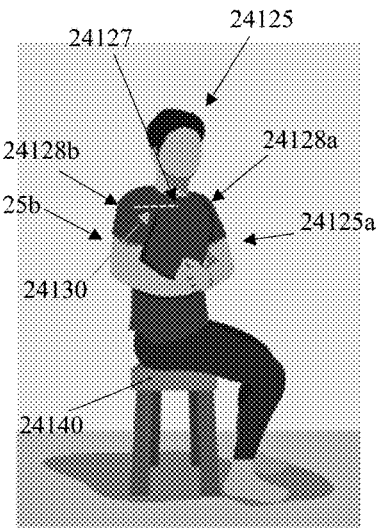
FIG.24A   FIG.24B   FIG.24C
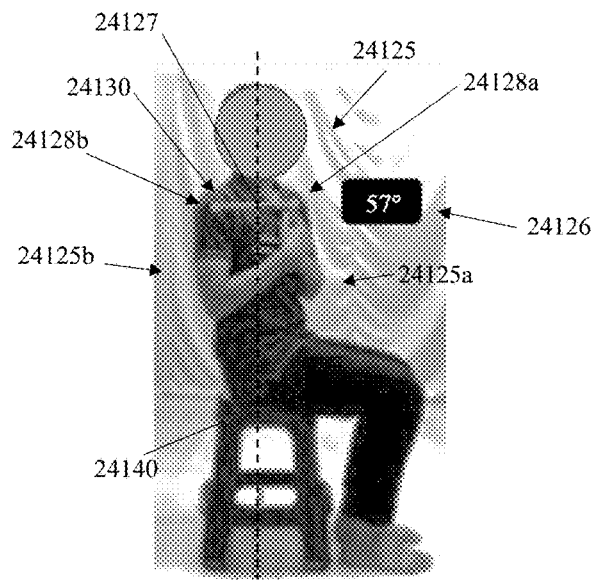
FIG.24D

INTEGRATED, AI-ENABLED VALUE-BASED CARE MEASUREMENT AND OBJECTIVE RISK ASSESSMENT CLINICAL AND FINANCIAL MANAGEMENT SYSTEM

CROSS-REFERENCE TO RELATED APPLICATIONS

This application claims the benefit of U.S. Provisional application No. 63/582,544, filed Sep. 14, 2023, and is a continuation-in-part and claims the benefit of U.S. Non-Provisional application Ser. No. 17/806,874 filed Jun. 14, 2022, which claims the benefit of U.S. Non-Provisional application Ser. No. 16/913,236, filed Jun. 26, 2020, which claims the benefit of U.S. Provisional Application No. 62/866,786, filed Jun. 26, 2019, and claims the benefit of U.S. Provisional Application No. 63/210,623, filed Jun. 15, 2021, all of which are hereby incorporated by reference, to the extent that they are not conflicting with the present application.

BACKGROUND OF INVENTION

1. Field of the Invention

The invention relates generally to platforms configured for medical data collection, analysis, and reporting and specifically to virtual platforms configured for medical data collection, analysis and reporting using AI-driven machine learning technologies.

2. Description of the Related Art

Clinical and sub-clinical process decisions have historically relied on the symptom(s) generators and diagnosing causality much in alignment with the practice of the medical diagnosis arts. In an ever-evolving clinical environment, judgment and experientially developed predictive models are used by the healthcare end-users to utilize the information currently at hand to offer guidance to patients and make course of treatment decisions unilaterally with little evidence of causal relation to the direct and indirect risk factors that may predispose an individual or animal to a catastrophic health event or claim. This problem is compounded by the presence of risk factors that are asymptomatic or "hidden" to the individual or animal and their identification may vary from one healthcare provider to another. Employers, payers, governments and health care systems are bearing the brunt of ever-increasing healthcare expenditures of their employees with little access to the direct and indirect risk factor data and how they can leverage it to improve employee's health and productivity while saving money and improving efficiencies. Employers are "shielded" by payers due to sensitive employee healthcare data and are therefore prohibited from being involved in the healthcare decisions of their workforce.

Additionally, within the United States and other developed countries around the world, vulnerable populations are unable to access care for a variety of reasons including, but not limited to, the absence of providers, insufficient financial resources, and a wide variety of socioeconomic factors. These problems place tremendous strain on the healthcare delivery and financing systems due to undiagnosed, untreated conditions that continue to deteriorate over time. The human, psychological, and financial toll on individuals, their families, and surrounding communities is immeasurable. To further complicate matters, the US and other developed nations support fragmented, siloed healthcare delivery systems. Individual patient data resides within a variety of systems and entities, which often works against the most efficient, cost-effective form of care. Physicians and providers in the United States are often obligated or incentivized to direct diagnostic, ancillary, and acute care to high-cost facilities and services within their region. Patients have little recourse to challenge these decisions, resulting in over inflated costs for payors, self-funded employers, and individuals.

Therefore, there is a need to solve the problems described above by proving a device and method for generating actionable health reports by gathering and interpreting all available medical information on a patient, without the immediate and direct need for physician or other medical personnel.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, an automated method of diagnosing a patient, operable on a computer system having a central database and an internal database, and a device comprising a processor, a user interface, and a camera, is provided, the method comprising: providing a patient portal for the patient to interface with the central database through the device; allowing the patient to perform a type of medical assessment from the patient portal; providing instructions for the patient to perform a corresponding physical activity for the type of medical assessment selected; receiving in the central database a video of the patient performing the corresponding physical activity captured by the camera; separating the video into individual frames; analyzing each individual frame of the video using a custom trained model to identify coordinates of key points for the type of medical assessment selected; diagnosing and/or suggesting possible care classifications and health conditions based on the coordinates of the key points; and/or reporting the possible care classification health conditions to the patient. Thus, an advantage is that this automated method provides an AI-determined diagnosis faster and more affordably than in person medical practices, while allowing for patients to report symptoms to assess preliminary health issues. Another advantage is that a standardized, automated method of diagnosing a patient may provide a risk value for quickly assessing a patient's risk of experiencing musculoskeletal injury for specific body regions or conditions, thus providing patients, providers and other concerned parties with a readily understood measure of patient health. Another advantage is that the automated method of diagnosing a patient may utilize standardized, machine learning algorithms and its database of patient data to diagnose patients based on previously undetected, asymptomatic risk factors.

In another aspect, an automated method of diagnosing a patient, operable on a computer system having a central database and an internal database, and a device comprising a processor, a user interface, and a camera, is provided, the method comprising: providing a patient portal for the patient to interface with the central database through the device; allowing the patient to perform a gait assessment from the patient portal; providing instructions for the patient to perform a gait procedure; receiving in the central database a video of the patient performing the gait procedure captured by the camera; separating the video into individual frames; analyzing each individual frame of the video using a custom trained model to identify coordinates of key points for the type of medical assessment selected; and diagnosing gait normality based on the coordinates of the key points. Again, an advantage is that this automated method provides a standardized, AI-determined diagnosis faster and more affordably than in person medical practices, while allowing for patients to report symptoms to assess preliminary health issues. Another advantage is that an automated method of diagnosing a patient may provide a risk value for quickly assessing a patient's risk of experiencing musculoskeletal injury for specific body regions or conditions, thus providing patients, providers and other concerned parties with a readily understood measure of patient health. Another advantage is that the automated method of diagnosing a patient may utilize standardized, machine learning algorithms and its database of patient data to diagnose patients based on previously undetected, asymptomatic risk factors.

In an aspect, a computer system for automatically performing medical diagnoses is provided, the computer system comprising: a main portal configured to allow data communication with a user device, thus allowing a user to access the computer system; an Artificial Intelligence (AI) bot in data communication with the main portal, the AI bot being configured to guide the user through a medical assessment including a series of intake questions and machine-learned biomechanical movements, perform the medical assessment and diagnose a patient, wherein the AI bot is further configured to receive video data of the patient performing the biomechanical movements, separate the video data into individual frames, and analyze each individual frame of the video using a custom trained model to identify coordinates of keypoints in order to diagnose the patient; a patient portal in data communication with a processing and communication module, and the AI bot, the patient portal being configured to allow the patient to access a medical diagnosis; and a central database in data communication with the processing and communication module, an internal database, the AI bot and the patient portal, the central database being configured to facilitate an interconnection of the AI bot with the internal database, wherein the central database is configured to access an external database; wherein the internal database is configured to store data utilized by the AI bot to guide the user through the medical assessment, perform the medical assessment and diagnose the patient. An advantage is that the medical assessment may be a specific type of body region that requires analysis, such as a patient's back, neck, upper extremities, lower extremities, etc. A corresponding body region assessment (e.g., a back assessment) may be performed allowing the computer system to instruct a patient through a series of corresponding biomechanical movements to assess a patient's range of motion for said region, and to generate a corresponding diagnosis accordingly. Another advantage is that the computer system may be used to generate a standardized AI-determined diagnosis faster and more affordably than in person medical practices, while allowing for patients to report symptoms to assess preliminary health issues. Another advantage is computer system may be configured to generate a risk value for quickly assessing a patient's risk of experiencing musculoskeletal injury for specific body regions or conditions, thus providing patients, providers and other concerned parties with a readily understood measure of patient health. Another advantage is that the computer system may utilize standardized, machine learning algorithms and a database of patient data to diagnose patients based on previously undetected, asymptomatic risk factors.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which:

FIGS. 6A-6E illustrate the process of extracting joint angles from heel strike frames, for the angle based approach, according to an aspect.

FIG. 7A-7E illustrate the process of extracting joint angles from mid stance frames gait phases, according to an aspect.

FIG. 8 illustrates a summary of the manually generated rules for Heel Strike, Midstance, Toe-Off, and Mid Swing phases for the angle based approach, according to an aspect.

FIGS. 9A-9D illustrate the process of refining ankle separation data for utilization in the Keypoint Path Track-based Approach, according to an aspect.

FIG. 18 illustrates the comparison between the manually annotated angle measurements and API generated angle measurements for tests used to teach the algorithm for the angle-based approach, according to an aspect.

FIG. 19 illustrates the comparison between the manually annotated angle measurements (actual) and API generated angle measurements (predicted) for an independent test set for the angle-based approach, according to an aspect.

FIG. 20 illustrates the comparison between the manually annotated angle measurements and API generated angle measurements for an independent test set for the keypoint path track-based approach, according to an aspect.

FIG. 22 illustrates a deviation chart based upon a posture analysis, according to an aspect.

FIGS. 24A-24C illustrate the procedure for a patient performing a right thoracolumbar rotation range of motion measurement test, according to an aspect.

FIG. 24D illustrates an image captured by a camera being utilized to record the right thoracolumbar rotation range of motion measurement test for a patient, according to an aspect.

DETAILED DESCRIPTION

Figure 1A:
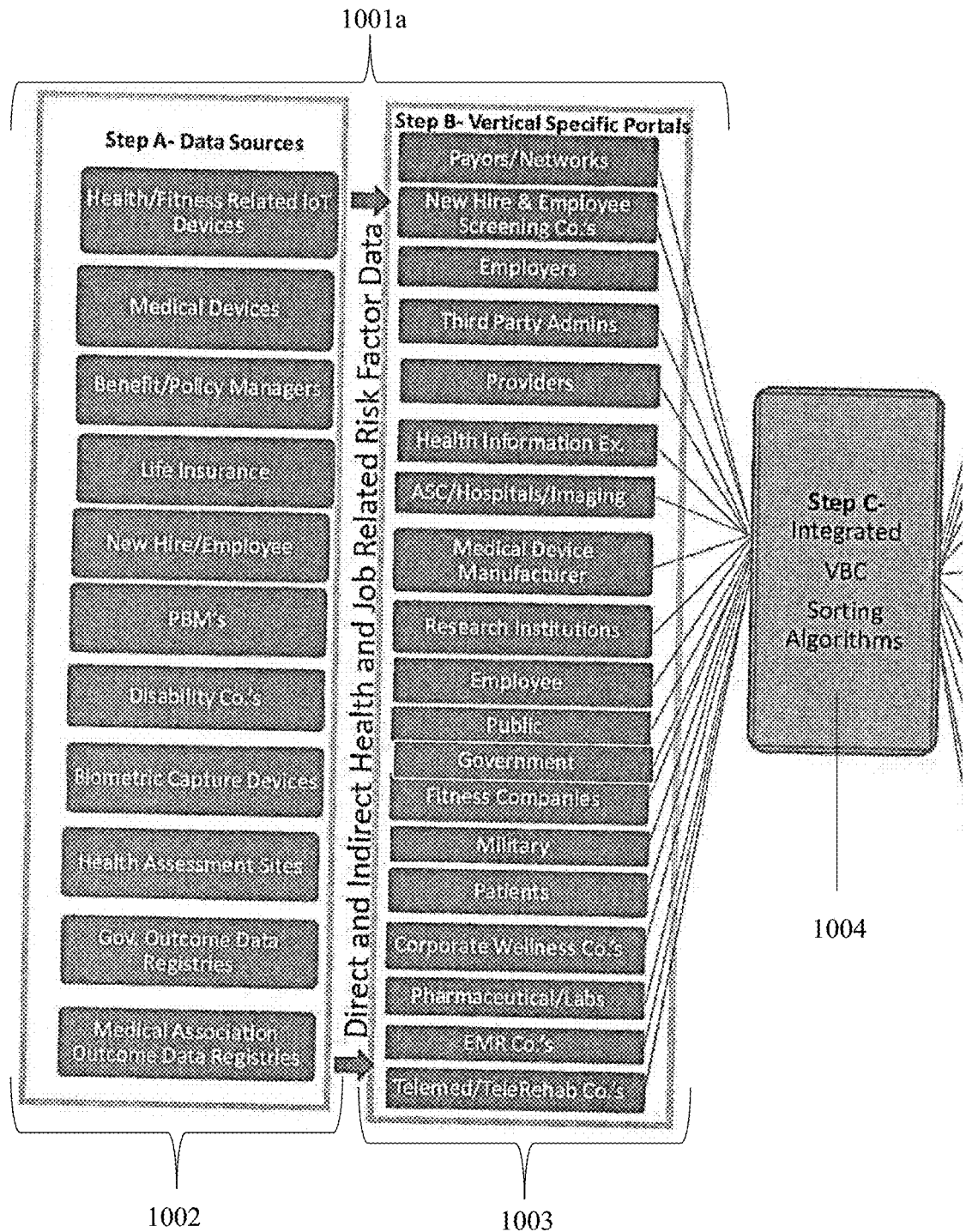
FIGS. 1A-1B illustrate diagrams of the herein disclosed report generation process, according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some structural components or steps that are known in the art are not shown or described if they are not necessary for the invention to be understood by one of ordinary skills in the art.

As used herein and throughout this disclosure, the term "mobile device" refers to any electronic device capable of communicating across a mobile network. A mobile device may have a processor, a memory, a transceiver, an input, and an output. Examples of such devices include cellular telephones, personal digital assistants (PDAs), portable computers, etc. The memory stores applications, software, or logic. Examples of processors are computer processors (processing units), microprocessors, digital signal processors, controllers and microcontrollers, etc. Examples of device memories that may comprise logic include RAM (random access memory), flash memories, ROMS (read-only memories), EPROMS (erasable programmable read-only memories), and EEPROMS (electrically erasable programmable read-only memories). A transceiver includes but is not limited to cellular, GPRS, Bluetooth, and Wi-Fi transceivers.

Mobile devices communicate with each other and with other elements via a network, for instance, a cellular network. A "network" can include broadband wide-area networks, local-area networks, and personal area networks. Communication across a network can be packet-based or use radio and frequency/amplitude modulations using appropriate analog-digital-analog converters and other elements. Examples of radio networks include GSM, CDMA, Wi-Fi and BLUETOOTH® networks, with communication being enabled by transceivers. A network typically includes a plurality of elements such as servers that host logic for performing tasks on the network. Servers may be placed at several logical points on the network. Servers may further be in communication with databases and can enable communication devices to access the contents of a database. For instance, an authentication server hosts or is in communication with a database having authentication information for users of a mobile network. A "user account" may include several attributes for a particular user, including a unique identifier of the mobile device(s) owned by the user, relationships with other users, call data records, bank account information, etc. A billing server may host a user account for the user to which value is added or removed based on the user's usage of services. One of these services includes mobile payment. In exemplary mobile payment systems, a user account hosted at a billing server is debited or credited based upon transactions performed by a user using their mobile device as a payment method.

For the following description, it can be assumed that most correspondingly labeled elements across the figures (e.g., 6076 and 7076, etc.) possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

Figure 1B:
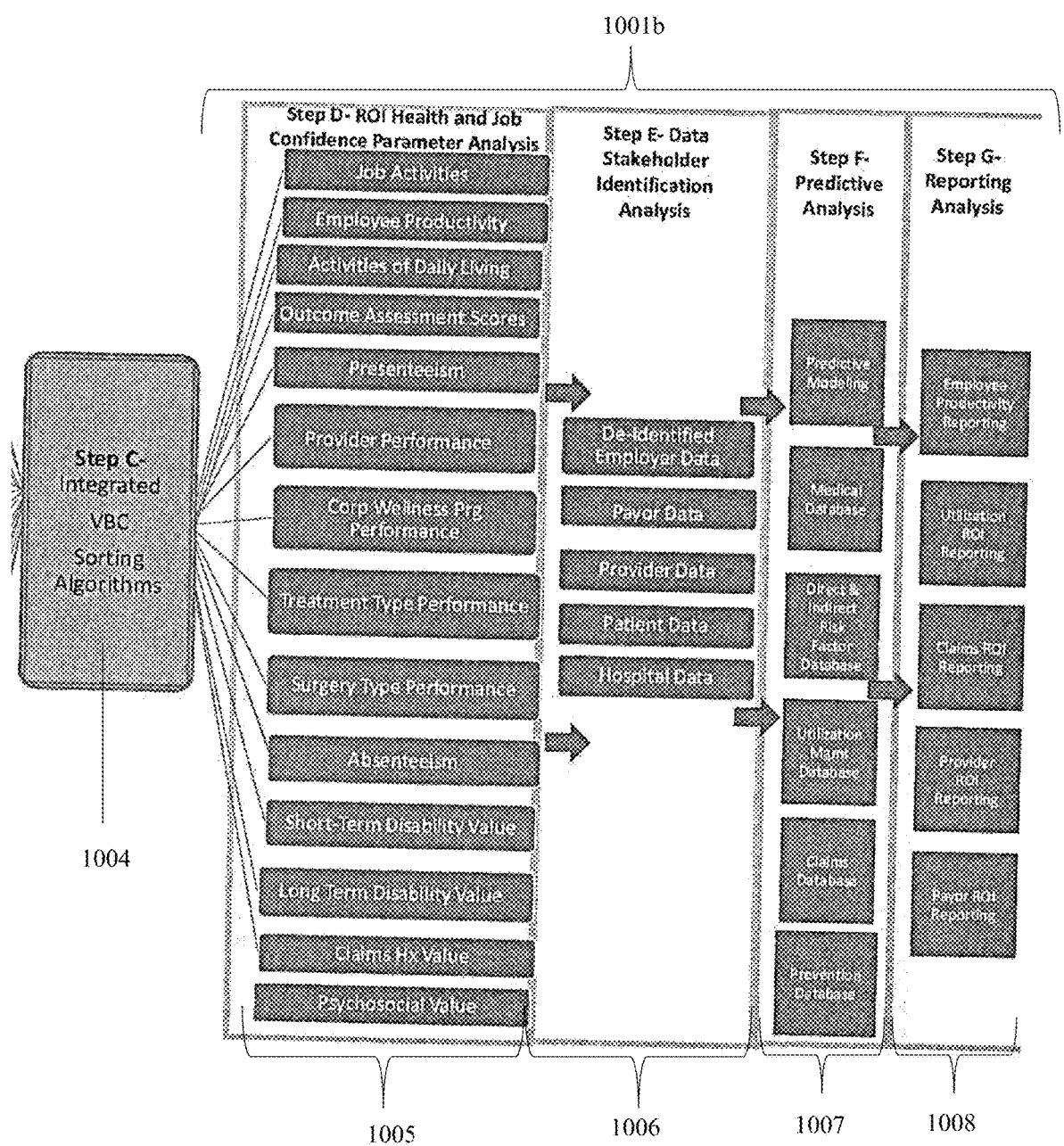

FIGS. 1A-1B illustrate diagrams of the herein disclosed report generation process utilized by the disclosed virtual care platform, according to an aspect. This disclosed report generation process may comprise three sub-processes: pre-analysis data collection 1001a, followed by utilization of value based care sorting algorithms 104, and finally post-sorting analysis and reporting 1001b. The pre-analysis data collection 1001a and post sorting analysis and reporting 1001b may each comprise a plurality of process steps, which will be discussed in greater detail hereinbelow. The report generation process disclosed in FIG. 1A-1B may identify and gather vertical-specific healthcare related data and organize, quantify, and report it in vertically specific, meaningful return on investment reports by reporting direct and indirect risk factors as they relate to return-on-investment (ROI) reporting. Furthermore, the resultant report result data can create the framework/anatomy of return-on-investment strategies based on direct and indirect risk factors impact on a specific individual's or population for a desired outcome (e.g., aggregated return on investment data may result in specific healthcare delivery and/or payment strategies to take place based on summation of confidence impact parameter values.)

The pre-analysis data collection sub-process 1001a may comprise two main steps: identification of data sources 1002 followed by classification of data into vertical specific portals 1003. The identification of data source 1002 may involve the identification of all potential data sources that may contain the desired, pertinent medical information that may be needed to produce a report for a patient or employee. As identified within FIG. 1A, such data sources may include health/fitness related IoT ("internet of things") devices, medical devices, benefit/policy managers, biometric capture devices, etc., which are configured to capture medical information that is relevant to a patient's health. This information may be utilized in order to identify both direct and indirect risk factors that may influence a patient's health. Upon identification of the relevant data sources, such information may be collected as needed. At least one source of stakeholder data and one intended use of stakeholder data may be determined, wherein each data element is associated with an impact parameter for the health or business-related conclusion relevant to the report being generated.

With the relevant data identified and collected, said data may be separated into appropriate classifications via vertical specific portals 1003. These vertical specific portals may be based upon the entity that is considered the stakeholder/end user (e.g., the entity requesting the resultant report). These vertical specific portals may include payors/networks, new hire and employee screening companies, employers, fitness companies, military organizations, providers accepting risk and value-based payment arrangements, etc. or anyone else that may have an interest (and suitable legal permission) in obtaining a report that influences their decision making, potentially with regard to economic ROI based factors. Upon classification of the data, the sorted data provided to the corresponding vertical specific portal may be processed by the value based care sorting algorithm 1004 discussed hereinbelow. The value based care sorting algorithm 1004 may sort and process the data collected within the corresponding vertical specific portal based on relevant factors and impact/level of confidence parameters. For each data element, a confidence parameter may be generated as a function of the health or business-related conclusion. These factors and parameters may be used to assess the prospective treatments and options and may be related to fiscal and/or health related outcomes.

Following the data processing of the value based care sorting algorithm 1004, the sorted data may enter the post-sorting analysis and reporting 101b sub-process. As can be seen in FIG. 1B, said sub-process may comprise four steps. The first post-sorting analysis and reporting 1001b sub-process step may be the return-on-investment health and job confidence parameter analysis 1005. The relevant parameters that may be analyzed in this step may include the patient's job activities, productivity, activities of daily living, as well as provider performance and various other parameters articulated in FIG. 1B. The relevant data is processed through an integrated customer resource system to process said data for the stakeholder's reporting needs. For each data element, a confidence parameter may be generated as a function of the health or business-related conclusion that is being pursued by the stakeholder.

Following the return-on-investment health and job confidence parameter analysis 1005, the collected data may be further processed within the data stakeholder identification analysis step 1006. Within the data stakeholder identification analysis step 1006, the collected data is processed into a compliant stakeholder database such as de-identified employer data, payor data, provider data and/or hospital data. The type of data provided in the stakeholder database may vary based upon the intended analysis to be performed and the type of report the stakeholder is pursuing. For example, an employer doing a primarily fiscal analysis may focus primarily on risk factors that correspond to confidence parameters capable of influencing wellness, reducing healthcare spending and missed work days, and enhancing the overall productivity and profitability of the business.

From the compliant stakeholder database(s) formed in the data stakeholder identification analysis step 1006 step, the predictive analysis step 1007 may be performed. In the predictive analysis step 1007, predictive modeling may be utilized in conjunction with available medical databases, direct and indirect risk factor databases, utilization management databases, claims databases and prevention databases in order to suitably generate the desired information required for a specific type of stakeholder report. An overall level of confidence parameter as a function of each of the relevant confidence parameters and the associated data impact values on corresponding region(s) of the patient's body needs may be generated for use in the following report.

With the necessary information collected, organized and processed, the final results of a stakeholder report may be provided in a reporting analysis step 1008. Depending on the stakeholder and their intentions, the type of information reported may vary. The types of reporting provided in the generated reports may include employee productivity reporting, utilization ROI reporting, claims ROI reporting, provider ROI reporting, and payor ROI reporting. These reports may be utilized by the applicable stakeholder in order to make fiscal decisions based on the results generated by the herein disclosed process. As described herein, the disclosed value-based care method of FIGS. 1A-1B gathers, organizes, quantifies and vertically specifically reports the direct and indirect risk factors as they relate to return on investment reporting.

The process that an end-user may utilize to generate a report using the disclosed system may be streamlined and straight-forward, allowing an end user to quickly and easily generate their desired report. In an embodiment, the end-user subscribes to access their stakeholder specific portal via a secure network connection. Data may be either manually or automatically exchanged with the integrated value-based care tracking protocols. Acquired data may be processed through an integrated customer resource management system to prepare/format/process data for the necessary stakeholder's reporting needs. Acquired data may then be transformed into a compliant stakeholder database (e.g., De-identification of data, if required), then acquired data may be processed to a health related or business conclusion report with a focus on direct and indirect health risk factors and their impact on the stakeholder's health related business decisions. The operation may be conducted through a health information exchange and tele-health portal that contains health and business related direct and indirect risk factors related to data processing, enabling users to select specific conditions to test for or body regions to access, answer a series of questions and perform job-specific, provocative biomechanical movements that are recorded on video and utilized for objective data capture against evidence-based historical values which in turn produce a comparison against a large population of such data, as will be described in greater detail hereinbelow. Integrated value-based care reporting of their positive findings can be shared as a communication tool to effectuate value-based care and direct to employer/payer type of relationships/agreements. The herein disclosed process for reporting health and business data will facilitate a more effective method of accurate, real-time pay for performance healthcare model.

The disclosed process of FIG. 1A-1B provides a method for collaboration and evaluation of health and business-related data to be shared and reported in a complaint value-based reporting system between all stakeholders involved. This process may be utilized either retrospectively to evaluate a prior health or business-related conclusions or prospectively to evaluate one or more hypothetical business related or health related conclusions. The disclosed process or method, which may be implemented as a back end at a node coupled to a customer resource management and health information network, such as the health information exchanges and electronic medical health records, may convert raw medical data into a report based on the stakeholders needs. As disclosed above, this method may perform business and health related present and predictive conclusion analysis and stakeholder specific reporting to evaluate one or more business or health related conclusions with respect to the selected body regions of an involved patient/employee.

As described herein, this disclosed report generation method may provide a mechanism for integrating stakeholder data through a value based care interface method for the purpose of categorizing/quantifying the collected data into corresponding bodily regions and risk factor stratification for the purpose of sharing, collaborating and predicting future health related events and tracking key performance clinical, employer, payer and case/utilization management metrics. The disclosed method may be applied either retrospectively to evaluate a prior conclusion, evaluate a present clinical or sub-clinical scenario or prospectively to evaluate in a predictive value-based care delivery program.

In an embodiment, a medical analysis site ("integrated value based care tracking analysis site") is hosted to a HIPAA compliant shared information portal. Clients, including the aforementioned stakeholders, may interact with the source of the data collection system/program or device via a compliant internet or mobile phone connection to the shared information portal for medical, quantitative, benchmarking, key performance index and predictive analysis. Said portal/site receives input data from consented stakeholders either in the form of raw data or medical records, which are further processed based on their intended use by the various stakeholders. An example of this is when an employee seeks care that a self-insured employer is paying for, and the employer cannot legally view the medical records of their employee due to HIPAA and PHI statutes. In this scenario, the disclosed system will "de-identify" (e.g., remove the patients name and identifiers) said patient's data and enable the employer to view the result of the treatment in a report, such as a return-on-investment productivity report, showing the aggregate impact of their employee population healthcare and corporate wellness program. This shared information will enable the employer to make more real-time and cost-effective decisions based on the care that they are paying for on their employee population as well as shape wellness and injury prevention programs based on specific, deidentified data and clinical criteria. The medical analysis site includes a front-end sub-portal (e.g., a World Wide Web server) for providing a graphical user interface ("GUI") for clients to interact with the site, a core engine, which perform at least one process for analyzing and evaluating incoming stakeholder data in order to appropriately and compliantly map that data for benchmarking and predictive decision making and reporting to another stakeholder's intended use. As such, the disclosed medical analysis site may utilize a patient record database, which shares normalized medical data relating to medical histories and assessment findings of patients, to draw medical and economic conclusions, of both current and predictive natures. It should be understood that the term "assessment" refers to a medical assessment within the context of this application, several of which will be referenced herein, with a gait assessment described in depth hereinbelow.

The integrated value based care tracking analysis site may share a predefined set of clinical and subclinical direct and indirect risk factors that represent normal events in an IoT device, medical device, fitness or wellness program, medical history including biometrics, direct and indirect risk factors to the human body, comorbidities, symptoms, treatments, clinical conclusions, laboratory tests, chronological factors, demographic factors, assessments, outcomes assessment scores, other health related scores intended to standardize care, diagnoses, utilization management, claims data and treatment plan data, etc.

According to an embodiment, the core engine includes a processor and relational databases, which further includes a customer service relationship system, clinical and sub-clinical health and job related essential element database, a medical phrase database, a chronological rules database and a medical knowledge rules database, predictive analytics rules and a corresponding database, telemedicine, tele-rehabilitation, electronic medical records system and various APIs for interoperability to the necessary stakeholder and source of data acquisition users. The integrated value-based care tracking system database may map each incoming data point to a monetary value, employer related value, clinical or sub-clinical value, claims value to arrive at a compliant report based on the stakeholder's specifications. Analysis of at least one clinical or business-related conclusion may use a membership confidence function and a criterion impact parameter, based on available research, datamining and other relevant sources of data. The membership confidence function relates a degree of confidence that a particular essential element points to a particular clinical or business conclusion as a function of clinical or sub-clinical assessment that is consistent with evidence-based research or historical claims/utilization data.

It should be understood that variations to the above-described process/methods, and its various elements, may be made while still remaining within the scope of the said process. In alternative embodiments, data gathering can be performed manually, and resultant stakeholder reports can be derived via manual calculations/formulas to derive confidence impact values for vertical specific use of data. More or fewer data sources may be utilized based on the stakeholder report being generated, as certain data sources may be more or less relevant to a stakeholder depending on their intentions. Other variations not explicitly disclosed may also be utilized, as needed within a specific application.

The disclosed health care analysis platform ("MyMedicalHub", "MMH", "platform", "virtual care platform") is a cloud-based, SaaS (software as a service), AI enabled virtual care platform designed to objectively quantify and stratify a patient's risk of musculoskeletal injuries and provide physicians, providers, and care coordinators with actionable data that promotes early detection, preventive engagement, and enhanced clinical care coordination. The disclosed platform is designed to transform the way musculoskeletal ("MSK") baseline assessments are facilitated as well as how longitudinal care plans are implemented and tracked. This is realized through the integration of virtual data capture, machine-learned AI, Bot-led assessments, and telemedicine capabilities. All of these aspects may be accessed through ubiquitous personal computing devices with no additional hardware requirements connected through the internet. The disclosed platform makes it possible to capture comprehensive MSK baseline assessments conveniently and cost effectively from the patient's home or any place with internet access, without the immediate aid or attention from a physician or other suitable provider.

MMH was designed as an AI enabled machine learning platform that standardizes and improves the quality of baseline assessment data for treating physicians and providers. This structured data capture allows for the utilization of machine learning techniques, thus enhancing the disclosed platform's ability to detect underlying conditions through a virtual assessment process and evaluate the patient relative to normative baselines for similar patient profiles. The disclosed platform operates as a virtual assessment technology configured to provide a quantitative value called a "Injury Risk Index Score" ("risk value") that is highly correlated to the risk of musculoskeletal injury, a value which takes into account both known, reported issues as well as asymptomatic, hidden medical conditions. Said platform is designed to enhance and extend the patient/doctor relationship though technological innovation that makes MSK care more convenient, higher quality, and more affordable, as will be described in greater detail hereinbelow.

The disclosed platform is configured to standardize the collection of data specifically related to musculoskeletal deterioration and identify conditional criteria that are precursors to more complex medical and surgical issues. The process of "machine learning" these criteria is a unique aspect of this platform and the data science approach. Through years of mathematical trials and errors, the disclosed platform has "learned" how to anticipate issues that impact its Injury Risk Index Score and expedite the integration of new findings and clinical criteria. Through a process of mathematical reengineering, testing, refinement, retesting, and statistical validation, the disclosed platform is capable of "learning" clinical protocols that drive desired patient outcomes through the scientific examination of correlations. The end result is the calculation of machine-based statistical relevance.

The platform's machine-based statistical relevance is used to secure, organize, and report a variety of information in a user-focused format. These "rules" comprise mathematical algorithms that quickly recognize and ingest new or unique data variations, compare them to an entire ecosystem of normalized data, and calculate relevance. As more rules are created, the technology becomes far more intuitive and efficient, therefore streamlining the amount of time required to absorb new data and clinical outcomes into the platform. This allows for the incorporation and adoption of new clinical studies, provider-defined protocols, and evidenced-based medicine and wide-spread adoption of statistically validated interventions, potential diagnosis, and care plans.

As described above, the disclosed platform is an AI-enabled virtual care platform that uses artificial intelligence and machine learning to create an objective measure called an Injury Risk Index Score. This Injury Risk Index Score is a value that is configured to stratify and track the risk of musculoskeletal injuries, while even accounting for risk factors that are asymptomatic. Subjective and objective data are virtually collected, quantified, and risk stratified at an individual level without the need for wearable devices, as will be described in greater detail hereinbelow. Said data is analyzed and embedded within an entire ecosystem of clinical research and evidenced-based studies. Said platform's AI-based technology may produce precise data based on each individual patient's personal self-assessment while identifying actionable information, such as early detection signs of MSK disease, thus identifying those who are at imminent risk for more complex interventions. The disclosed platform is designed to promote early detection, preventive engagement, and data-driven clinical care coordination throughout an entire episode of care, and beyond. The disclosed MMH platform is transformative and will empower system users, clinicians and a variety of additional users to better manage their own MSK health, by providing a mechanism to measure the effect of various interventions and said intervention's impact on individual musculoskeletal health status.

A unique quality of the disclosed MMH platform is its capability to standardize the collection and analysis of subjective and objective data through a virtual, internet, and mobile enabled platform. Said platform may collect and analyze 1,000s of points of data during every assessment. As stated above this capability may be realized through the integration of virtual data capture, machine-learned AI, and telemedicine capabilities, wherein each is deployed on a ubiquitous personal computing device(s), with no additional hardware requirements. The AI enabled machine learning platform collects, standardizes, and improves the quality of baseline assessment data for treating physicians, providers, case workers, and care navigators.

The disclosed platform's unique, low-cost, proprietary process for creating AI-based logarithms and machine-learning ecosystems of data is configured to create exceptional efficiencies for providers by virtue of its AI-driven clinical narratives, objective, numeric risk assessments, and suggested care plans and tracked interventions. While all care currently requires some level of human intervention, the utilization of internet-enabled AI significantly reduces the costs when compared to directly engaging providers, in all aspects of data aggregation and analysis. Furthermore, the internet-enabled AI can be extended globally, and cost justified relative to the current inadequacies and inefficiencies present within healthcare delivery and financing systems.

The disclosed platform empowers system users with direct access to their own individual data and information. In an embodiment, said platform resides on Microsoft's Azure and their Cloud for Healthcare, thus creating secure, ubiquitous access to an entire ecosystem of healthcare related data. In such an embodiment, test data, interoperable Electronic Health Records (EHRs), and a myriad of disparate medical information will be made available to users to care navigate and select the most appropriate array of medical, surgical, diagnostic, and ancillary service across an entire continuum of providers and locations.

The disclosed health analysis platform may make use of the aforementioned "Injury Risk Index Score" in order to provide patients, employers and other clients and parties of sufficient interest with an indication of the patient's likelihood to experience musculoskeletal ("MSK") injury. For analysis purposes, several distinct body regions may be identified, including the neck, upper extremities (arms), back and lower extremities (legs), each of which may receive an Injury Risk Index Score based upon each region's likelihood to experience MSK injury. The Injury Risk Index Score may be a fluid, functional value that provides a standardized method of identifying the contributing factors that predispose people to injuries, while providing an injury baseline or value for a specific body region. The Injury Risk Index Score for each body region can be used to benchmark treatment outcomes among one or several providers. For instance, it can track health improvements from pre- and post-surgery, and/or provide clinical support in an effort to help guide and monitor patients throughout the entire care continuum process. The disclosed Injury Risk Index Score may be reported not only as a diagnostic figure, but also a predictive one. Said Injury Risk Index Score may take into account identified degenerative issues and flag/indicate their presence before they become catastrophic events, enabling real-time and actionable health reporting. In short, the Injury Risk Index Score is designed to accurately and consistently represent significantly more patient information, and injury insight, than the medical assistant or physician could gather in an hour or more interview, through the incorporation of virtual assessments and other tools and procedures described hereinbelow.

Each of the various features and functions of the herein disclosed platform may be enabled by a corresponding system module(s) or component(s), as will be described in greater detail hereinbelow in FIG. 2 and beyond. The features enabled by the herein disclosed health analysis platform may include a health tracking journal, machine-learned, automated stretches and therapeutic exercise interventions, care navigation and integrated scheduling, case management, custom dashboards and reports, screening assessments such as posture screening assessment and regional screening assessments for the neck, back, arms, and legs and/or whole body, a MMH prospective outcome modeling tool, a specialty screening assessment for gait, therapeutic stretches and exercises, a balance and fall assessment program, a workers compensation management program, and an objective chiropractic posture alignment plan. Additional features including specialty screening assessments for hands and feet, orthotic & custom bracing fitting programs, a concussion screening and assessment, diagnostic image analysis, an orthopedic implant sizing program, health and fitness programs, molecular MSK pharmacological programs, and a rules-based patient communication tool are also in development to further supplement the existing features of the disclosed health analysis platform. Each system, method, procedure, etc. may be described as being "self-led" (e.g., led/initiated by the patient), "AI-led" (e.g., led/initiated by the AI of the disclosed platform) and/or "provider-led" (e.g., led/initiated by the medical provider/hospital/doctor) or some combination of the three. Certain features may be led, performed or aided by multiple parties, depending on the context of the analysis and who the client, stakeholder or party of interest is. The "client" may be any applicable party with sufficient legal clearance to access the applicable results.

The disclosed health analysis platform may be configured to operate using an advanced platform and networking structure. For example, MyMedicalHUB is partnered with Microsoft's Cloud for Healthcare and resides on Microsoft Azure, a secure HIPAA complaint platform that integrates data based on standard industry protocols. By utilizing an automated computer-based system, the disclosed health analysis platform may allow for rapid, efficient data collection and analysis without direct or immediate provider interaction, thus optimizing efficiency.

The health tracking journal may be a self-led operation in which a patient may voluntarily provide medical comments and issues regarding their own health for analysis. Users of the disclosed platform are able to create their own individual health tracking journals chronicling a variety of issues and initiatives relating to their personal health. These journals may automatically embed, combine, and track data from the platform's assessments and an individual's entries or therapeutic exercises that can be used to trigger clinical provider interventions, in the event of adverse physiologic issues or patient inputs, such as a high VAS (visual analogue scale) score. Through utilization of this health tracking journal, patients may objectively measure, track, and manage their own personal health status as well as share relevant, actionable information with their healthcare providers or care coordinators. The health tracking journal may allow a patient to provide new information for their medical records quickly and easily without the immediate need for physician analysis.

The care navigation & integrated scheduling feature may be an AI-led procedure in which the health analysis platform analyzes available patient information based on existing analytics. The disclosed platform may utilize over 1,000 evidenced-based studies and protocols in its automated care navigation processes. Information from screening assessments is analyzed using the platform's proprietary machine-learned algorithms to risk stratify each individual patient and suggest suitable interventions. These interventions may include exercises, therapy, ergonomic considerations, and clinical provider engagements, wherein the disclosed health analysis platform is integrated with provider scheduling systems, protocols, and workflows. Client defined protocols can also be embedded within the navigation system.

The case management system may be accessible via a "provider portal" and may be provider-led. The provider portal may be configured to track all assessments and interventions using discrete episodes that are user defined and initiated. Reports, dashboards, intake questions (potentially as part of "questionnaires"), and Health Tracking Journals can be customized to provider and employer specification, as needed. Clinical data, workflows, and scheduling integration can be customized and facilitated through Microsoft's Azure Cloud for Healthcare or similar user defined HL7 compliant interfaces. This functionality can be used to collect data and manage care on a per-episode basis.

The custom dashboards and reports may be client defined, wherein the client would be the individual or organization utilizing the platform. As such, the complexity and scale of the dashboards and reports may vary based on the client. MyMedicalHUB platform utilizes state-of-the-art programming tools to create client specified dashboards and reports based upon client needs.

The screening assessments may be "self-led" or "provider led" and may utilize the assistance of the herein described AI. The MMH platform can perform a variety of screening assessments, based on the body region or physiologic condition targeted for assessment. Each assessment may contain a series of intake questions that are customizable and can include Activities of Daily Living (ADLs), Chief Complaints, and up to 61 machine-learned biomechanical movements specifically designed around provocative tests. All screening assessments can be performed without a human by the disclosed AI Bot, EMMA, ("Efficient Musculoskeletal Management Assistant," "AI bot," "AI," "EMMA system"), or under the live supervision of a provider, care coordinator, case manager, or physician extender via an integrated telehealth function. No special hardware or wearable devices may be needed, and the collected information is virtually collected through any type of computer or smart device (cell phones, tablets, mobile devices, computers w/cameras, etc.) connected to the internet. Data is inputted into MMH's AI machine-learning platform, compared to approximately 25,000 (and growing) assessments, and used to create an objective Injury Risk Index Score, possible care classifications, and suggested interventions as part of a comprehensive provider report. The provider report includes all related images, measurements, clinical studies, evidence-based articles, or user-defined clinical protocols. As part of the machine learning process, providers can override the AI and amend reports based on their independent clinical judgement. As more tests are performed within the disclosed machine learning health analysis platform, the AI of said platform will draw stronger correlations and become more precise and intuitive.

Regional assessments for a patient's neck, arms, back or legs may be "self-led" or "provider led" and may utilize the assistance of the herein described AI. The neck screening assessment identifies an individual's risk level as well as common injuries of the neck. Users (e.g., patients) may perform a series of movements designed around provocative neck tests. Said neck screening assessments may utilize cervical range of motion (ROM) in flexion, extension, lateral bending, and rotation. The upper extremity (arms) screening assessment identifies an individual's risk level as well as common injuries of the arms. Users may perform a series of movements designed around the provocative upper extremity tests. The arm screening assessment may utilize upper extremity ROM in flexion, extension, lateral bending, and rotation. The back screening assessment identifies an individual's risk level as well as common injuries of the back. Users perform a series of movements designed around the provocative back tests. The back screening assessment may similarly utilize back ROM in pelvic, lumbar, and thoracic regions as well as total flexion, extension, and lateral bending. The lower extremity (legs) screening assessment identifies an individual's risk level as well as common injuries of the legs. Users perform a series of movements designed around the provocative lower extremity test. It also utilizes lower extremity ROM in hip adduction, knee flexion and extension.

All of the above tests may be incorporated into a singular full-body screening assessment, in instances in which a better understanding of a patient's overall health may be required or otherwise useful. It should be understood that the "user" for the above-described assessments would be the patient or employee on which the assessments are being conducted. These assessments may be utilized to identify hidden health factors that would otherwise be too time consuming or difficult for a provider to find themself in the limited time they have to interact with a patient during a standard medical appointment.

A posture screening assessment may be "self-led" or "provider led" and may utilize the assistance of the herein described AI. The posture screening assessment tool is simple, fast, and identifies nine of the most common posture deviations: forward head carriage; rounded shoulders; scoliosis; kyphotic posture; anterior pelvic tilt; posterior pelvic tilt; deviation from midline at the knees; deviation from midline at the hip; and deviation from midline at the shoulder. In this way, these recognizable deviations may be quickly identified in patients without needing said patients to enter a doctor's office or hospital. It should be understood that fewer or additional posture deviations may be searched for based on the patient's risk factors, age and other demographic details.

In addition to assessing the patient's MSK health from a body region standpoint, additional information about a patient's health may be understood from a screening assessment of their gait. A gait screening assessment may be self-led or provider-led, and may utilize the assistance of the prior disclosed AI/AI bot, and may be used to identify issues derived from, indicated by or otherwise related to the patient's gait. By identifying potential health concerns based upon the major body regions discussed above, as well as a patient's gait, it may be far easier to attain a full understanding said patient's MSK health prior to any kind of in-person medical appointment or intervention. An example gait assessment will be described in greater detail hereinbelow.

The MMH prospective outcome modeling tool may be a provider or patient-led tool configured to create realistic goals for a patient's growth/recovery. It can also be utilized by insurance companies and self-funded employers in populations of covered members to model risk and potential healthcare expense reductions, as well as by payors in value-based reimbursement and compensation models. Said tool may allow clinical users and other providers to model individual factors based on their correlation to outcomes to create objective, quantifiable goals and targets that can be measured over time. This outcome modeling tool may utilize the generated Injury Risk Index Score and can also include embedded cost or fee data, where applicable, to help both patients and providers identify the most suitable treatment options. Providing tangible, attainable goals for a patient during their recovery or general health improvements may help to keep them on track and ensure the proper follow-up therapies and procedures are utilized.

Machine-learned therapeutic stretches and exercises may be self-led, or provider led with the assistance of the herein described AI. It is a low-cost alternative to outpatient physical therapy intended for lower complexity patient conditions. MyMedicalHUB may utilize over 500 therapeutic stretches and exercises, including over 180 (and growing) that are machine-learned by the AI. In an embodiment, the disclosed AI may utilize proprietary angle-based and keypoint detection data capture techniques, such as those described in the gait analysis section hereinbelow. Said AI may be configured to watch someone perform the movement through a suitable camera device and "virtually teach" users how to perform them correctly. The stretch and exercise system also counts, tracks, and reports activity within the aforementioned user health tracking journal. Therapeutic exercises can be assigned by AI or a clinical provider who utilizes the disclosed health platform. These therapeutic exercises help patients avoid further injury as well as recover more quickly and reliably from an injury without needing the guidance of a trained professional in all cases.

A balance and fall risk assessment program may be self-led or provider led and may utilize the assistance of the herein described AI. A specialized intake questionnaire, gait, posture, and biomechanical analysis may be specifically designed to identify, measure, and track fall risk. Fall risk may be a hidden risk factor that may be harder to identify and quantify due to the variety of information required to properly assess it, but the mechanisms employed by the herein disclosed health analysis platform allows for the procurement of all the mentioned necessary information needed to provide an accurate assessment of the patient's fall risk. This information may be highly relevant for aging patients or patients for whom falling could cause a serious medical episode. Said information may also be applied to athletes in an effort to enhance performance.

A worker's compensation and personal injury management program may be provider-led. Custom intake questions and therapeutic exercises aligned to physical job requirements and objective screening assessments may allow for condition-specific interventions and more precise case management at an individual level, as well as the ability to track compliance with rehabilitative progress longitudinally using auto-populated health tracking journals and administration of learned therapies assigned/approved by providers. By monitoring a patient's condition as they heal from a surgery or other conditions that otherwise prohibit them from working, the disclosed health analysis platform may allow for the proper recovery procedures to be used, while indicating that the patient is either fit or unfit to safely resume his/her previous duties; however, the technology is also capable of identifying, through objective measurements and data analysis, jobs within the company that can be safely performed, allowing the employee to reengage in the workforce as opposed to remaining at-home in a paid status.

The efficient chiropractic alignment program may be self-led, or provider led and may utilize the assistance of the herein described AI. An automated posture assessment tool that identifies posture misalignments may be provided as a feature within the disclosed health analysis platform and may be further configured to allow providers to input subjective annotations. By providing patients with an easy method to assess their posture, posture issues may be easily identified to provide additional insight into said patient's physical health, without needing to enter a doctor's office or hospital.

While the above features may already be implemented within the disclosed health analysis platform, additional features, systems, and programs are in development that may further enhance the range of medical information that may be identified and services that may be provided. Specialty screening assessments for a user's hands and feet may be self-led or provider led, may utilize the assistance of the herein described AI, and be provided in a comparable fashion to the assessments described above for the arms, legs, neck and back, thus providing additional diagnostic information. A diagnostic image analysis program may be AI-led, wherein the disclosed platform's AI analyzes musculoskeletal images (MRIs/X-Rays/CT-Scans) to quickly identify potential care classifications and abnormalities. An orthopedic implant sizing program may be AI-led and utilize the above mentioned musculoskeletal images (MRIs/X-Rays/CT-Scans) to create precise, automated measurements for orthopedic implant templating and include a streamlined, automated fabrication and just-in-time delivery tool. A molecular MSK pharmacological program may be AI-led and may utilize molecular genetic profiling and may apply its AI/Machine-Learning processes to identifying the most efficacious pharmaceutical and biologic care interventions.

Additionally, a rule-based patient communication tool may be AI-facilitated within the disclosed health analysis platform. Said health analysis platform may provide a state-of-the-art communication platform that customizes omnichannel, patient-specific communications (precision communications) based on user-defined criteria that includes, but is not limited to, Injury Risk Index Score, diagnosis code (ICD-10), procedure code (CPT), geographic, and proprietary data. The patient communication tool may also automatically and objectively calculate communication related effectiveness and ROIs. Furthermore, this patient communication tool may provide an effective platform that can be used for marketing (existing and new patients), patient education, newsletters, and other interests. Such a communication tool may be developed based upon the needs of the patients and may include additional communications that may serve to benefit patients, prior to, during and after medical incidents. Said communications may also notify patients with effective preventative care measures that may be taken to prevent issues from occurring in the first place, based on their Injury Risk Index Scores or other health factors.

It should be understood that the above tests, assessments, analyses and other features may serve purely as exemplary embodiments of potential features that may be employed by the disclosed health analysis platform to help diagnose, treat and monitor patients. Features including balance & fall risk assessments, AI-based automated diagnostic image analysis & interpretation, AI-based automated surgical implant templating, AI-based molecular genetic-based pharmaceutical & biologic optimization and AI-based neuro-muscular concussion screening & tracking, amongst other possible features, may be provided in order to identify both known and hidden health factors that may be critical in deciding on a patient's treatment options. Additionally, while the focus of the herein disclosed platform may be on musculoskeletal diagnostics and health, it should be understood that the same techniques and mechanisms may be applied to other medical focuses, such as diabetes, cardiovascular, neurologic, dermatology, as well as allergy and immunology.

It should also be understood that each feature of the health analysis platform outlined hereinabove may be carried out by a corresponding module responsible for enabling the described feature. For example, the "health tracking journal" feature may be provided by a health tracking journal module. Said health tracking journal module may be configured to provide a patient utilizing said platform with an interface to enter their medical comments and concerns as disclosed above and be in data communication with a server or database that is utilized to store said medical comments and concerns. This health tracking journal module may further be in data communication with the AI/AI bot, which may be utilized to modify and curate this information. The health tracking journal module may utilize a shared storage database or may have its own storage server, either of which may be in data communication with the aforementioned AI bot. The data communication established between the AI bot and each applicable component/module of the MMH system will be described in more detail hereinbelow in FIG. 2.

In order to enable suitable function of the disclosed health analysis platform, it is critical that the machine learning AI disclosed herein be in data communication, either directly or indirectly, with all corresponding modules that are utilized to store and process medical information, as well as each module that is utilized to report or communicate medical results. As the AI may be the entity responsible for generating results, such as Injury Risk Index Scores from the collected medical information, each module utilized to enable the features disclosed herein must, at minimum, be in indirect data communication with this AI responsible for analyzing and processing data. An indirect data communication between an indirect module and the AI may utilize one or more intermediary modules or components to establish a communication channel between the AI and the indirect module. In an embodiment, all necessary data, including patient medical information and reference information utilized by the AI may be stored within a unified server as part of the Microsoft Azure cloud computing service. Alternatively, patient data may be stored separately from the reference data used by the AI for machine learning, to further ensure data security is maintained.

Figure 2:
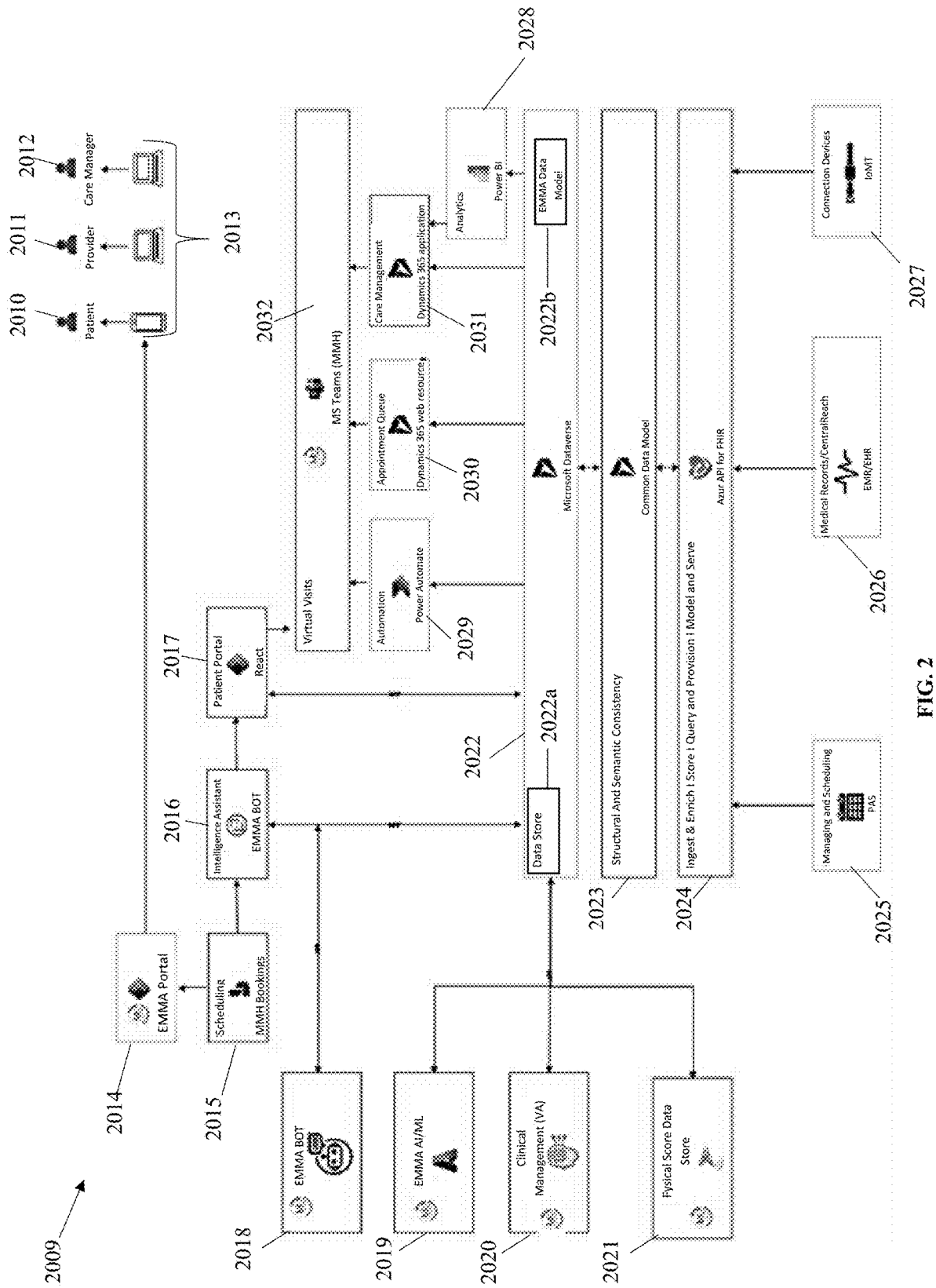
FIG. 2 illustrates the design diagram for the MMH (MyMedicalHUB) system, according to an aspect.

FIG. 2 illustrates the design diagram for the MMH system 2009, according to an aspect. It should be understood that each arrow depicted interconnecting the various systems, databases, users, etc. of the MMH system 2009 indicates that each of the disclosed elements are in data communication with each other. A singular arrow may be used to represent data being pulled from an element at the tail of the singular arrow to an element at the arrowhead of the singular arrow, whereas double arrows indicate the two elements may push and pull data to and from each other. It should be understood that while the disclosed design diagram of FIG. 2 may include specific programs, modules and systems, such as the Microsoft Dataverse 2022, variations of each, such as other storage platforms, may be implemented in their place, as discussed hereinbelow.

Patients 2010, providers 2011 and care managers 2012 may access the MMH System 2009 by accessing an EMMA portal ("main portal") 2014 through the utilization of a suitable web-enabled device 2013, such as a smartphone, tablet or computer. It should be understood that the EMMA portal 2014 may be the same for the patient 2010, provider 2011 and the care manager 2012, but said EMMA portal 2014 may provide only the information relevant to or allowed for said user, based on their role. Said EMMA portal 2014 may pull data from the scheduling module 2015 responsible for indicating relevant MMH bookings and appointments to the user.

Said scheduling module 2015 may be in data communication with the intelligence assistant 2016 provided by the EMMA bot storage database ("Bot database") 2018. This intelligence assistant 2016 may be responsible for asking patients questions and collecting results, including both initial and follow-up questionnaires, and prompting patients with relevant questions and information. The scheduling module 2015 may make use of an existing scheduling software such as Microsoft Teams to provide a scheduling database. The intelligence assistant 2016 may push data to a patient portal 2017, which may act as a patient interface with the EMMA portal for patients to access relevant information pertaining to their health and other medical information, perform and review assessments, etc. In addition to its intercommunication with the scheduling module 2015 and the patient portal 2017, the intelligence assistant 2016 may be in data communication with both the EMMA bot storage database 2018 and the Microsoft Dataverse 2022 in order to allow the AI assistant EMMA bot 2016 to provide a user, such as a patient 2010, with necessary information.

The Microsoft Dataverse 2022 may act as a data hub, behaving as a central system component through which relevant information may be pushed and pulled to both collect and store on databases and access for usage from said databases. The Microsoft Dataverse 2022 may be in direct data communication with the internal database, including the EMMA bot storage database 2018, the EMMA AI/ML storage database 2019, clinical management storage database 2020, and the Injury Risk Index Score data store database 2021, thus allowing information to be pushed and pulled to and from the internal database quickly and easily. As can be seen in FIG. 2, the Microsoft Dataverse 2022 may also be in data communication with a common data model 2023 and by extension the Azure API for FHR 2024 in order to facilitate data transfer from external databases. It should be understood that the Azure API 2024 may be provided as a potential embodiment of the API configured to access external databases, and that any API configured to perform this operation may be used, as will be described in greater detail hereinbelow.

These external databases may include a managing and scheduling database 2025, a medical records/CentralReach database 2026 and a IoMT ("internet of medical things") database 2027. Information acquired from these external databases may be helpful to supplement the information acquired through the conducted assessments and questionnaires, as having a knowledge of a patient's medical history may help provide a more precise indication of which follow up tests and assessments should be performed. A storage platform, provided as the Microsoft Dataverse 2022 in the herein disclosed embodiment, may include two subcomponents: a datastore 2022*a* in which pertinent information may be stored when being transferred between the various interconnected databases and interfaces and an EMMA data model 2022*b*.

In contrast to the external database, each of the sub-databases of the internal database may be responsible for holding information directly relevant to the inner workings of the MMH system 2009 and its generated reports. In addition, confidential information pertaining to system operations may be stored on these internal databases to suitably provide additional safeguards from it being accessed externally. The EMMA AI/ML (machine learning) database 2019 may be responsible for storing information pertinent to the machine learning algorithms, and the overall function of the EMMA AI. The Clinical management (Virtual assistant) database 2020 may contain data and a decision tree necessary for the operation of the virtual assistant EMMA bot 2016 and reporting, and may contain lists of possible questions, prompts and exercise instructions. The Injury Risk Index Score Data Store database 2021 may include processed information, such as patient Injury Risk Index Scores, and the information immediately relevant to its generation and other transactional data. It should be understood that the information required to conduct assessments, store and process the assessments and utilize the assessments to provide Injury Risk Index Score may be divided between the EMMA AI/ML (machine learning) database 2019, the Clinical management (Virtual assistant) database 2020 and the Injury Risk Index Score Data Store database 2021. An exemplary gait assessment that has been conducted will be discussed in greater detail hereinbelow.

The Microsoft Dataverse 2022 may push information to a variety of other automation and processing based utilities, including an automation program capable of building and enabling automated processing, such as Power Automate 2029, a queuing and organization application capable of providing the appointment queuing and care management practices, such as Dynamics 365 Applications 2031 alongside Dynamics 365 Web Resource Systems 2030, and an analytics generation program that provides the necessary analytics generation and processing capabilities utilized in the generation of medical reports, processed medical data, such as Power BI 2028. Again, while the disclosed embodiment may describe specific programs, applications and modules that may be utilized to achieve the necessary functionalities, it should be understood that any program/application/module suited to perform the same tasks may be implemented in their stead. Power BI 2028 may push its processed analytics into the care management system to allow their subsequent presentation. Each of these modules may then push their generated information to MS teams 2032 to allow for its utilization during virtual visits and other relevant applications. It should be noted that MS Teams 2032 may also pull information from the patient portal as needed for the virtual visit.

It should be understood that while the disclosed embodiment of FIG. 2 may identify capable Microsoft programs, applications and tools that may be used to enable system functionality, equivalent alternatives may be employed as long as the same functionalities are provided. The Microsoft Dataverse 2022 and common data model 2023 may be replaced by any situatable storage platform to provide the necessary functionality, while the Azure API of FHIR may also be replaced by any suitable API that allows for communication between the storage database and the external databases.

Similarly, Power Automate 2029 may be replaced by any suitable automation program capable of building and enabling automated processing. In an embodiment, Dynamics 356 web resources 2030 and the Dynamics 365 application 2031 may be replaced with any suitable system capable of providing the appointment queuing and care management practices utilized by the MMH system. In an embodiment, Power BI 2028 may suitably be replaced by other analytics generation processes that provide the necessary analytics generation and processing capabilities utilized in the generation of medical reports, processed medical data, etc. Teams 2032 may also be replaced by any suitable web conferencing infrastructure that would facilitate virtual visits, such as telemedicine communications, between a patients and care providers, In short, the specific embodiments provided in FIG. 2 that are specific to a certain program or company (e.g., Microsoft) should be understood to indicate the potential for using alternative embodiments of each program, system or module that are provided as a component of the MMH system.

The overall structure of the disclosed MMH system 2009 may be summarized succinctly by categorizing certain related elements into subcategories of said MMH system. The EMMA bot storage database 2018, the EMMA AI/ML storage database 2019, the clinical management storage database 2020 and the Injury Risk Index Score Data Store database 2021 may be grouped together and classified as an internal database, wherein said internal database is configured to securely store patient health information and data pertinent to the operation of the AI bot, Injury Risk Index Score calculations and report generation. The scheduling database 2025, a medical records/CentralReach database 2026, and the IoMT database 2027 may be grouped together and classified as an external database, wherein said external database is configured to securely provide access to pertinent medical information not generated by the MMH system, but that is needed to determine a more complete medical history for patients.

In order to simplify the MMH system components utilized for interconnecting the various subsystems as a hub, the Microsoft Dataverse 2022, Common data model 2023, and 2024 Azure API for FHIR may together be classified as central database, wherein said central database is responsible for facilitating data communication between the internal and external database, as well as the AI bot and a fourth subcategory of components referred to as a processing and communication module. Again, it should be understood that all modules depicted in the figures and described herein by their particular commercial name (e.g., Microsoft Dataverse 2022, etc.) are provided solely for exemplification purposes. These modules may be substituted with functionally equivalent modules (e.g., Storage platforms, etc.) from other providers (e.g., Amazon).

The aforementioned processing and communication module may comprise the Power BI 2028, Power automate 2029, Dynamic 365 web resource and Dynamic 365 applications, or as described above, their utilized functional equivalents. This aforementioned processing and communication module may be in data communication with the patient portal as well as the central database. It should be understood that the prior described data communication between the user device 2013, EMMA portal 2014, scheduling module 2015 AI bot 2016, and the patient portal 2017 may be maintained with the described MMH system subcategories, such that the EMMA portal is in data communication with the internal database and the central database, and the patient portal is in data communication with the processing and communication module.

Overall, the disclosed MMH system 2009 makes use of both internal and external databases containing both preexisting and newly generated information in order to create reports and track patient progress through a medical care episode. The disclosed MMH system 2009 may also take full advantage of the available Microsoft systems including Teams 2032, Power Automate 2029, the Microsoft Dataverse 2022, Azure API for FHR 2024, etc., in order to realize a semi-autonomous health care platform configured to supplement the existing physician facilitated care system that is currently utilized.

One benefit of using the segregated/partitioned data structure displayed within FIG. 2, wherein a plurality of separate databases is used, each of which houses a different type of information, is that information may be easily accessed by querying a smaller database having the needed information, rather than the larger database having all of the stored information. One result of this is that the data may be accessed and utilized more rapidly as a result of the reducing the processing power required to access it, thus expediting report generation. By reducing the processing power required to access and acquire the necessary data, additional system capabilities may be enabled to run simultaneously with reduced overall process load.

Depending on the signal strength available to a user in an area, the MMH system 2009 may be configured to adapt to the user's environment. In an embodiment, the MMH system 2009 may be configured to allow the user device, such as a mobile device, to handle a portion of the information processing prior to data transmission. This may significantly expedite data processing in instances in which the user's device has a poor internet connection by preprocessing the collected raw data from assessments, tests, etc. on the user's device, allowing only the smaller file size of the processed data to be forwarded over the internet to expedite data transmission times.

It should be understood that each internal database, including the EMMA bot storage database 2018, the EMMA AI/ML storage database 2019, clinical management storage database 2020, and the Injury Risk Index Score data store database ("risk value database") 2021, may both push and pull data from the Microsoft Dataverse 2022 in order to facilitate the required data transfer to enable system functionality as described herein. As disclosed hereinabove, by segregating/partitioning these databases, their information may be accessed more rapidly, expediting report generation while using less processing power than if all of the information were stored on a singular storage database.

One of the key benefits of the disclosed MMH system 2009 is the automation that it enables within the preexisting health care infrastructure. Medical assessments and reports may be generated automatically without user or provider intervention. Procedures such as surgeries other treatments may still requires human intervention, but the automation enabled by the MMH system's ability to collect, process and utilize pertinent medical information allows it to significantly expedite diagnosis, interventions, and treatment in many instances.

Figure 3A:
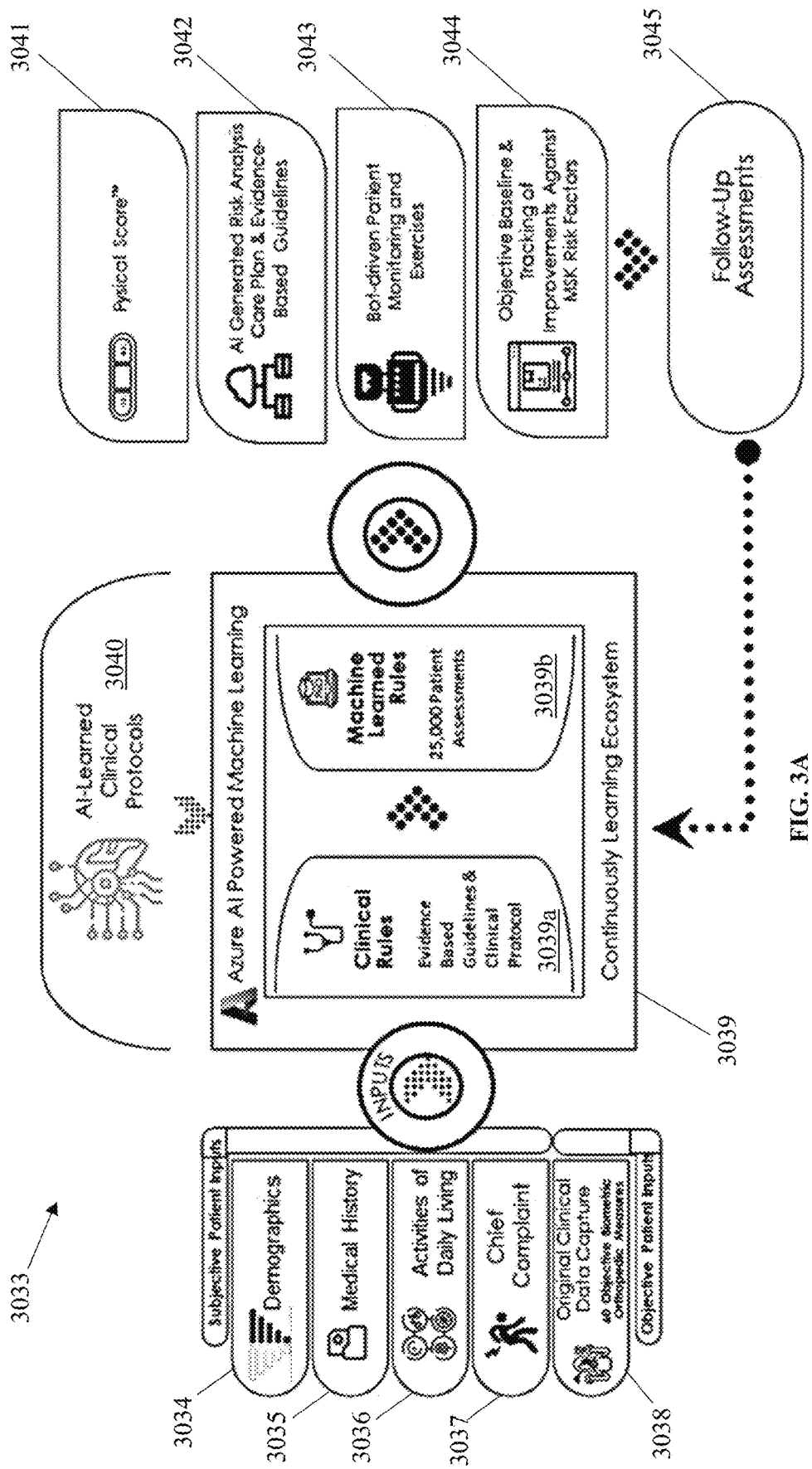
FIG. 3A illustrates a simplified process flow overview of the MMH system, according to an aspect.

FIG. 3A illustrates a simplified process flow overview of the MMH system 3033, according to an aspect. As can be seen in FIG. 3, the information that is supplied to the MMH system may include both subjective and objective patient health inputs. The subjective patient health inputs may include demographics information 3034, medical history 3035, activities of daily living 3036 and chief patient complaints 3037. It should be noted that the demographics information 3034 and medical history 3035 may be collected from external sources, whereas the activities of daily living 3036 and chief patient complaints 3037 may be collected by the intelligence assistant EMMA bot, such as the intelligence assistant EMMA bot 2016 of FIG. 2. The objective patient health inputs may come in the form of the hereinabove mentioned original clinical data capture 3038 that results from the herein disclosed medical assessments. As previously mentioned, these medical assessments may include body region based assessments (upper or lower extremities, back, neck, etc.), posture assessments, balance and fall risk, and gait assessments, as well as any other tests that may be relevant to assessing a patient's health.

These health inputs may be fed into a machine learning system 3039. The machine learning system 3039 may be "trained" by utilizing AI learned clinical protocols 3040 in conjunction with clinical rules 3039a, including evidence-based guidelines and clinical protocols in order to generate machine learned rules 3039b. These machine-learned rules 3039b may be based upon large quantities of patient assessments, allowing the machine learning system to identify trends based upon patient test results and provide useful insights into patient health. By feeding the prior disclosed health inputs into this machine learning system 3039, a plurality of health outputs may be obtained.

The health output obtained from the machine learning system 3039 may include both diagnostic information as well as potential remedial activities that may be performed in response to the diagnostic information. These health inputs include an Injury Risk Index Score 3041, an AI generated risk analysis care plan & evidence-based guidelines 3042, a bot driven patient monitoring protocol and exercises 3043, and objective baselines & tracking of improvements against MSK risk factors. The disclosed output not only provides patients with an indication of their current health, but also underlying risk factors that may not have been known previously, allowing for a comprehensive health summary to be provided in the form of a generated comprehensive health report. This information output from the machine learning system may also include a call for follow-up assessments 3045, which may be utilized to continue analyzing a patient's health as they recover or progress through a health itinerary.

Figure 3B:
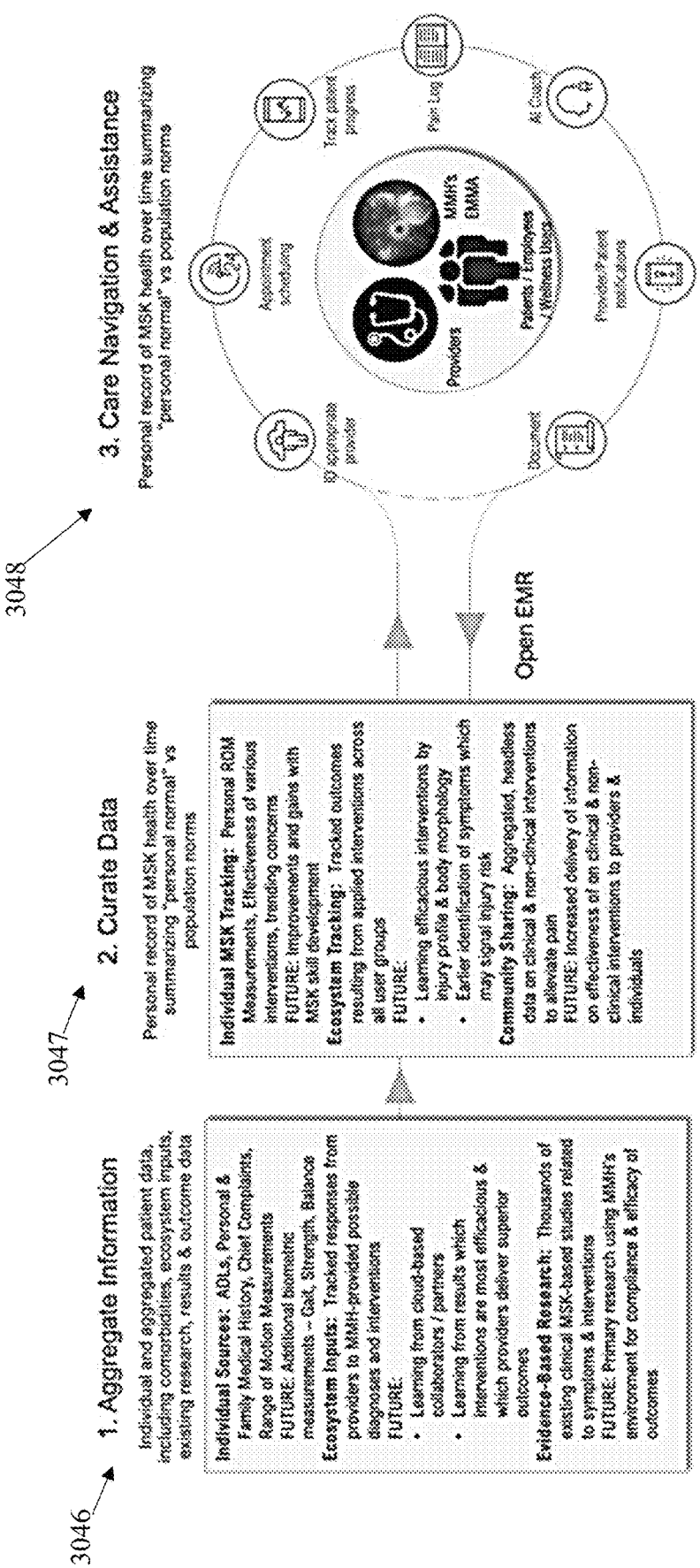
FIG. 3B provides an alternative overview of the function of the disclosed MMH system, according to an aspect.

FIG. 3B provides an alternative overview of the function of the disclosed MMH system, according to an aspect. Similarly to the prior disclosed overview of FIG. 3A, the overall MMH system function may be summarized here in FIG. 3B. Data of relevance may be collected as aggregate information 3036, which may be broken down into several subcategories, including individual sources, ecosystem inputs, and evidence-based research. These individual sources may include basic demographic information, activities of daily living (ADLs), personal and family medical history, chief complaints, and range of motion measurements. These individual sources may also include additional biometric exercises that test a patient's gait, strength, and balance. The described ecosystem inputs may include tracked responses from providers to MMH provided possible diagnoses and interventions, as well as learning from cloud based collaborators and partners and learning from results which interventions are most efficacious and which providers deliver superior outcomes. The evidence based research may come in the form of thousands of existing clinical MSK based studies, related to symptoms and interventions, but may also include user specified protocols and primary research using the MMH system's environment for compliance and efficacy of outcomes.

The hereinabove described aggregate information may be formatted into a curated data system 347. The curated data may contain a record of a patient's MSK health over time, and how it compares to the population norms. This curated data may include individual MSK tracking, ecosystem tracking and community sharing. Individual MSK tracking may include a patient's personal range of motion (ROM) measurements, the effectiveness of applied (or prospective) interventions, trending concerns in patient health, as well as potential improvements and gains in a patient's MSK development. The described ecosystem tracking may cover tracked outcomes resulting from applied interventions across all users of a group, as well as leaning which interventions are efficacious for certain injury profiles and body morphologies and identifying symptoms which may signal an injury risk earlier. Finally, community sharing may include aggregated, headless data on clinical and non-clinical interventions to alleviate pain, while also potentially including increased delivery of information on the effectiveness of clinical and non-clinical interventions to providers and individuals.

This curated data may be utilized by a care navigation and assistance system 3048 through the utilization of an open EMR (electronic medical record) which allows curated data to be pulled from the curated data system 3047 to the care navigation and assistance system 3048 and vice-versa. The care navigation and assistance system 3048 may be responsible for performing several tasks relating to patient care, including identifying appropriate service providers, appointment scheduling, tracking patient progress, maintaining a patient pain log, providing an AI coach to assist patients with stretches, exercises, and assessments, providing patient and provider notifications where pertinent, and documenting all relevant information. This information collected within the care navigation and assistance system 3048 may be pushed back into the curated data system 3047 for storage and utilization in future care itineraries. The care navigation and assistance system 3048 may be responsible for facilitating the communication between patients/employees/wellness users, the disclosed EMMA bot of the MMH system and providers to ensure that each party is in proper communication to facilitate proper care protocols are followed.

Figure 4:
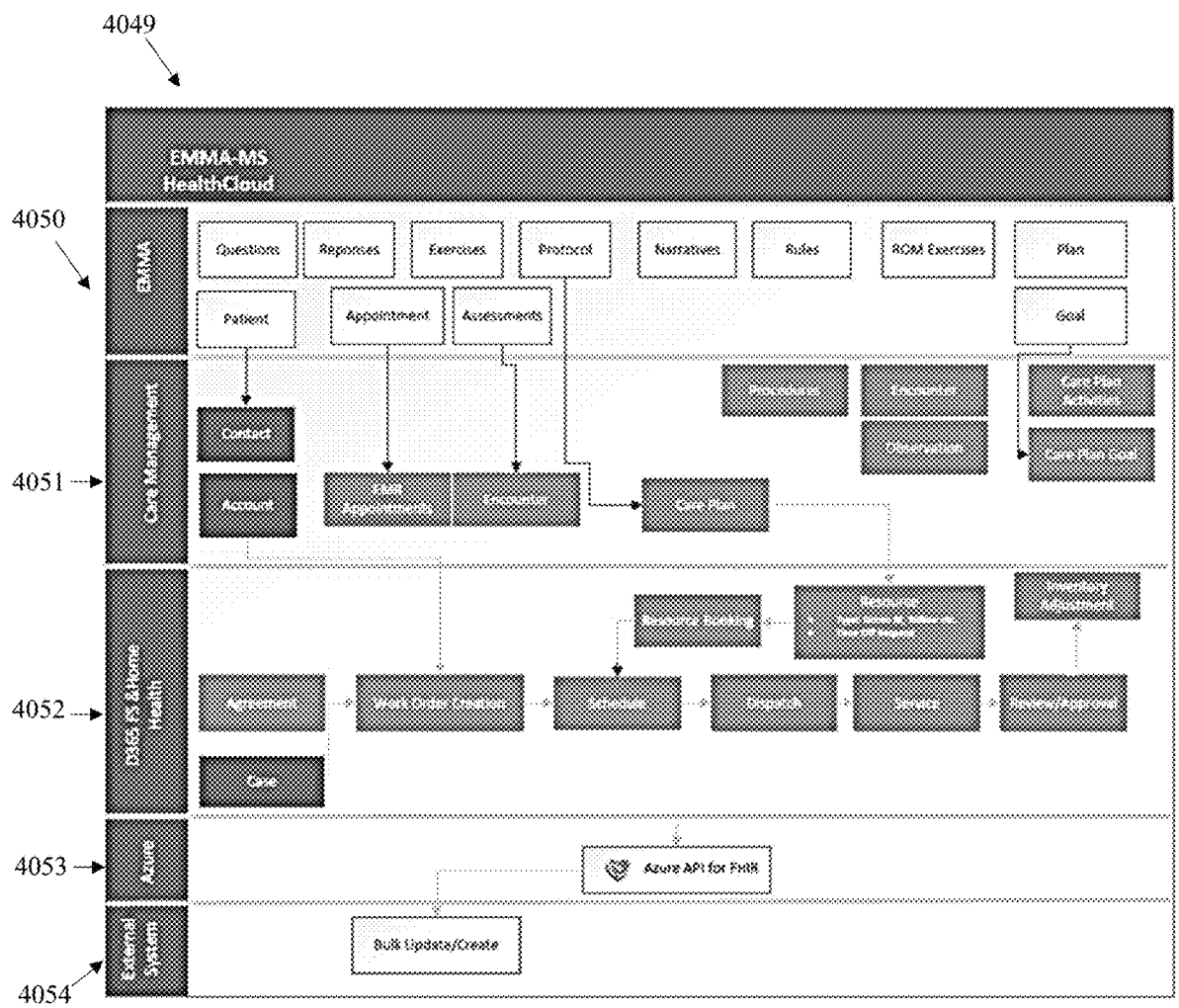
FIG. 4 illustrates the EMMA-MS HealthCloud, according to an aspect.

FIG. 4 illustrates the EMMA-MS HealthCloud 4049, according to an aspect. In order to facilitate proper function of the various elements of the disclosed MMH system, it is necessary for data communication to be established between each appropriate system.

As disclosed hereinabove, the virtual assistant EMMA bot 4050 within the MMH system may be responsible for interfacing with the patient and facilitating many key operations in an effort to supplement patient care. As disclosed herein, the EMMA bot 4050 may be responsible for providing questions to patients, recording their responses and providing exercises and assessments for them to perform. The EMMA bot 4050 may also be responsible for established care rules and narratives, as well instructions for range of motion exercises. The EMMA bot 4050 may engage with the disclosed care management system 4051 in several ways including allowing patients to contact members of the care management system, such as care providers, allowing for the scheduling of appointments, performing assessments that may be used as the basis for a medical encounter, implementation of protocols to establish a care plan, and establishing goals utilized within the care management system.

The care management system 4051 may hold patient account information which may be used by a home health system 4052 to create a work order and the aforementioned care plan, which may be further utilized to determine the resources needed for care by the home health system 4052. The care management system may also include procedures, encounters, and observations relevant to the patient's health and care. Care plan activities may also be stored within this care management system 4051 and used based on the patient's needs.

The home health system 4052 portion of the EMMA-MS HealthCloud may comprise process steps corresponding to the treatment authorization and fulfillment. For a particular health episode, the home health system 4052 may hold information regarding agreement to fulfill and work order creation. Resource booking may be based upon the previously described resource determination made with the care management system, which influences the subsequent scheduling of appointments. Following scheduling, the home health system may also handle dispatch, service and review/approval protocols, while also adjusting inventory based upon the service provided.

All of the above collected information may be collected, processed and pulled through the Azure API for FHIR 4053 for updating/storage of the relevant medical information on an external system 4054. It should be understood that this overview of the EMMA-MS HealthCloud may only include details relevant to the EMMA systems interactions with the MMH system and may omit additional details explored in greater detail hereinbelow.

Figure 5A:
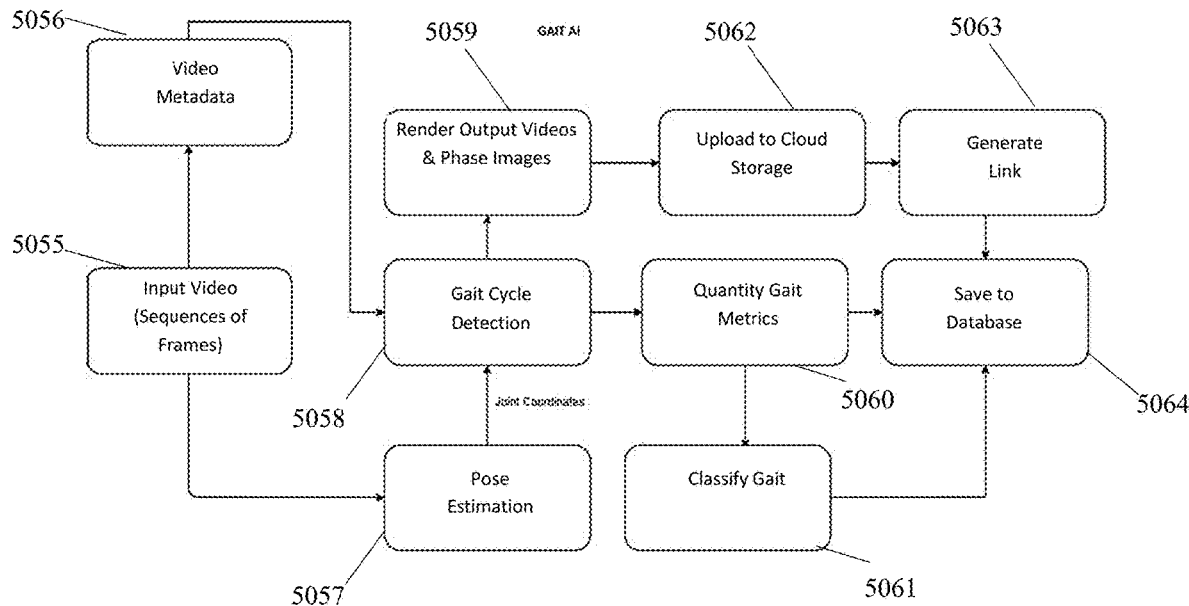
FIG. 5A illustrates the system architecture of a gait API, according to an aspect.

FIG. 5A illustrates the system flow diagram of the disclosed gait API, according to an aspect. In order to provide an accurate diagnosis of patient health, multiple assessments may be performed, in which the patient is monitored and recorded via the camera present on a device. One such assessment may be a gait assessment in which a video of the patient's walk is recorded and analyzed to assess whether or not said patient has a normal or abnormal gait. Such an analysis may prove useful in determining other factors related to gait that may influence a patient's health, particularly those that are neurologic in nature and increase fall risk.

In order to classify gait-based abnormalities, pose estimation techniques were used to quantify different features in normal patterns, and these features were then combined to form a range to classify anomalies. In an embodiment, a clinical team may manually annotate healthy and unhealthy subjects to define the ground truth of the joint angles as well as the range of the features for normal patterns to teach each model how to properly identify the necessary data. Any pattern which falls outside this range by a significant amount may be considered to be an anomaly. The distribution of gender, age, environment, status of the test subjects makes this approach diverse enough to cover most, if not all, types of normal patterns possible.

The system architecture of the gate API may display the process followed by the MMH system to diagnose a normal or abnormal gait in a patient. First, the API may receive a video 5055 from a user, which is stored as a sequence of frames. Video metadata 5056 may be extracted from each of these frames for use in the gait analysis. Following this, the MMH custom trained models (discussed in greater detail hereinbelow) may perform pose estimation 5057 on the sequence of frames to identify the pertinent frames for analysis. At this point, the output of the pose estimation 5057 algorithm (e.g., the coordinates of the predicted joints) and the prior collected video metadata 5056 are fed into a gait cycle detection algorithm 5058. From here, the output videos are rendered, and the images of the important phase images are extracted 5059 and stored. Following phase image extraction, a pose skeleton of the patient may be drawn over each frame of the video to form an output video, from which the gait metrics may be quantified 5060. With the gait metrics quantified, the gait of the patient may have their gait classified 5061 as either normal or abnormal. Lastly, the videos and images are uploaded to the cloud storage 5062 and the link is generated 5063. The link is stored in the database 5064 along with the analysis results.

Figure 5B:
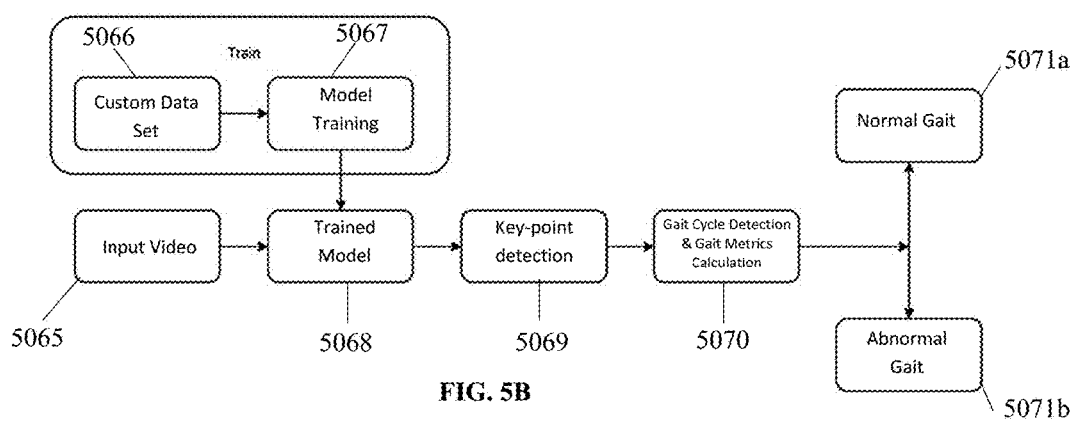
FIG. 5B illustrates a summary of the gait classification method, according to an aspect.

FIG. 5B illustrates a summary of the gait classification method, according to an aspect. An input video 5065 may be provided, comparable to the one produced when quantifying gait metrics 5050 in FIG. 5A, and input into a trained model 5068. This trained model 5068 may be provided by inputting a custom data set 5066 into an untrained model through a model training procedure 5067. The trained model 5068 may process the input video 5065 to produce frames with predicted key points 5069 for the purposes of both gait cycle detection and gait metrics calculations 5070. With this data processed, the gait cycle may be identified as normal 5071*a* or abnormal 5071*b*. This high-level overview of gait classification will be explored in greater detail hereinbelow.

Figures 5C, 5D:
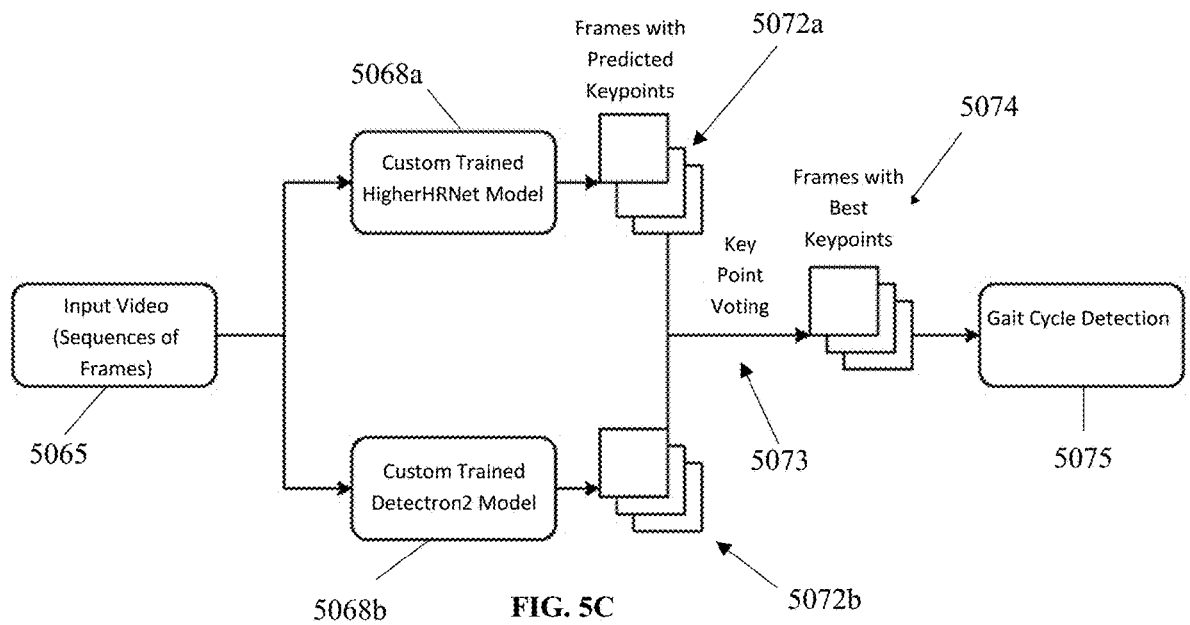
FIG. 5C illustrates a summary process of gait cycle detection using custom trained models, according to an aspect.
FIG. 5D illustrates a chart of the summary data of the two phases of a gait cycle, according to an aspect.

FIG. 5C illustrates a summary process of gait cycle detection using custom trained models 5068*a*, 5068*b*, according to an aspect. The gait cycle detection process illustrated herein may bare similarities to the disclosed gait classification method but may utilize multiple trained models for key point identification. An input video 5065 may be input into two separate trained models: a custom trained HigherHRNet model 5068*a* and a custom trained Detectron2 model 5068*b*. Each of these models 5068*a*, 5068*b*B may predict which frames are the keypoints ("key points") 5072*a*, 5072*b* and collaborate with each other through a process of keypoint voting 5073 to generate a list of frames with the best keypoints 5074. From here, these best keypoints 5074 may be utilized in the gait cycle detection process 5075, as described hereinabove. The usage of two different trained models allows for deficiencies in one method to be compensated for by the other, allowing for better overall keypoint detection, which enhances the accuracy of gait cycle determinations.

In the sequence of consecutive images extracted from a video, the information that is easiest to identify and observe is movement at a specific time. The basic unit of human movement is the movement at the specific instant; however, we do not need all joints to detect a specific, isolated event. From inspecting the sequence of images, the relations between specific body parts, including the shoulder, hip, knee, heel, and ankle joints or the bones associated with specific joints may provide adequate information to detect a specific biomechanical event. Furthermore, such information may be used to distinguish regular movements from abnormal movements, or different kinds of anomalies, as described herein.

In most of the normal movements, joint angles fall in specific ranges depending on the type of movement sequence and relevant joints of interest. Moreover, the signals derived from some joints can strongly represent the movement pattern and information. Detecting the patterns can lead to determining movement cycles and phases within a gait cycle. Research has shown that the movement patterns and variations of each joint angle are relatively cyclic in normal movements. Periodic and symmetric movements are also apparent in normal movement. However, abnormal movements tend to be aperiodic and random. A movement anomaly may also consist of a sequence of normal poses. It has been observed that joint information and the information of consecutive posture taken at each frame together are insufficient in differentiating between normal and abnormal movements. For instance, a patient with pain may have different velocities than the opposite joint or side of the body. Therefore, concatenated feature vectors corresponding to a movement cycle may be used to incorporate the temporal context into the movement evaluation. A movement cycle is assumed as an anomaly if the average movement cycle falls outside of the normal movement cycle.

The proposed system architecture is divided into two phases based on two different approaches for movement cycle detection: an angle-based approach and a keypoint path track-based approach. These are the two approaches from which predictions may be merged. After detecting cycles by using both approaches, a higher level of accuracy may be attained.

In an angle-based approach, on receipt of a video from the front end, the gait detection process is initiated. The video is divided into sequence of frames and pose estimation is done on these frames using the custom-trained models to extract the location of the keypoints. A new matrix is constructed using the best joint coordinates by taking the best prediction on the basis of the comparison of confidence scores for a specific joint prediction by the custom-trained models. The coordinate with the best confidence score for a specific joint or key point is stored in the new matrix which is then fed to the movement detection algorithm. After this procedure, the movement cycle is extracted using these key points which is shown in FIG. 5C above. After the movement detection, the movement is classified as normal or abnormal, as described in FIG. 5B.

In the keypoint path tracking approach, a movement cycle can be detected and determined with the use of signals derived from the various related points of the subjects. In the videos, the subject has to move based on a specific biomechanical movement instruction. These biomechanical movements were selected to evoke a provocative response. Movement points are detected in order to calculate two types of signals: a signal using the difference of the x-coordinate points of specific joints and a signal using the displacement of the joint(s) of the last five frames. As the raw signals may contain outliers and noise, an outlier handling technique and several types of smoothing techniques are performed over these types of signals. Inter quartile range methods may be utilized for discarding outliers, with a defined custom smoothing method and Savitzky-Golay filter to smooth the signals. After performing these techniques at several phases, smoothed signals were produced which may be used for detecting the desired repetitiveness of the signals. After getting the smoothed, usable signals, the movement starting points may be detected. Through the utilization of the recorded movement and starting points, movement cycles, phases, and related metrics may all be determined. While the herein described process may only explicitly cover gait assessments, the methods and techniques utilized in the acquisition of this data may be easily extended to other assessments in which body joint angles are measured, including posture, neck, back, arm and leg assessments, and trained, machine-learned stretches and exercises that involve movement related data capture, analysis, and reporting. Both of the approaches use two-dimensional pose estimation to detect the location of body joints from RGB videos and, as described herein, were successful in creating an objective, rule-based relevance to classify the risk of degenerative musculoskeletal conditions.

FIG. 5D illustrates a chart of the summary data of the two phases of a gait cycle, according to an aspect. In order to determine if an individual has a normal or abnormal gait, it is necessary to identify each known phase of a gait cycle within the captured video frame data. It should be understood that there are eight sub-phases of a gait cycle, including heel strike ("HS"), loading response ("LR"), mid stance ("MST"), terminal stance ("TS"), toe-off ("TO"), initial swing ("IS"), mid-swing ("MSW") and terminal swing ("TSW"). The gait cycle may alternatively be broken down into two phases for each leg: a stance phase, a swing phase, wherein the stride is difference between the consecutive identical gait event for the same leg.

A summary of exemplary times for these phases in an individual's gait cycle may be found in FIG. 5D. Movement Analysis studies the ways human biometric movement is a succession of physical actions involved during prescribed biomechanical tests. Formally, the movement cycle is defined as the interval between two successive occurrences of the same event (e.g., an initial HS and a second HS). In order to illustrate the method used to train the disclosed models to identify and analyze the above phases and sub-phases, exemplary processes are described and illustrated for heel strike analysis within FIGS. 6A-6E and mid stance analysis in FIG. 7A-7E. In addition to the first dataset described in FIG. 6A-7E, which utilized the angle based approach, a second dataset which utilized the keypoint tracking based approach is described in FIGS. 9A-10G.

Figures 6A, 6B, 6C:
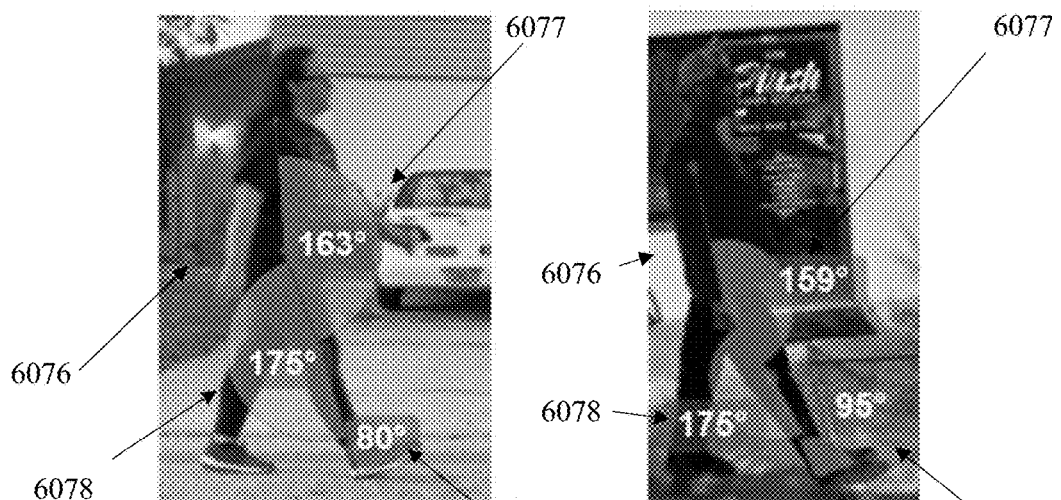

FIGS. 6A-6E illustrate the process of extracting joint angles from heel strike frames, for the angle based approach, according to an aspect. The methods used to train the MMH system to identify and analyze the heel strike phase are disclosed hereinbelow. The process of training a corresponding model may begin with the generation of a data set, which in this case may be joint pose measurements for each of the eight sub-phases of a gait cycle for a plurality of individuals. FIGS. 6A and 6B provide visual representations of heel strike frames that were manually identified from the input video. As can be seen in FIGS. 6A-6B, these frames were manually annotated with the pose angles for the hip, knee, and ankle of each individual 6076. The information of FIG. 6A-6B is summarized in FIG. 6C, and further utilized to calculate the flexion/dorsiflexion angle or extension/plantar-flexion angle (depending on which is present) for the hip, knee and ankle of each individual 6076. The calculations of FIG. 6C (provided in degrees) provide an insight into how close the individual's pose is to an average, normal pose for that particular gait phase when compared to the values calculated for a normalized group.

From the clinical perspective, two methodologies are constructed herein to identify the presence of a normal or abnormal gait. The first way this was accomplished, described as an angle based approach hereinabove, was done by referencing known values of the range of motion of the joints of the lower extremity at the different phases of gait. In order to reliably identify each necessary gait phase, it may be necessary to film gait cycles at 60 frames per second. By maintaining a suitably high frame rate, each gait phase may be successfully identified and differentiated from other gait phases. To produce the appropriate information for training the utilized model, a clinical team may stop the input video at the precise frame of the intended phase of gait and then measured the hip, knee, and ankle ranges of motion using Kinovea and a manual goniometer, and manually annotated the ROM measurement for these respective joints for each gait cycle and provided this information to a clinical and AI team to teach the characteristics of a normal gait to a model.

The durations of the two phases of gait; the stance phase and the swing phase, were also manually measured to provide professional, manually generated phase durations to teach the model and compare with the API generated results. As is understood, the stance phase on average represents approximately 60% of the gait cycle and the swing phase on average represents approximately 40% of the gait cycle (with regards to time span). For test subjects having normal gaits, it was found that when measured correctly, each phase fell +/−10 percent of these values. Using the herein disclosed set-up, a video of a patient's gait may be analyzed according to this specific protocol to determine whether their gait is normal or abnormal. This may be done by recognizing whether a test ROM falls into a range of normal ROM values at the various phases of a gait and further verifying that their percentage of stance phase length relative to swing phase length are within established normal limits (+/−10 percent of 60% and 40 percent, respectively).

It is evident that the gait event depicted in FIGS. 6A-6B falls under the heel strike category as the heel of each individual's right foot has just touched the ground after being swung. The joint angles, which were manually annotated using an annotation tool, such as Kinovea, are displayed over each figure and positioned by the proper joint, accordingly. Alternative manual annotation tools may also be utilized. The values of the angles at the hip 6077, knee 6078, and ankle 6079 are 163, 175 and 80 degrees, respectively, in FIG. 6A and 159, 175 and 95 degrees, respectively, in FIG. 6B. If a hip angle is less than 180 degrees, then it is a hip flexion, whereas if a hip angle is more than 180, it is a hip extension. The flexion/extension value is obtained as the absolute difference from 180. The same is utilized for the knee angle as well, which may be described as knee flexion or knee extension, accordingly. For an ankle angle that is less than 90 degrees, said angle is presented as an Ankle Dorsiflexion, whereas for an angle greater than 90 degrees, said angle is presented as an Ankle Plantarflexion. As such, both Flexion/Dorsiflexion and Extension/Plantarflexion cannot occur at the same time for a joint. A neutral value may be obtained for a hip 6077 or knee 6078 angle of 180 degrees or an ankle 6079 angle of 90 degrees.

From the angles illustrated in FIG. 6A-6B, the flexion or extension of the hip, knees, and the dorsiflexion or plantarflexion of the ankle may be calculated. FIG. 6C shows the calculation process, which describes that the hip flexion is 17 degrees, and the knee flexion is 5 degrees, and the ankle dorsiflexion is 10 degrees for the heel strike phase depicted in FIG. 6A and the plantarflexion is 5 degrees for the heel strike phase depicted in FIG. 6B. Using heel strike frame videos of individuals with normal gaits from a teaching dataset, rules for heel strike phases have been generated from the angles, and the flexion, or extension of the applicable limbs. The data collected from the normal gait videos are shown in FIG. 6D. As stated hereinabove, extension and flexion cannot happen for the same joint at the same time (e.g., when there is hip flexion, there is no hip extension and vice-versa). The same can be said for knee flexion and extension, and ankle dorsiflexion and plantarflexion. The term "none" is used in values in which no flexion or extension is seen. This method of manual rule generation may be performed through manually taking these measurements for each gait phase using the appropriate video frames.

In the first column of the table in FIG. 6D, the ID of the model or subject for the gait video is mentioned, where G represents the exercise known as gait. The next three digits are the ID of the patient, and the last two letters, "HS" represent heel strike. The rule generated for the gait event known as heel strike is summarized in FIG. 6E, where the hip has to have a flexion of 5-42 degrees, the knee has to have between 30 degrees of flexion and 9 degrees of extension, and ankle must between 21 degrees of dorsiflexion and 5 degrees of plantarflexion, for the gait event for the specific frame to be classified as a heel strike. Another parameter that is also essential for a gait event to be heel strike is the distance between the ankles, which must be close to the maximum for that gait cycle, as will be described in greater detail hereinbelow.

FIG. 7A-7E illustrate the process of extracting joint angles from mid stance frames gait phases, according to an aspect. It is evident that this gait event depicted in FIGS. 7A-7B falls under the mid stance ("midstance") category as the right foot of the subject 7076 is totally on the earth in the vertical position and the left foot is about to go for a swing, as mentioned in the previous subsections. Similarly to FIGS. 6A-6B, the angles depicted in FIGS. 7A-7B were manually annotated using the annotation tool Kinovea, but may also be annotated by utilizing alternative annotation tools instead.

Figures 7A, 7B, 7C:
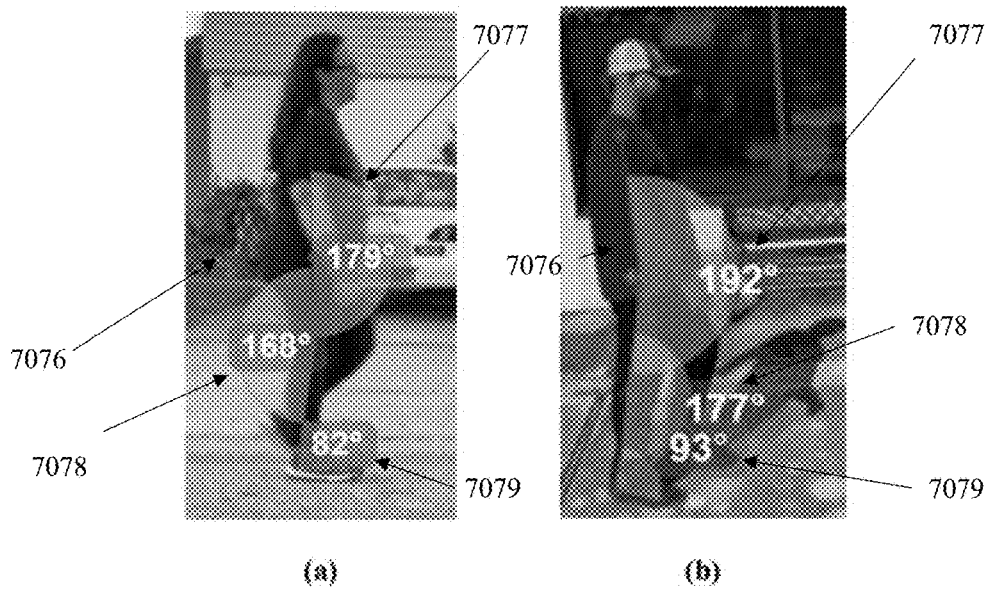

From the angles illustrated in FIG. 7A-7B, the flexion or extension of the hip, knees, and the dorsiflexion or plantarflexion of the ankle may be calculated. In FIG. 7A, the hip has 1 degree of flexion 7077, the knee has 12 degrees of flexion 7078 and the ankle has 8 degrees of dorsiflexion 7079. In FIG. 7B the hip has 12 degrees of extension 7077, the knee has no extension 7078 (180−177=3 degrees of flexion) and the ankle has 3 degrees of plantarflexion 7079. Rules for midstance from the angles, and the flexion, or extension of the limbs using the gait videos of the normal subjects from the learning dataset were generated accordingly. Said data is provided in FIG. 7D.

In the first column of the table in FIG. 7D, the ID of the model or subject for the gait video is mentioned, where G represents the exercise known as gait. The next three digits are the ID of the patient, and the last two letters "MS" represent Midstance. The rule generated for the gait event known as Midstance is summarized in FIG. 7E, where the hip must have between 19 degrees of flexion and 12 degrees of extension, the knee must have between 25 degrees of flexion and 3 degrees of extension, and the ankle must have between 16 degrees of dorsiflexion and 4 degrees of plantarflexion for the gait event for the specific frame to be classified as Midstance.

As described hereinabove, the process outlined for the angle data acquisition and rule generation for the heel strike and midstance phases described hereinabove may be suitably repeated for the other sub-phases of the gait cycle, to assess the normality or abnormality of a gait cycle. As noted hereinabove, each abnormal gait cycle identified is not "taught" to the system, but simply analyzed to determine if it would be identified as abnormal.

It should be noted that overlaps in the ranges of the four sub-phases measured was observed during rule generation. In response to this, a distance based rule was implemented, to incorporate alongside the angle ranges to help classify the gait phase.

As described in greater detail hereinbelow, the Gait API initializes the gait analysis process after the video has been stored for analysis in the server/database. When the process is triggered, the pose estimation process is triggered to estimate the locations of the key points throughout the whole video to find out the maximum, and minimum horizontal and vertical, ankle distances of the gait sequence of the filmed individual. For the described distance-based rule, a threshold is set for a phase to be classified as a candidate for heel strike. Said threshold requires a minimum of 70% of the maximum horizontal ankle separation (e.g., step length) to also be satisfied alongside the angle based manual rules we had established hereinabove. When the heel strike candidate frames are extracted, the frame with the maximum step length is to be classified as the frame having heel strike. In the case of the mid stance and mid swing gait phases, the horizontal distance between the ankles should be close to the minimum, which should be at most 20% of the maximum horizontal distance between the ankles.

Figure 14:
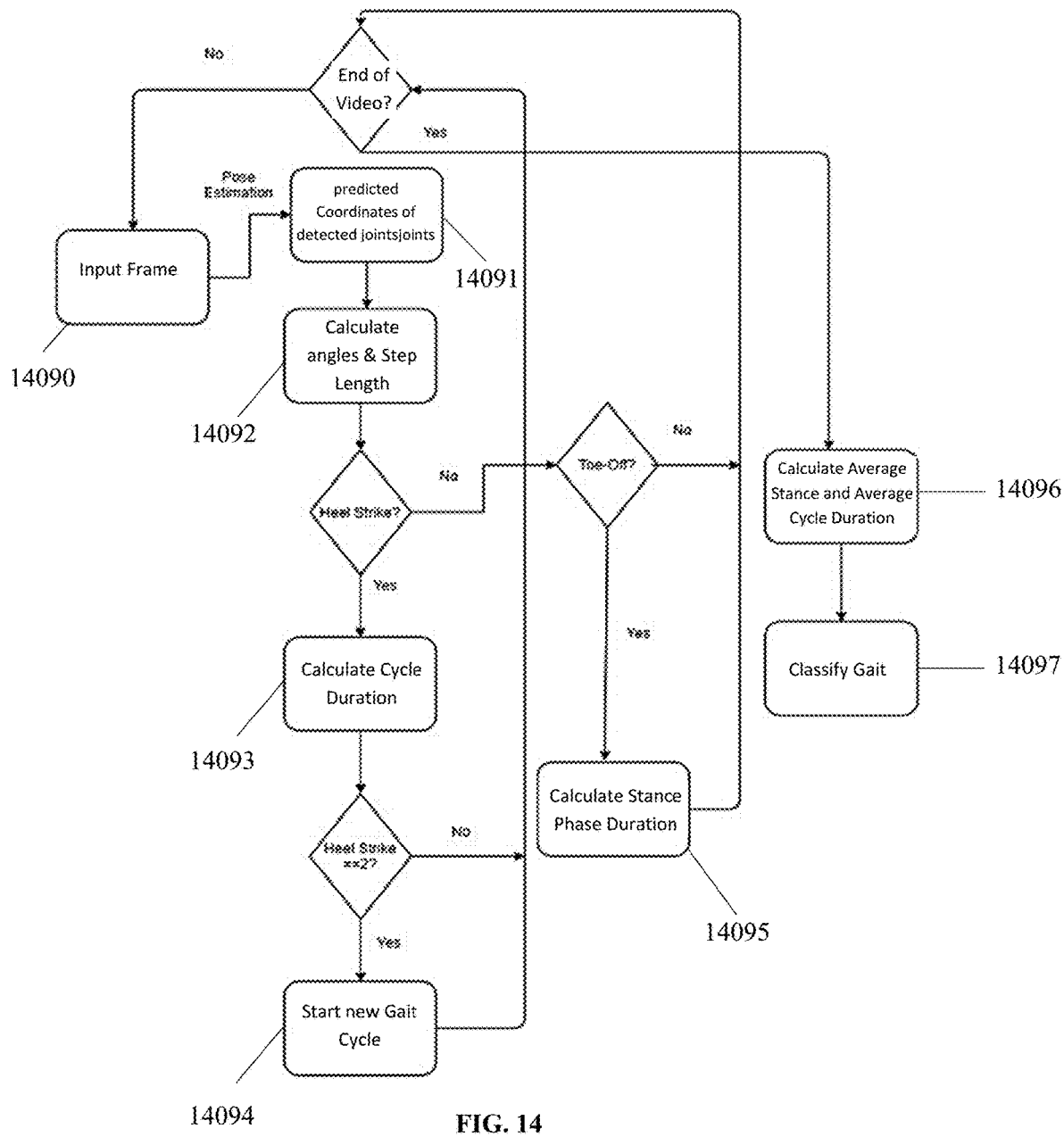
FIG. 14 illustrates the disclosed gait classification algorithm, according to an aspect.

The range established for the distance-based rule for the toe-off phase is between 20% to 70% of the maximum horizontal distance between the ankles. Thus, overlapping sub-phases of a gait may be differentiated based upon the distance between the ankles. These ranges and thresholds were determined after conducting rigorous analysis on the videos of the normal gait videos in the learning dataset. The API was utilized while using these different thresholds and ranges, and it was found that the mentioned rules work best in detecting the gait phases when combined with the manual rules for the flexion, and extension derived from the angles. The combined approach of the manual rules of flexion, and extension along with the step length is illustrated in FIG. 14.

FIG. 8 illustrates a summary of the manually generated rules for heel strike, midstance, toe-off, and mid swing phases for the angle based approach, according to an aspect. From the hereinabove described process of manually annotating frames to teach the machine learning algorithm model the accepted joint ranges for each of the phases of a walk cycle, rules may be generated to identify further input gait cycles as either normal or abnormal. Identification of the normality of a gait cycle may account for not only the angle of each joint during a pose, but also the time duration of a phase (swing phase, stance phase) of a phase, which will be described in greater detail hereinbelow.

FIGS. 9A-9D illustrate the process of refining ankle separation data for utilization in the keypoint path track-based approach, according to an aspect. In the disclosed manual rule generation process of FIG. 9A-9D, rather than immediately identifying the angles between joints to determine the normative status of an individual's gait cycle, the keypoint path track method utilizes information such as the distance between the individuals left and right ankle, and the velocities of the left and right ankle to identify the frames of interest from an input video. This is possible due to the patterned, cyclical nature of a gait in which each heel's disposition with regards to the other heel directly reflects which pose the individual is currently in. For example, when an individual is walking and their heels are maximally separated, the user is likely be in a heel strike pose.

As mentioned hereinabove the algorithm may make use of the distance between an individual's left and right ankles in determining which frame of the raw data contains a specific pose of a gait cycle. The horizontal distance between the left ankle and the right ankle follows a pattern during a gait cycle. That is, when any individual does a heel strike, the horizontal distance between their left ankle and right ankle reaches a maximum value for a gait cycle. With the horizontal distance between the left ankle and the right ankle at its maximum value at the time of heel strike, this horizontal displacement decreases to zero, and then again increases to the maximum when the next heel strike occurs. As such, a list of values of the horizontal distance between the left ankle and the right ankle may be analyzed to find the maximums of this list, which, as established previously, are the heel strike moments. As disclosed hereinabove, there are two phases in the gait cycle for each leg: a stance phase and a swing phase. While walking, one leg becomes static for some time and then it starts moving (swinging). When a primary leg becomes static, the secondary leg moves. Therefore, the starting point of one leg being static can be considered as the starting point of swing phase of the other leg.

In order to perform this analysis, first, each frame must be extracted from a provided raw video. Then, each frame may be input into the keypoint detection model (such as HigherHRNet) to extract the keypoints from that particular frame. A list of points is formed by appending the keypoints for all the frames in a video. Three feature signals may be calculated from these keypoints: A difference of the ankles in x-axis (fs1), the speed of left ankle (fs2) and the speed of right ankle (fs3). In order to measure the difference of the ankles on the x-axis, first, the raw signal of the difference in ankles in x-axis is captured using equation (1), ankle_difference=|left_ankle.x−right_ankle.x|. A sample raw signal is depicted in FIG. 9A.

From the raw signal captured by equation (1), the signal is smoothed using a custom defined procedure of one-degree smoothing. In one-degree smoothing, for any value from the signal, it is checked if the value is between its adjacent values in the signal. If this condition is satisfied, the value is kept in the resultant smoothed signal. If this condition is not satisfied, the average of the adjacent values is used to replace the value in the smoothed signal using equation (2), raw_signal[i]=(raw_signal[i−1]+raw_signal[i+1])/2. In FIG. 9B, the state of the raw signal after performing 1 degree smoothing is shown. This resultant smoothed signal may be utilized as the input signal for two-degree smoothing. In two-degree smoothing, for any value from the signal, it is checked if the value is between the average of the previous two values and the average of next two values. If this condition is satisfied, the value is kept as it is. If this condition is not satisfied, said value is replaced with the average of the average of the previous two values and the average of the average of next two values, which is defined by equation (3), raw_signal[i]=((raw_signal[i−2]+raw_signal[i−1])/2+(raw_signal[i+1]+raw_signal[i+2])/2)/2. In FIG. 9C, the state of the raw signal after performing 2 degree smoothing is shown.

Figure 9D:
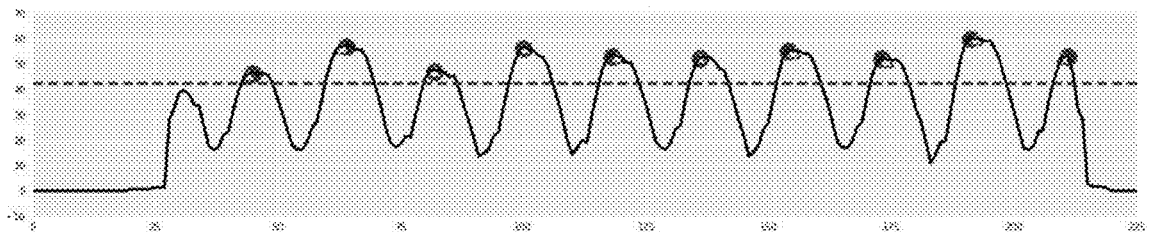

Following this 2-degree smoothing, heel strike detection may begin. As described previously, only frames in which the displacement between the two ankles is greater than 70% of the maximum may be assessed as a potential heel strike frame. A peak finding algorithm, such as find_peaks( ), which is provided in Python scipy.signal module, may be utilized to this end. This function takes a 1-D array and finds all local maxima by simple comparison of neighboring values. A minimum horizontal distance threshold of 10 values between peaks was utilized to ensure that no two peaks were in between 10 adjacent values in the given signal. As can be seen In FIG. 9D, the human expert detected heel strikes detected by human experts were indicated by the triangular point while and the heel strikes found by the system has been graphically shown by circular points. As can be seen, these algorithm-identified heel strikes are exceptionally close to their human expert identified counterparts.

FIGS. 10A-10G illustrate the process of refining left ankle speed data for utilization in the Keypoint Path Track-based Approach, according to an aspect. As described above, in addition to measuring the displacement between the left and right ankle, the Keypoint Path Track-based Approach may also utilize the speeds of the left and right ankle in identifying which frames contain the gait phase of interest.

For the herein disclosed description, the term orientation refers to whether the subject is moving left to right or right to left in the raw video. As subjects in the learning dataset walked and their lateral views were recorded through a video camera, it is only possible to view either their left lateral side or their right lateral side. It should be noted that there are no frontal or rear oriented videos utilized in the disclosed dataset, but alterations to the disclosed process and algorithms may also be utilized to make use of such videos. The described walking procedure outlined herein for the gait assessment may also be referred to as a gait procedure. In the disclosed embodiment, Detectron2 keypoints may be utilized to identify the coordinate points while comparing the relative positions of the ear and nose to determine the individual's orientation. If an individual's nose points toward the right side of the identified ear point, then the person is walking left to right, and vice versa. If the person is walking left to right, then the right lateral view of the person is clearly visible in the camera. In this case, the right leg is considered as the primary leg (and the left leg is considered as the secondary/non-primary leg) for our calculation.

The first heel strike made by the right leg may be utilized as the beginning point for signal processing or calculation for the speed of the ankles. Calculations may be ceased at the last heel strike made by the primary leg. Similarly, if the person is walking right to left, then the left lateral view of the person is visible, and calculations may begin, and end based on the heel strike of the left leg. In short, if the orientation is set to the left, start from the first heel strike of the left leg and stop at the last heel strike of the left leg. Otherwise, if the orientation is set to the right, start from the first heel strike of the right leg and stop at the last heel strike of the right leg. Once the raw signals for fs2 and fs3 have been captured, they may be processed for swing start detection in the manner described hereinbelow. This process may start by calculating a speed from the index where the first heel strike of the primary leg has occurred and repeatedly calculating this speed until the index where the last heel strike of the primary leg occurred.

The indices before the first heel strike and after the last heel strike are filled with value 0, and thus are not included as part of the calculation. The other values at other indexes are calculated as the distances passed in the last five frames by looking at the x-coordinate value of the current frame and the x-coordinate value from the frame which was five frames back. The difference between the x-coordinate of the ankle of the current frame and the x-coordinate of the ankle from five frames back is used as the value in the signal. This may be calculated using equation (4) (left_speed=|left_ankle.x[i]−left_ankle.x[i−5]|/5) for the left ankle and equation (5) (right_speed=|right_ankle.x[i]−right_ankle.x[i−5]|/5) for the right ankle. In said equation (4), left_ankle.x[i] is the x-coordinate of left ankle point at i-th frame and left_ankle.x[i−5] is the x-coordinate of left ankle point at the frame which was five frames back from the i-th frame. Right ankle speed may be calculated similarly.

Figure 10A:
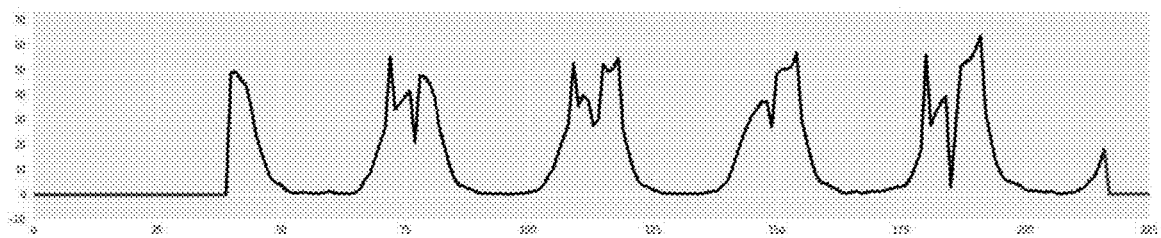
FIGS. 10A-10G illustrate the process of refining left ankle speed data for utilization in the Keypoint Path Track-based Approach, according to an aspect.
Figure 10B:
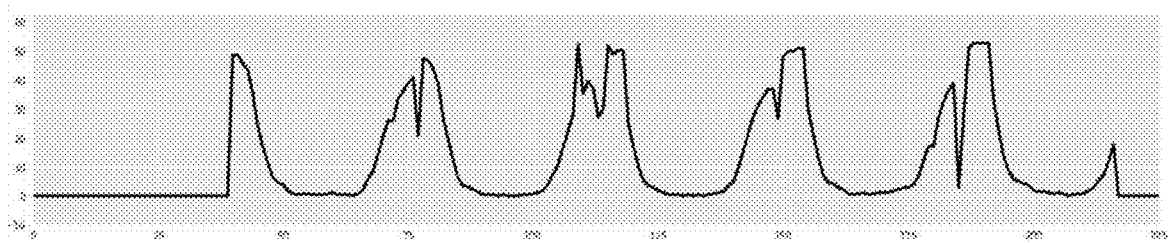
Figure 10C:
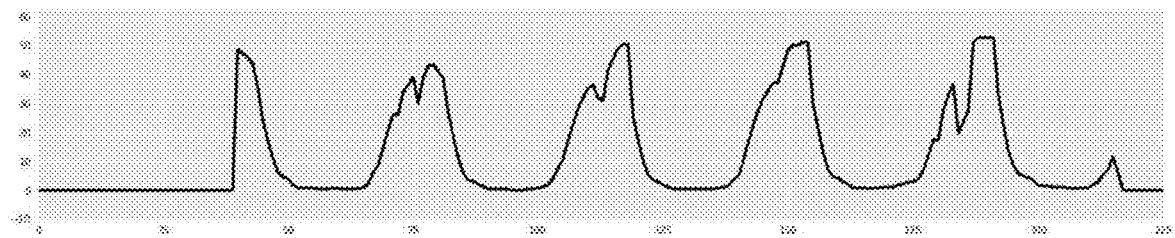

A sample calculation for the left ankle speed (fs2) is depicted in FIG. 10A. We call the result of this calculation a speed signal, as the distance we calculate, and the speed of an ankle are proportional because we have to divide the distance by the time passed in five frames in order to calculate this speed signal. Furthermore, the time passed in five frames is constant for any contiguous five frames for any video as the fps (frames per second) is consistent throughout each collected video. The perimeter portions of the signal (corresponding to before the first heel strike of the primary ankle and after the last heel strike of the primary ankle) are discarded as disclosed previously. After the initial calculation of the speed signal, there may be outliers due to the instability of the camera, misprediction of the body keypoints etc. As such, the interquartile range of the signal is then calculated, and the identified outliers are discarded. If any value is regarded as an outlier, it may be replaced by the value at the previous index of the signal. An example of the signal after discarding the outliers is shown in FIG. 10B.

Figure 10D:
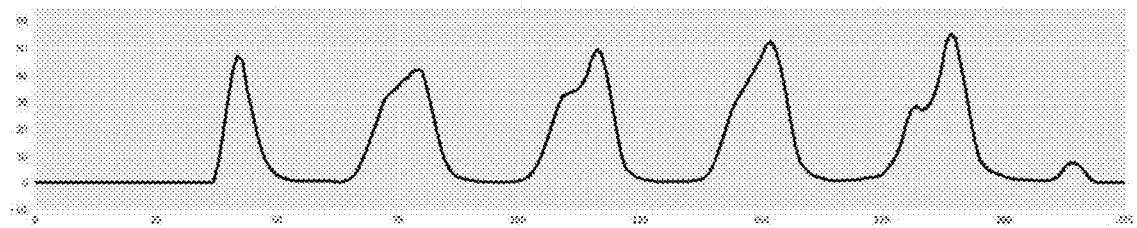

Following the removal/replacement of outliers, smoothing of the signal is required, as the signal now contains noises which makes it difficult to find a proper pattern within gait cycles. A custom smoothing method and a Savitzky-Golay filter may be used to denoise and smooth the signals as described hereinabove. The phases of the smoothing process are described hereinbelow. After discarding the outliers, the signal may be smoothed with the custom 1 degree and 2 degree smoothing methods outlined previously and shown in FIG. 10C. The output after this phase, wherein a Savitzky-Golay filter is used to smooth the signal to a better level. A Savitzky-Golay filter is a digital filter that can be applied to a set of digital data points for the purpose of smoothing the data, to increase the precision of the data without distorting the signal tendency. A python module scipy.signal may provide the function "savgol_filter" to implement this filter. There are parameters that can be tuned in the function disclosed savgol_filter hereinabove. For example, a filter window length of 9 and a $3^{rd}$ order of polynomial may be used to fit the samples, wherein these are the two hyperparameters allowed in scipy.signal.savgol_filter function. The output after using Savitzky-Golay filter is shown in FIG. 10D.

Figure 10E:
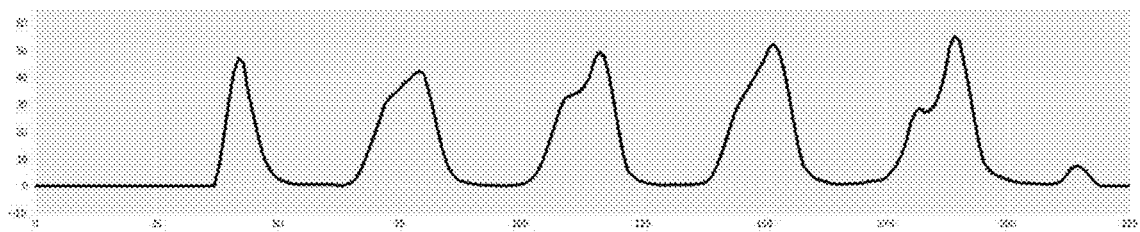
Figure 10F:
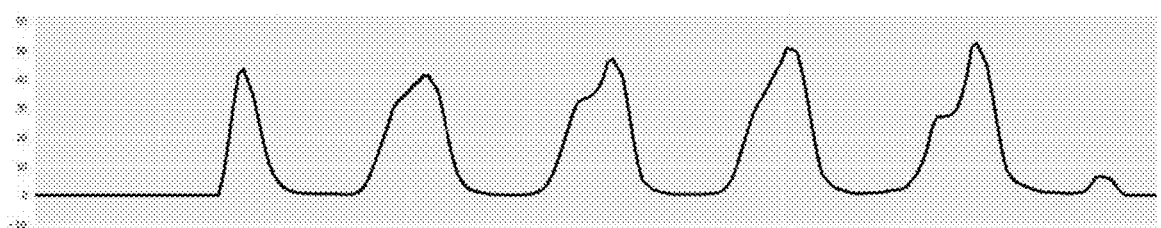

As the Savitzky-Golay filter smooths the signal using interpolation technique, there may be negative values in the smoothed signal. To avoid using these negative values, said negative values may be replaced with a value of 0. An example after discarding the negative values in this phase is shown in FIG. 10E. After the hereinabove processes are completed, the signal may again be smoothed with the prior disclosed custom 1 degree and 2 degree smoothing. As a result of the above processing, a smoothed signal of the speed of the left ankle is generated, as seen in FIG. 10F. This process may be performed for both the left ankle and the right ankle to get corresponding speed signals for the left ankle and right ankle. FIG. 19 is an example of the final output after the above steps are performed for a fs2 calculation. In the overall procedure described above, the samples and states for different phases for fs2 are illustrated. The procedure for calculating the speed of the right ankle (fs3) is much the same as the process for calculating fs2 and most of the corresponding phases for fs3 may be calculated in parallel with fs2 for a system.

As disclosed hereinabove, there are two phases in a walking cycle for any leg: the stance phase and swing phase. During a gait, a leg becomes static for some time and then it starts moving. When the primary leg becomes static, the secondary leg moves/swings, so the starting point of one leg being static can be considered as the starting point of swing phase of another leg. Hence, the starting point of the swing for the opposite leg may be determined by using the speed signal of the primary leg. In the smoothed signal for speed shown in FIG. 10F, there is clearly a visible pattern of an ankle moving and then being static for a time. The speed value on each speed graph moves up and down, then becomes static (nearly zero line) for some time, and then again moves up, and so on.

Figure 10G:
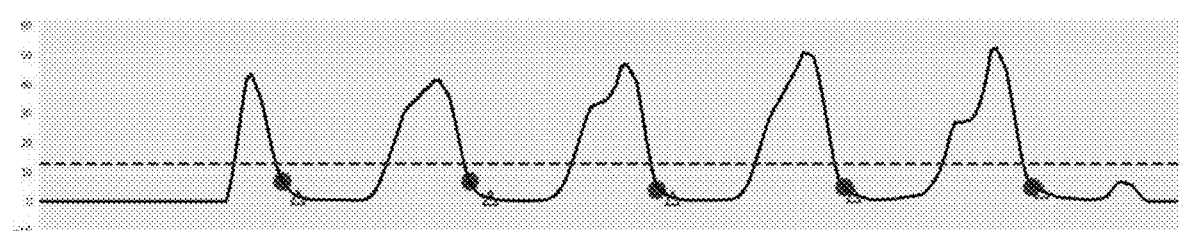

The start of the swing for the opposite leg may be identified by detecting the point where the signal starts to remain static for some time after moving downwards from the peak speed. For this, a threshold for determining a zero region (where speed considered to be zero) may be identified. This threshold may be considered as 25% of the range between the minimum value (no movement) and the maximum value (top speed) of the signal. In other words, any speed value below 25% of the maximum value of the signal may be regarded as speed of 0. This may be done by finding the index where the next 4 speed values are below the threshold and the previous value is above the threshold of 25% of the maximum speed value. Hence, the starting point of the primary leg being static may be locating by identifying where a zero region speed is achieved. FIG. 10G demonstrates the graphical representation of swing start indices for the opposite leg for fs2, wherein the circles are the predicted start indices determined by the system, and the triangles are the indices determined by a human expert. As can be seen the API estimated values do not deviate significantly from the expertly determined ones.

Figure 11:
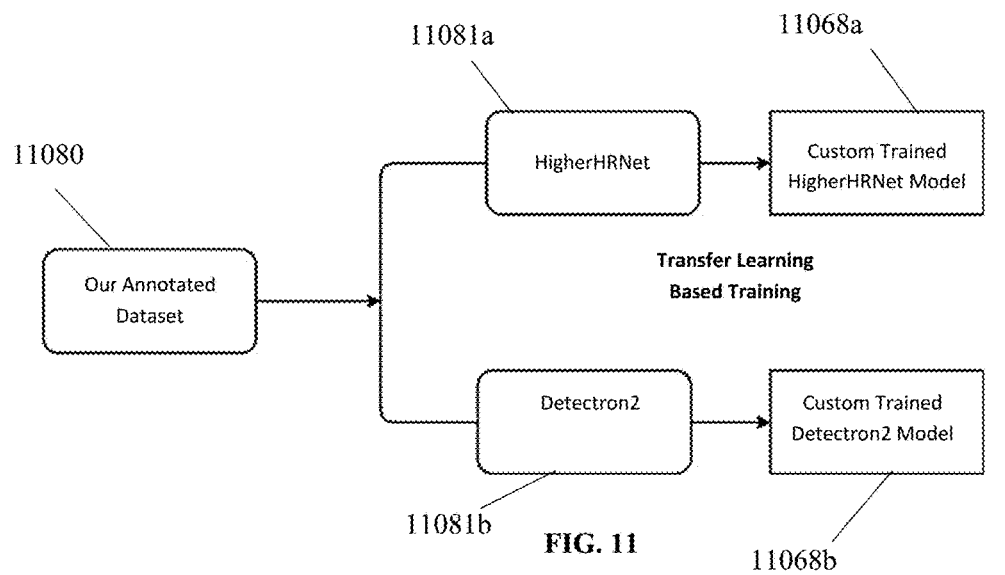
FIG. 11 illustrates the transfer learning based model training process, according to an aspect.
Figure 12:
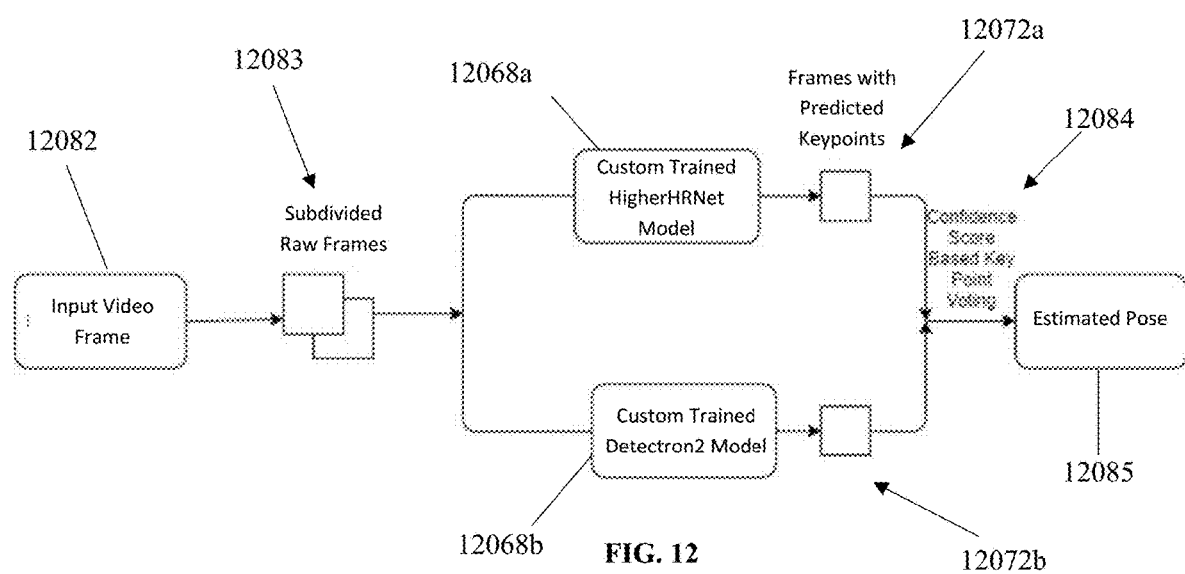
FIG. 12 illustrates the pose estimation process on an input video frame according to an aspect.
Figure 13:
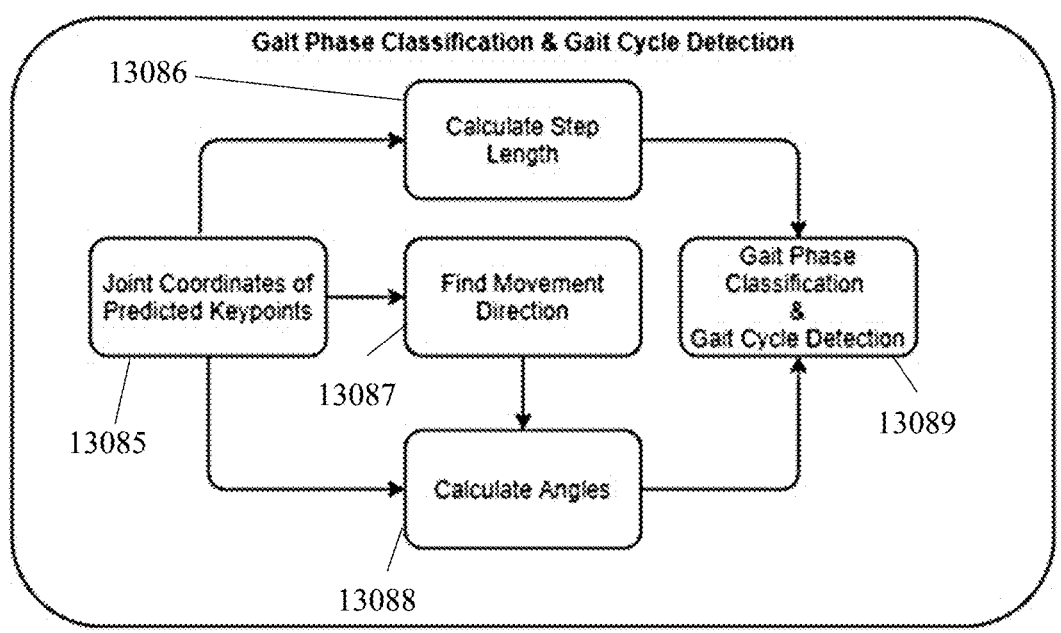
FIG. 13 illustrates the gait phase classification and gait cycle detection process, according to an aspect.

FIG. 11 illustrates the transfer learning based model training process, according to an aspect. FIG. 12 illustrates the pose estimation process on an input video frame according to an aspect. FIG. 13 illustrates the gait phase classification and gait cycle detection process, according to an aspect. FIG. 14 illustrates the disclosed gait classification algorithm, according to an aspect. "Pose Estimation" is a method to detect human figures in visuals using computer vision techniques. In Human Pose Estimation, this technique is used to locate the different joints of the body in images or videos. For gait analysis, such a technique can be useful for analyzing gait videos to remove the need for sensors. The location of the body joints at different points of time in gait videos can be considered particularly important spatiotemporal features. Pose Estimation may be used to detect specific key points of a person's body that are relevant to the assessment being performed. These key points may include an individual's nose, eyes, ears, shoulders, hips, knees, ankles, etc.

There are different types of Pose Estimation, including Openpose, HigherHRNet. In a disclosed embodiment, a custom-trained HigherHRNet 2D Pose Estimation model 11068a, and custom trained Detectron2 11068b may be used for model training using Transfer Learning. 2D pose estimation simply estimates the X and Y coordinates (and a corresponding confidence score) for each key point. These points may be utilized to measure the dorsiflexion, plantarflexion, and extension of the relevant hip, knee and ankle along with the angles at these vertices. Also, some other different measurements of the person's body may be taken such as the difference between the two ankles (both vertical and horizontal), as disclosed previously.

The workflow for the training procedure of the Pose Estimation can be summarized using FIG. 11. Using an annotated data set 11080, the models 11081a, 11081b (e.g., the HigherHRNet model 11081a and the Detectron2 model 11068b) may be trained to identify the keypoints relevant to the pertinent assessment, such as those mentioned above, to produce the custom trained HigherHRNet model 11068a and the custom trained Detectron2 model 11068b disclosed hereinabove, respectively. The custom-trained models 11068a, 11068b are used for pose estimation to extract the coordinates of the detected joints, along with their confidence scores. A new matrix is constructed using the best joint coordinates by taking the best prediction on the basis of confidence scores for a specific joint prediction by the custom-trained models. The coordinate with the best confidence score for a specific joint or key point is stored in the new matrix which is then fed to the gait detection algorithm.

As can be seen in FIG. 12, each video input video frame 12082 of the input video may be taken and subdivided into two frames 12083 wherein each frame is to be fed into a different custom-trained models 12068a, 12068b. These models return the predicted key points coordinates of the body for that frame 12072a, 12072b with an associated confidence value. Thus, the best key points for each joint, based on the confidence score for those key points, are returned by the custom-trained models. Finally, the estimated pose 12085 is provided by the selection based on key point voting using confidence score 12084.

As can be seen in FIG. 13, the process of gait phase classification and gait cycle detection 13089 may continue with the joint coordinates of the predicted keypoints 13085, which may be used to calculate step length 13086, find the movement direction 13087 and calculating joint angles 13088. With these pieces of information determined, the gait phase may be classified, and the gait cycle detected as disclosed herein.

The gait cycle extraction process requires several key steps including checking direction of walking, checking valid changes to specific joint coordinates in gait depending on the direction of walking to filter out incorrectly detected joints, matching horizontal and vertical distances with the thresholds and detecting different phases of gait based on all the parameters. To detect the direction of walking, the abscissa of the hip point was kept track of to determine whether it was increasing or decreasing (which direction it was moving). After that, the coordinates of that specific point were checked in the previous, current and some future frames to filter out the incorrectly detected joints.

A percentage of the horizontal distance between the ankles was taken as a parameter to correctly detect gait events specific to gait cycle detection. It was found that people have a 70 percent threshold for the horizontal distances and 40 percent for the vertical distance of their maximum step length. If these measured differences satisfy this threshold, then that frame is to be considered for heel strike. In an embodiment, the classification of the gait phases was done based on the angles at the hip, knee, and the ankle, and the step length specific to the heel strike. Two consecutive heel strikes of the gait of a person was considered the beginning and end of that gait cycle. Otherwise, that gait cycle was not taken into calculation for average gait cycle calculation (e.g., incomplete gait cycles were not utilized).

The algorithm followed by the disclosed MMH system in determining whether a gait is normal or abnormal is depicted in FIG. 14. Starting from an input frame 14090, the predicted coordinates of detected joints 14091 may be identified through pose estimation as disclosed hereinabove, through the usage of a trained model. With the joint coordinates identified, the joint angles and step length 14092 may be easily calculated. If the joint angles are identified as those consistent with a heel strike, the gait cycle may be calculated 14093 accordingly. If the heel strike detected is a second heel strike, the AI may start a new gait cycle and assess whether the current frame is the last in the input video. If the frame is not a heel strike, it must then be assessed to determine if it contains a toe-off or not. If the frame does contain a toe-off pose, the stance phase duration may be calculated 14095, and the AI may assess whether the current frame is the last in the video. If the frame is determined to be neither a heel strike nor a toe off, the AI may assess whether the current frame is the last in the video. If at any point the assessment of the video determines that there are still additional frames in the video, the process may begin again from the input frame 14090 step. If at any point the assessment of the video determines that no additional frames are in the video (e.g., the current frame is the last frame), the process may continue by calculating the average stance time and average cycle duration 14096 and using said information to classify the recorded gait 14097, accordingly.

There are different types of techniques that may be applied to solve a recognition problem during gait assessment, as well as the other disclosed assessments. In one such technique, described hereinabove as template matching, features to a certain range are employed to model it to a specific gait event. After analysis of a sample dataset, it was found that angles for different phases of the normal gait fall under a range without being biased towards the age, or gender of the subject. This being said, some of the phases of gait may have overlaps between them. This overlapping problem was solved partially by taking distances between the ankle into consideration. Even with this consideration, some overlapping existed between the analyzed phases. Thus, it was decided to consider the interval between the two consecutive heel strikes as a basis of the detection of the gait cycle. It was also decided to make the toe-off phase of the gait cycle the detection point of the end of the stance phase. By taking this approach, the stance and swing phases were differentiated while also finding the duration of the stance and swing phases. By calculating the average duration of the stance and the swing phases, it was possible to classify normal and abnormal gaits. If the stance phase deviated from the standard stance phase duration of 60% of the gait cycle by 10 percent, then said gait would be classified as abnormal.

Figure 15:
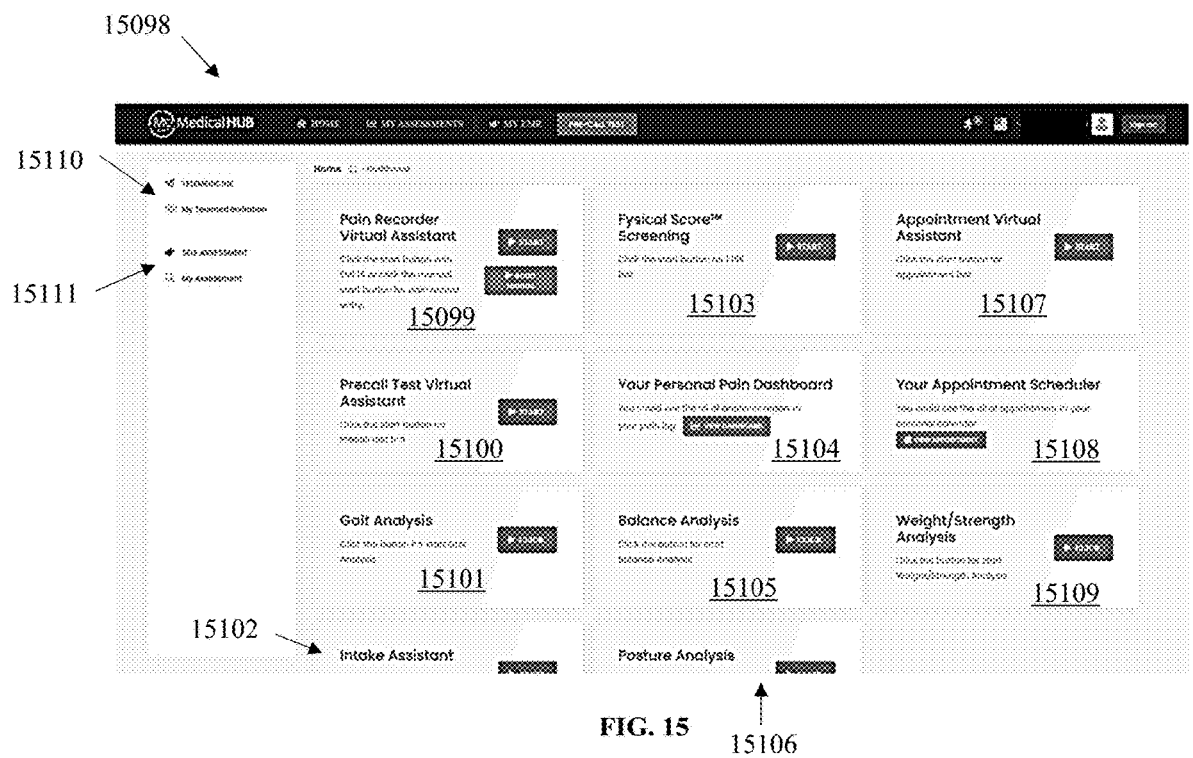
FIG. 15 illustrates an exemplary MMH interface used to facilitate patient data collection, according to an aspect.
Figure 16:
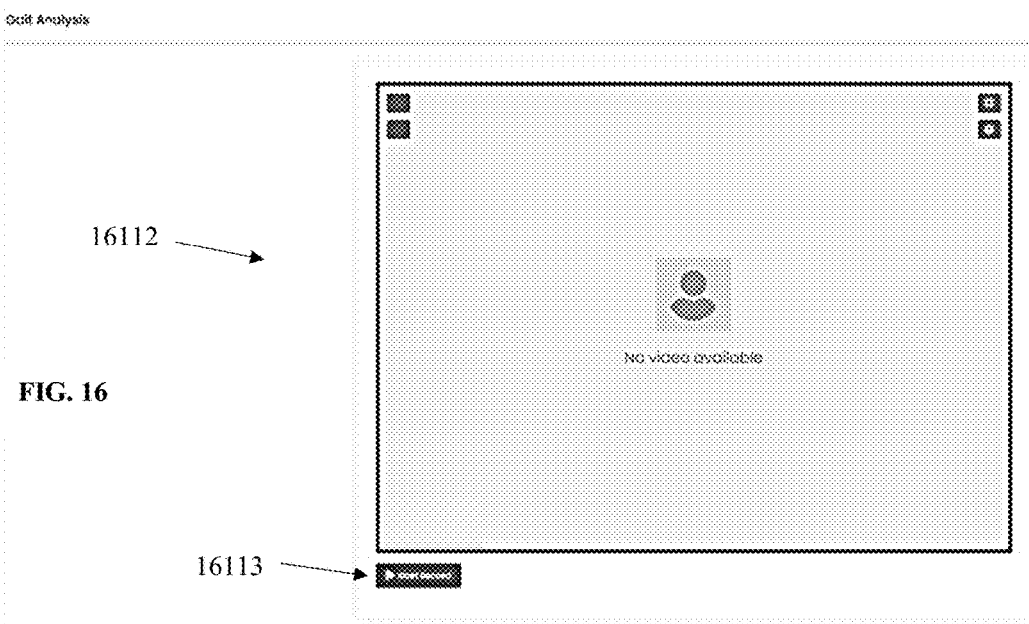
FIG. 16 illustrates a view of the video recording module for Gait Analysis, according to an aspect.
Figure 17:
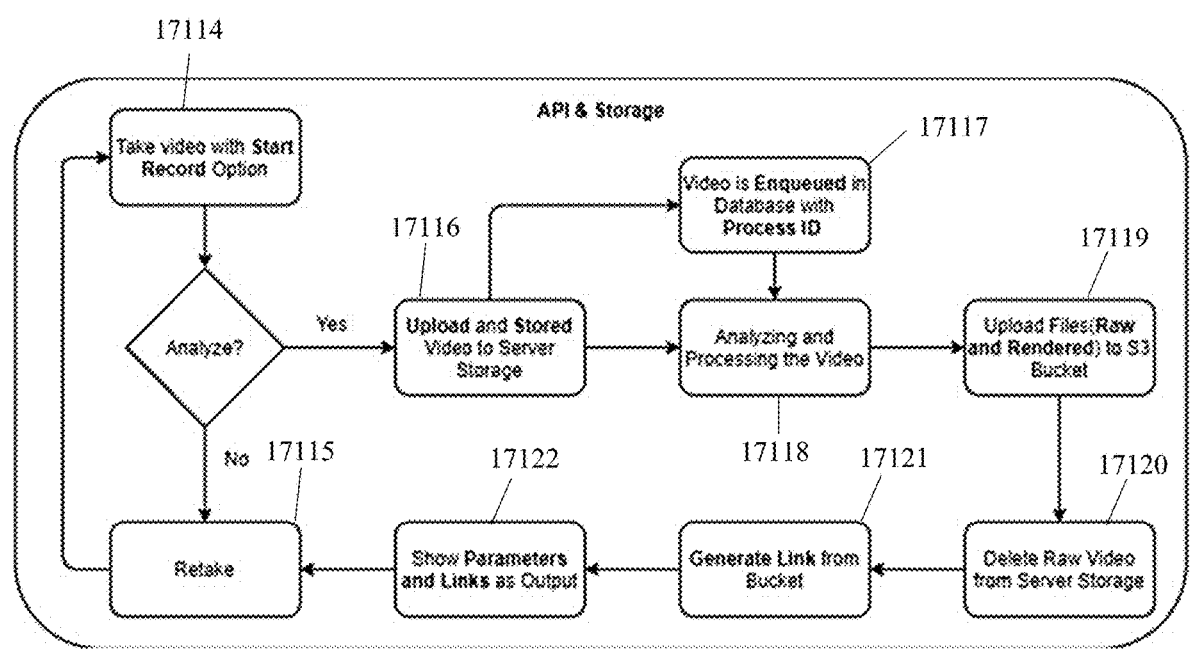
FIG. 17 illustrates the process followed by the Gait assessment APIs, according to an aspect.

FIG. 15 illustrates an exemplary MMH interface used to facilitate patient data collection, according to an aspect. FIG. 16 illustrates a view of the video recording module for gait analysis, according to an aspect. FIG. 17 illustrates the process followed by the gait assessment APIs, according to an aspect. In order to test the disclosed system using provided videos, a server with Django was created. Several APIs were implemented, which include a store API which is used to store raw videos in the Apache server, an enqueue API used to queue the videos one after another and a queuedStatus API used to tell the status of videos (whether it is rendered, video link, rendered images and videos' link etc.). An exemplary system embodiment may be configured as follows: Memory: 64KiB BIOS, Processor: Intel® Xeon® Platinum 8259CL CPU @ 2.50 GHz, RAM: 16 GB, System memory: 15GiB, Final Storage: AWS S3 Bucket, Display: NVIDIA Corporation—NVIDIA-SMI 455.32.00, -Tesla T4, -9W/70W, -0MiB/15109MiB, Driver Version: 455.32.00, CUDA Version: 11.1.

As can be seen by the exemplary interface 15098 of the patient portal of FIG. 15, a user may have access to a plurality of options upon accessing this interface 15098. The interface 15098 may operate as the prior disclosed patient portal 217 of FIG. 2, giving the user a means to perform assessments, record health tracking journals, etc. As can be seen in FIG. 15, the interface 15098 may allow the user to access a pain recorder virtual assistant 15099 to record pain events, a pre-call test virtual assistant 15100, a gait analysis module, as will be disclosed in greater detail hereinbelow, an Injury Risk Index Score screening 15103 to assess their Injury Risk Index Scores for each body region, a personal paint dashboard 15104 to review all record pain logs, a balance analysis 15105 to access potential issues with their balance, a posture analysis 15106 to access potential issues with their posture, an appointment virtual assistant 15107 to access an appointment for assistance with scheduling, an appointment scheduler 15108 to review each of their upcoming appointments and a weight/strength analysis 15109 to access their weight and strength.

Each analysis may utilize the EMMA bot to conduct a series of visually recorded tests to analyze an individual's body during a particular activity to assess their overall health and any potential underlying conditions. The disclosed interface 15098 may also include mechanisms for the users to interface with doctors via telemedicine based engagements 15110 and review their self-assessments 15111.

When using the disclosed interface 15098, a user may select the gait analysis 15101 option to access the gait assessment module ("video recording page for gait analysis") 16112 and record a video with the webcam by clicking on the "Start Record" button 16113. Upon being recorded, the video may be sent to the server or database by clicking an analyze video button, or a fresh video may be taken using a retake button, both of which will appear upon recording the initial video. In FIG. 16, an exemplary view of the video recording page for gait analysis is shown. Upon completing analysis of the uploaded video, said page may show the following: Result: Normal or Abnormal Gait, Notes: Your average stance percentage is X %, Video: Rendered video Link, Images: Rendered Images Link, Average stance Time, Average stance percentage, Average swing Time, Average swing percentage, Average cycle time, Average cycle length and Average cycle speed. The raw and rendered videos along with the rendered images may be stored in the aforementioned AWS S3 bucket. The results may be easily downloaded by clicking on the generated link. As disclosed previously, three APIs may be utilized for this procedure: the store, enqueue and queuedStatus APIs. The flow diagram for this process is depicted in FIG. 17, as will be described in greater detail hereinbelow. The system described hereinabove was tested by several users who provided webcam videos for gait analysis. A normal classification was returned when results were consistent with those of a normal gain. An abnormal classification was returned when the system could not detect any gait cycle, or the gait cycle was not within the range as defined in the model.

As disclosed above, FIG. 17 depicts the flow diagram for the API processes used in gait analysis assessments. This process may begin with taking a video with the start record option/button 17114. If the user is not satisfied with the video, the user may elect to retake the video 17115 rather than immediately continuing with analysis. Once the user is satisfied with the recorded video, the MMH system may begin analyzing the video by uploading and storing the video to server storage 17116. Upon being uploaded and stored, the video may be enqueued in the database with a process ID 17117 and the video may be analyzed and processed 17118. Once analyzed and processed, both the raw and rendered files may be uploaded to the S3 bucket 17119 and the raw video may be deleted from the server storage to save room, and a link may be generated from the bucket 17121. Finally, the parameters described above, and the generated link may be produced as an output 17122 and the user will again be given the opportunity to retake the video 17115 as needed. This general process may be utilized for each assessment described herein, as the machine learning algorithm is suitably equipped to provide the user with the results of their assessment with relative expediency when compared to the traditional process of scheduling and attending an in-person doctor's appointment.

FIG. 18 illustrates the comparison between the manually annotated angle measurements and API generated angle measurements for tests used to teach the algorithm for the angle-based approach, according to an aspect. FIG. 19 illustrates the comparison between the manually annotated angle measurements (actual) and API generated angle measurements (predicted) for an independent test set for the angle-based approach, according to an aspect.

As we can see from FIG. 19, the results from the independent test set compare the results between the actual gait classification against the prediction of the gait classification done by the disclosed pose estimation API. On, the first column, the IN represents that the gait videos are from the independent test set, and the next part is the actual test ID. In the last two rows, it is observed that, the actual average stance percentage and average swing percentage are within a range of a normal person, but they were predicted as abnormal, because the pattern of the heel strike was not normal. So, no proper gait cycle was found for any of the videos of these last two gaits and thus they were predicted as Abnormal, which was as same as ground truth. From the table, we can see that the angle-based approach is able to classify gait correctly in most cases, when compared against human experts. Thus, we can draw the conclusion that the angle based approach is successful in distinguishing between normal and abnormal gaits.

FIG. 20 illustrates the comparison between the manually annotated angle measurements and API generated angle measurements for an independent test set using the keypoint path track-based approach, according to an aspect. As can be seen in FIG. 20, the stance phases and swing phases for various gaits were detected as disclosed hereinabove for an independent dataset using the keypoint path track-based approach. The average stance percentage and swing percentages were calculated from the gait phases detected from the disclosed MMH system using the keypoint path track-based approach and the human expert for every test video as presented in FIG. 20. All of the samples of Dataset II indicate a normal gait based on both the human expert and system predicted results. One notable exception may be seen for Test ID 13, wherein the MMH system predicted the stance phase % incorrectly, as the test video contained blurriness at ankle points. This resulted in the speed graph for the opposite leg being incapable of generating the pattern required to identify the speed of a gait cycle effectively. However, as observed with the angle based approach, the keypoint path track-based approach was able to accurately generate stance/swing phase percentages and gait classifications that were suitably close those of human expert measured results.

As disclosed hereinabove, analyzing movements from a video with the help of Human Pose Estimation allows for raw video data to be utilized for gait assessments. A customtrained HigherHRNet 2D Pose Estimation, and Detectron2 were used to detect keypoints of a person's movements, and said keypoints where then used to calculate the necessary parameters to reach a decision about that person's movement to be within specific "normal" ranges or not, i.e., abnormal. Videos were captured with both camera and webcam and analyzed utilizing two separate approaches: an angle-based approach and a keypoint path track-based approach. By employing different methodologies as disclosed above, the different angles and distances were determined to find average stance time, average stance percentage, average swing time, average swing percentage, average cycle time, average cycle length and average cycle speed for a gait. Additional conditions, logics and techniques are also being explored in order to more accurately diagnose a user's gait. For example, the two methods disclosed hereinabove (the angle-based approach and the keypoint path tracking based approach) may be merged to acquire better results, by allowing for comparison of confidence values between the two approaches.

While the mechanism through which these methods measure the joint coordinate data may differ, the primary information they ultimately use in identifying whether a gait is normal or abnormal is largely the same. This primary information includes stance phase time (and thus percentage) and swing phase time (and thus percentage). With this info, the ±60% stance phase criteria may be used to determine if a gait is normal or not. The angle-based approach may also use a distance based criteria in identifying relevant phases (e.g., heel strike). If the angle-based approach also cannot achieve the necessary distance criteria (or cannot find a frame that depicts heel strike), it will suitably diagnose a gait as abnormal. This would be an accurate diagnosis, as long as the frames are not misread due to technical issues or limitations.

While the hereinabove described process may disclose the procedure for performing a gait assessment, other types of assessments may also be performed, as disclosed hereinabove. These assessments performed by the patients may be requested or assigned by providers. Assessments requested by the provider may be part of lead-in or follow-up to medical appointment.

Figure 21B:
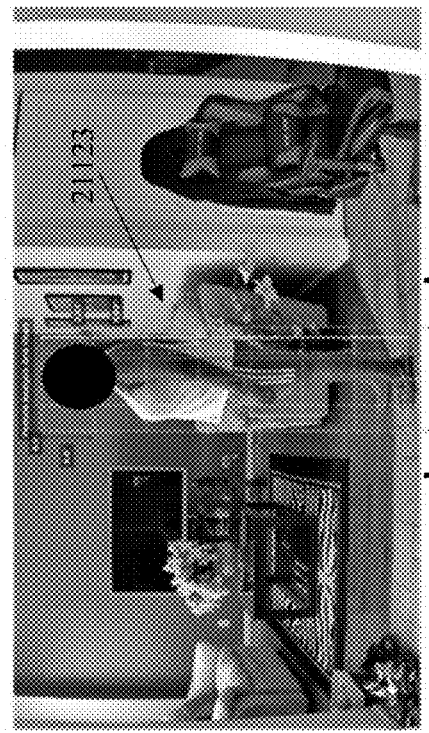
FIGS. 21A-21B illustrate the computer annotated figures from an exemplary comprehensive medical report generated by the MMH system, according to an aspect.
Figure 21A:
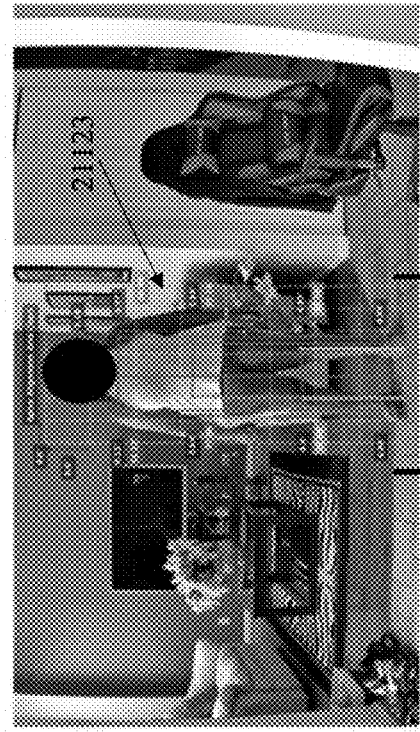
Figure 23:
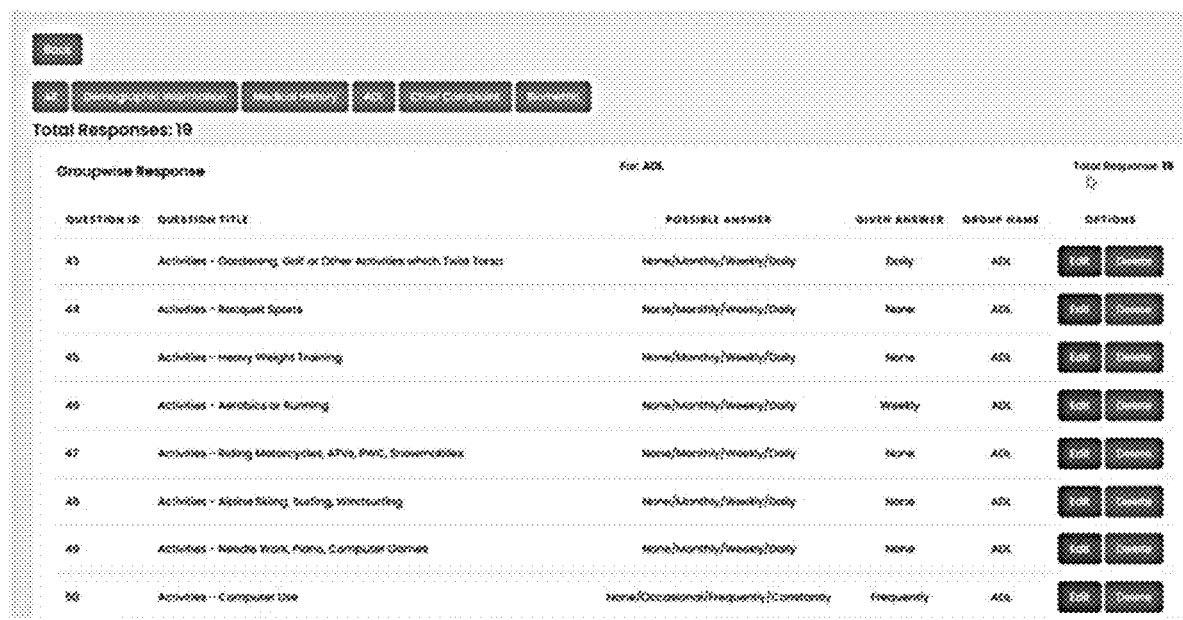
FIG. 23 illustrates the user interface utilized within the MMH system for recording patient ADLs, according to an aspect.

FIGS. 21A-21B illustrate the computer annotated figures from an exemplary comprehensive medical report generated by the MMH system, according to an aspect. FIG. 22 illustrates a deviation chart based upon a posture analysis, according to an aspect. FIG. 23 illustrates the user interface utilized within the MMH system for recording patient ADLs, according to an aspect. As described hereinabove, technologies and methodologies applied to the hereinabove described gait assessment process may also be applied to other types of assessments, such as posture assessments. As can be seen in FIGS. 21A-22, the displayed excerpt from a detailed medical report includes the results of a posture assessment. The angle measurements of relevant body parts are measured using the hereinabove disclosed machine learned processes, displayed as an annotated overlay 21124 on the patient's 21123 report pictures, which are utilized in the provided diagnosis. For example, the measurements collected from a posture assessment may allow the MMH system to diagnose potential conditions such as forward head and kyphosis, based on instructed rules formed through machine learning processes. Deviations in standard posture may be provided in a tabulated format within a health report, as seen in FIG. 22, to provide users and care providers with a clear indication of where abnormalities in their posture may originate from. These findings, while medically relevant in and of themselves, may also be used to provide additional diagnoses when used in conjunction with other findings. The hereinabove techniques disclosed for human pose estimation, particularly the angle-based approach (when active movement is not required for an assessment), may be useful for analyzing the body angles that occur during a posture assessment.

As disclosed previously, the MMH system may record and take into account a user's demographic (age, weight, BMI, etc.) and ADL when diagnosing conditions, as well as setting recovery goals. These ADLs may be recorded via the previously disclosed patient portal to help provide care providers with a better idea not only of what the patient may have done to cause certain conditions, but also what their treatment may need to do to allow them to continue performing the ADLs, such that their injury does not significantly affect their life. Additional patient health information, such as demographic information, medical history information, chief complaints, and biometric data may also be collected and/or stored on this page, to allow users to both observe and supplement their currently record health history.

The various benefits of the MMH system may allow for the growing gap formed between patients and the care they required to be bridged more effectively through the utilization of proper technologies. The utilization of machine learning technologies allows for diagnoses and low complexity interventions to be made without the immediate attention from a physician. These interventions may be provided to healthy patients as well, wherein said interventions may provide exercise/stretch instructions to help healthy patients stay healthy. Underlying health conditions may be identified through the enabled process automation and preventative measures may be implemented before health conditions begin to seriously affect a patient's health. By utilizing and leveraging the automation enabled by the MMH system with the existing healthcare system, a patient's can be monitored, diagnosed, and cared for without putting additional burden on health care professionals.

FIGS. 24A-24C illustrate the procedure for a patient 24125 performing a right thoracolumbar rotation range of motion measurement test, according to an aspect. FIG. 24D illustrates an image captured by a camera being utilized to record the right thoracolumbar rotation range of motion measurement test for a patient 24125, according to an aspect. In order for a patient 24125 to have their range of motion measured for a particular stretching procedure/range of motion test ("ROM" test"), the patient 24125 may utilize the "MyMedicalHub" system disclosed hereinabove. As described herein, the MyMedicalHUB system has developed a standardized, automated tool that uses 2-D ("two-dimensional") pose estimation to gather and generate ROM data in an unbiased manner. As a result of these herein disclosed stretching procedures being executed by the patient without the physical assistance/provocation of a clinician/physician, said ROM measurements collected may be referred to as "active" ROM measurements, or "AROM" measurements. It should be understood that while embodiments detailed hereinbelow may be configured to capture AROM measurements, the techniques and methods disclosed herein may also be configured to suitably capture other ROM measurement, such as "passive" range of motion measurements, in which a patient may be physically assisted by a clinician. It should also be understood that a patient 24125 may perform a particular stretching procedure during a corresponding ROM test in order to assess the patient's flexibility for a particular part of their body, as will be described in greater detail hereinbelow.

Again, MyMedicalHUB (MMH) is a cloud-based technology that automates and captures data that has been traditionally generated manually by clinicians. In an embodiment, patients are invited by a clinician to log-in to MyMedicalHUB via a secure link, register, and complete a comprehensive online physical assessment. The assessment may include subjective intake questions consistent with in-office evaluation and management examinations, such as Activities of Daily Living (ADLs), personal and family medical history, chief complaint(s), and, in some cases, subjective survey tools, such as an Oswestry Disability Index or STEADI Fall Risk Assessment Questionnaires.

Once the subjective intake questions are complete, the patient 24125 may be led through a series of provocative movements (e.g., a stretching procedure) to measure and record their range of motion using a computer, tablet, cell phone, smartphone, smart device, mobile device, or other device having a two-dimensional video camera (e.g., a camera configured to capture standard, two dimensional video footage), as opposed to a traditional goniometer and other sensor or device related signaling technology. In an embodiment, the MMH system may be configured to guide the patient through the correct stretching procedure through the utilization of EMMA system disclosed hereinabove. This EMMA system may utilize bot synthesized voice technology to verbally instruct patients through the corresponding stretching procedures to acquire a desired ROM measurement, wherein said synthesized voice may be played through the same device having the camera, or an auxiliary audio device.

It should be understood that the device utilized to capture a video of the patient performing the stretching procedure may comprise a processor, a user interface and a camera, to facilitate the suitable capture of all required information. It should be understood that the term "frame" and "picture" may be utilized interchangeably herein, wherein the frames/pictures correspond to the individual images that make up a recorded video. In an embodiment, the movements of the stretching procedure may be tailored to measure a patient's trunk rotation ROM. In an embodiment, the ROM measurements that are measured from the patient may be compared to normative ranges, as well as used to track objective data on a longitudinal basis. Following each stretching procedure, MMH may also ask the patient specific questions that encompass symptomatic criteria outlined in published, peer reviewed clinical studies and evidenced-based medicine protocols.

The MMH system may utilize two novel processes for measuring a patient's range of motion for a selected stretching procedure, such as trunk rotation. First, a unique process was developed for obtaining the measurement; and secondly, the MMH has been developed to utilize a special methodology for interpreting the corresponding technology's AI observations. For right thoracolumbar rotation ROM measurements, a patient may sit in a chair 24140 with their right side 24125*b* facing the camera, cross their arms, interlock their fingers adjacent to their naval, and rotate their shoulders in unison in a clockwise direction while keeping their hips stationary, i.e., forward facing, as seen in FIG. 24A-24C. The MMH system's video AI technology may be configured to capture the movement at maximum range/value on a recorded video, and superimpose virtual markers on specific key-points of the patient 24125, trace the range of movement for said key-points, calculate the angle at the maximum point of movement, measure it in degrees, and feed the information into a comprehensive report for the patient and/or provider. This comprehensive report containing the patient's ROM angle(s), as well as the recorded videos and corresponding frames/pictures of the video from which they were calculated, may be stored on a corresponding database within the MMH system, for later use or reference.

In order to provide the MMH system with the required images to accurately measure a patient's range of motion for a particular stretching procedure, it is important for both the patient performing stretching procedure and a clinician observing the range of motion test, if applicable, to follow the prescribed procedure for measuring said patient's range of motion. In an embodiment, the ROM test being performed may be configured to measure the right thoracolumbar rotation range of motion for a patient 24125. In order to perform this range of motion test, first a patient 24125 may sit on a chair height stool 24140 (approximately 18" high, in an embodiment) with their right side 24125*b* squarely facing a camera. Next, the patient 24125 may interlock their hands just above navel height and sit upright to the best of their ability, resetting their shoulders backward, and assuming a rest pose, as seen in FIG. 24A. After assuming the rest pose of FIG. 24A as described above, the patient may then turn their shoulders and trunk as far to the right (clockwise) as possible without moving their shoulders or hips, and then hold this pose until corresponding measurements are taken (e.g., the video is recorded), as seen in FIG. 24C. A frame for an intermediate pose, as shown in FIG. 24B, may also be captured from the recorded video, which may be helpful in tracing the movement of key-points on the patient.

The capture of intermediate poses from the recorded video, such as the intermediate pose for the right thoracolumbar rotation ROM stretching procedure, as seen in FIG. 24B, may be particularly relevant for detecting, tracking and compensating for any "drift" that may occur during the stretching procedure. Drift may be a phenomenon that occurs when the patient 24125 adjusts themselves to compensate for a lack of movement and/or rotation for a particular part of their body. This drift, if left unaccounted for, may negatively influence the accuracy of ROM measurements. As such, the MMH system may be configured to detect, track and compensate for drift through utilization of captured intermediate poses, such as the intermediate poses of FIG. 24B and FIG. 25B.

While the patient is performing the above described process, a provider/clinician may also follow a corresponding procedure in order to aid the patient 24125 in performing the stretching procedure, such as through verbal instruction. It should be understood that the instructions provided to the patient 24125 to guide them through the corresponding stretching procedure may be delivered to them by a clinician observing the patient (remotely or otherwise) and/or by the bot/EMMA system disclosed hereinabove. The instructions may be delivered to the patient 24125 in an outpatient clinical setting or outside an office setting, through corresponding telehealth-enabled technologies. In an embodiment, the provider/clinician may make sure that the patient is lined up properly with the camera while they are performing the corresponding range of motion procedure. The provider/clinician may also make sure that the patient sits upright and minimizes their hip movement while turning to the best of their ability to ensure accurate results may be obtained.

During the stretching procedure described hereinabove, the MMH system may be configured to automatically operate the camera to capture video of the patient in the rest pose of FIG. 24A and the fully stretched pose of FIG. 24C, as well as the patient in the intermediate pose of FIG. 24B, as applicable. As shown in FIG. 24D, this ROM measurement for the right thoracolumbar rotation may be measured and displayed within the MMH system. In the embodiment of FIG. 24D, the patient's ROM angle 24126 for their right thoracolumbar rotation may be about 56°. The MMH system may be configured to measure this ROM angle and provide it within a comprehensive report for later reference by the patient 24125 and/or a provider/clinician. As is understood, the herein disclosed process for measuring a patient ROM's may utilize two-dimensional pose estimation to gather and generate relevant results.

In describing the disclosed range of motion measurement process for a particular stretching procedure, it is useful to establish a "Goniometric Protocol" utilized to analyze the captured images. For a right thoracolumbar rotation range of motion test, an "axis" 24127 may be identified as the center point of a straight line between acromion processes 24128a, 24128b of the shoulders of the patient as measured from above the head. Furthermore, a "fixed arm" 24129 may remain parallel to the original position of the right acromion process 24128b in the rest pose of FIG. 1A, whereas a "moving arm" 24130 may move to point to the new position of the right acromion process 24128b in the fully stretched pose of FIG. 24C. With both the original position and new position of the patient's right acromion process 24128b known from measurements made to corresponding pictures/frames of the recorded video, the patient's range of motion for right thoracolumbar rotation may be determined, as indicated by ROM measurement ("ROM angle") 24126 in FIG. 1D. The disclosed process measures a series of ranges, key-points, and lengths within corresponding frames of the captured video, translates them into digitized data points, and measures the movement of these data points using a corresponding methodology, based on the ROM measurement being collected.

In order to enable the calculation of the hereinabove described ROM measurement 24126 for the corresponding procedure, the MMH system may follow a corresponding process. When a new patient first accesses MMH, they may be directed through a registration via a link, if they are outside of a clinic, or during an in-office encounter. Once complete, the MMH system establishes a secure, individual portal for every patient assessed. Once established, patients can reenter their portal via a web link or saved URL, access information pertaining to their assessments, including exercises, and conduct new assessments, if ordered by the provider. The patient may be allowed to position a device having a camera in the correct position to allow for suitable video capture, such that ROM measurements may be obtained. Then, the patient may be instructed on how to perform the necessary stretching procedure to calculate the desired ROM angle. In an embodiment, this instructing of the patient may be done as an automated aspect of the MMH system, such as through bot delivered instructions, wherein a clinician is absent, and the stretching procedure is led by the EMMA system (e.g., a self-led bot assessment.) In an alternative embodiment, the clinician/provider may verbally guide the patient 24125 through the steps of the stretching procedure. While the stretching procedure is being performed, the MMH system may be configured to automatically record a video of the patient 24125 using the camera, and identify and extract frames corresponding to the pertinent poses for ROM measurements. These frames may include at least a frame of the patient in the rest pose, as seen in FIG. 24A, and a frame of the patient at their maximum range of motion/maximum extension, called a fully stretched pose, as seen in FIG. 24C.

With the necessary frames of the patient 24125 performing the stretching procedure obtained from the recorded video, the ROM measurement procedure may continue with the identification of the analytic elements, such as the axis 24127, fixed arm 24129 and moving arm 24130, within the recorded frames. As described hereinabove, the identification of the axis, fixed arm 24129 and moving arm 24130 may be done through the tracking of relevant key-points on the patient within the corresponding frames, such as their right acromion process 24128b and their left acromion process 24128a for left or right thoracolumbar range of motion measurements. With the fixed arm 24129, moving arm 24130 and axis 24127 identified, the ROM angle 24126 may be calculated by measuring the angle difference between the moving arm 24130 and the fixed arm 24129. In an embodiment, the fixed arm 24129 may be formed between the axis 24127 and the right acromion process 24128b while in the rest position of FIG. 1A, whereas the moving arm 24130 may be formed between the axis 24127 and the right acromion process 24128 while in the fully stretched position of FIG. 24C position. With the right thoracolumbar range of motion angle 24126 calculated, the right thoracolumbar range of motion angle 24126 may be reported to the patient/clinician, as well as recorded on a comprehensive health report for the patient/clinician. It should be understood that the MMH system may be configured to be utilized to measure any necessary ROM angles by recording/observing the patient 124125 perform the corresponding stretching procedure while also identifying the positions of relevant key-points/key analytic elements, accordingly. This process of identifying a patient's range of motion for a particular stretching procedure may also be done for other stretching procedures for other ROM tests, such as left thoracolumbar rotation ROM test, as disclosed hereinbelow.

Figures 25A, 25B, 25C:
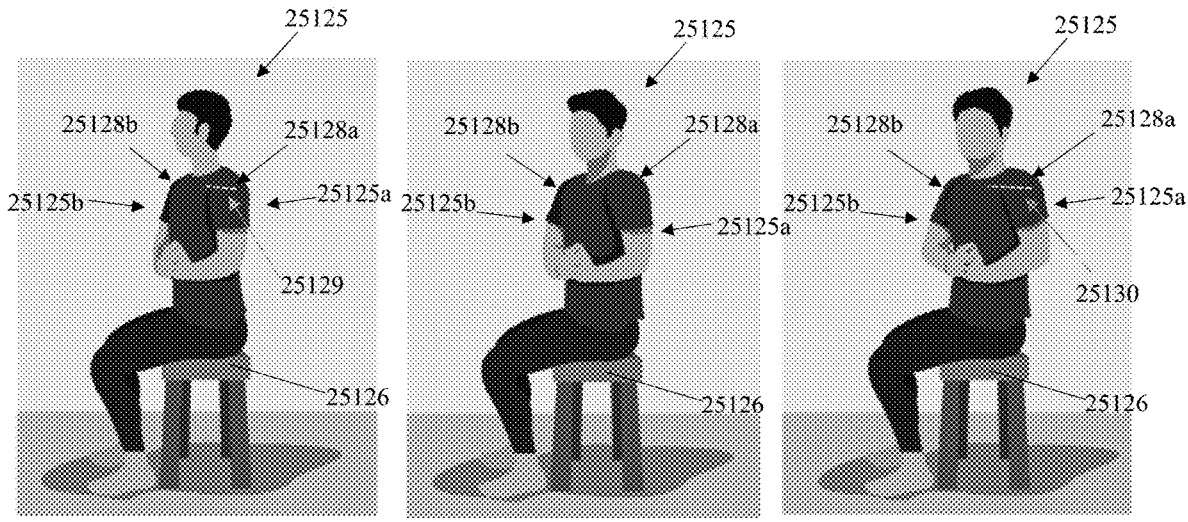
FIGS. 25A-25C illustrate the procedure for a patient performing a left thoracolumbar rotation range of motion measurement test, according to an aspect.
Figure 25D:
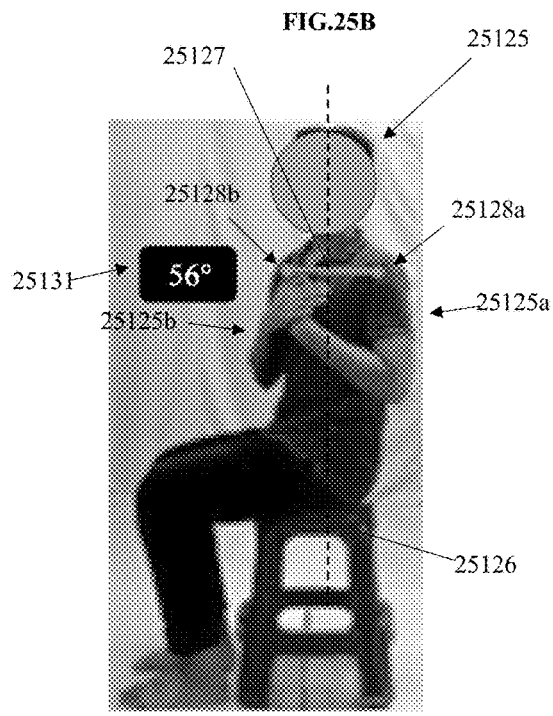
FIG. 25D illustrates an image captured by a camera being utilized to record the left thoracolumbar rotation range of motion measurement test for a patient, according to an aspect.

FIGS. 25A-25C illustrate the procedure for a patient 25125 performing a left thoracolumbar rotation range of motion measurement test, according to an aspect. FIG. 25D illustrates an image captured by a camera being utilized to record the left thoracolumbar rotation range of motion measurement test for a patient 200, according to an aspect. As disclosed hereinabove, the patient 200 may access the MMH system in order to utilize the herein disclosed left thoracolumbar rotation range of motion measurement test.

In an embodiment, the process utilized to capture the left thoracolumbar rotation ROM may mirror the process utilized to capture the right thoracolumbar rotation ROM, as described in FIG. 24A-24D above, with a few exceptions. In order to perform this range of motion test, first a patient 25125 may sit on a chair height stool 25126 (approximately 18" high, in an embodiment) with their left side 25125a squarely facing a camera. Next, the patient 25125 may interlock their hands just above navel height and sit upright to the best of their ability, resetting their shoulders backward, thus assuming a rest pose for the left thoracolumbar rotation ROM test, as seen in FIG. 25A. After assuming this rest pose, the patient may then turn their shoulders and trunk as far to the left (counterclockwise) as possible without moving their shoulders or hips, and then hold this pose until corresponding measurements are taken (e.g., the video is recorded), as seen in FIG. 25C. An intermediate pose for the left thoracolumbar rotation range of motion measurement test, as shown in FIG. 2B, may also be captured if helpful or necessary. As disclosed hereinabove, the intermediate pose from a stretching procedure may be utilized to help detect, track, and compensate for drift during a ROM test. As with the previous ROM measurement embodiment, frames will be identified from the captured video for at least the extreme values, such as the rest pose of FIG. 25A and the fully stretched pose of FIG. 25C, to determine the patient's ROM for the left thoracolumbar rotation stretching procedure. Aside from the changes disclosed hereinabove, the process for measuring a patient's left thoracolumbar rotation ROM may be largely the same as the process for measuring a patient's right thoracolumbar rotation ROM.

Similarly to the right thoracolumbar rotation range of motion measurement test, the left thoracolumbar rotation range of motion measurement test may establish a goniometric protocol in order to suitably establish the information to be collected to assess the patient's range of motion for said procedure. Again, an "axis" 25127 may be identified as the center point of a straight line between acromion processes 25128a, 25128b of the patient's shoulders as measured from above the head. Furthermore, the corresponding "fixed arm" 25129 may remain parallel to the original position of the left acromion process 25128a in the rest pose of FIG. 25A, whereas the corresponding "moving arm" 25130 may move to point to the new left acromion process 25128a position in the fully stretched pose of FIG. 25C. With the both the original position and new position of the patient's left acromion process 25128a known from measurement of the recorded frames, the range of motion for left thoracolumbar rotation may be determined, as indicated by angle measurement 25131 in FIG. 25D. In an embodiment, the angle measurement 25131 formed between the fixed arm and moving arm for the left thoracolumbar rotation may be stored alongside other recorded angle measurements corresponding to other ROM tests, for the generation of a comprehensive health report for the patient.

As a result of the described key-point identification and tracking method utilized to measure the ROM angles for a stretching procedure, wearable sensors and other peripheral technologies are not required. By simply utilizing a device with a camera and an internet connection to capture all of the necessary raw data to determine corresponding ROM values, the disclosed range of motion measurement process may be done in nearly any environment. As disclosed hereinabove, the herein disclosed process may utilize two-dimensional pose estimation to gather and generate relevant results from a captured recording, such as accurate ROM data for a patient 25125, in an unbiased manner. Furthermore, this particular process can be executed virtually through telehealth enabled devices and its corresponding ROM measurements can be captured and recorded remotely with a high degree of accuracy through verifiable images/frames. As disclosed herein, the disclosed process utilizes the MMH system to measure a series of ranges, key-points, and lengths, then translates them into digitized data points, and measures the movement of these data points using a complex methodology, thus providing the desired ROM angles for a particular stretching procedure using only captured images/frames from the video recording. By utilizing the disclosed ROM measurement process, a patient may be provided with a fast and easy mechanism for determining their range of motion of a particular stretching procedure remotely and without having a clinician on site.

Figure 26A:
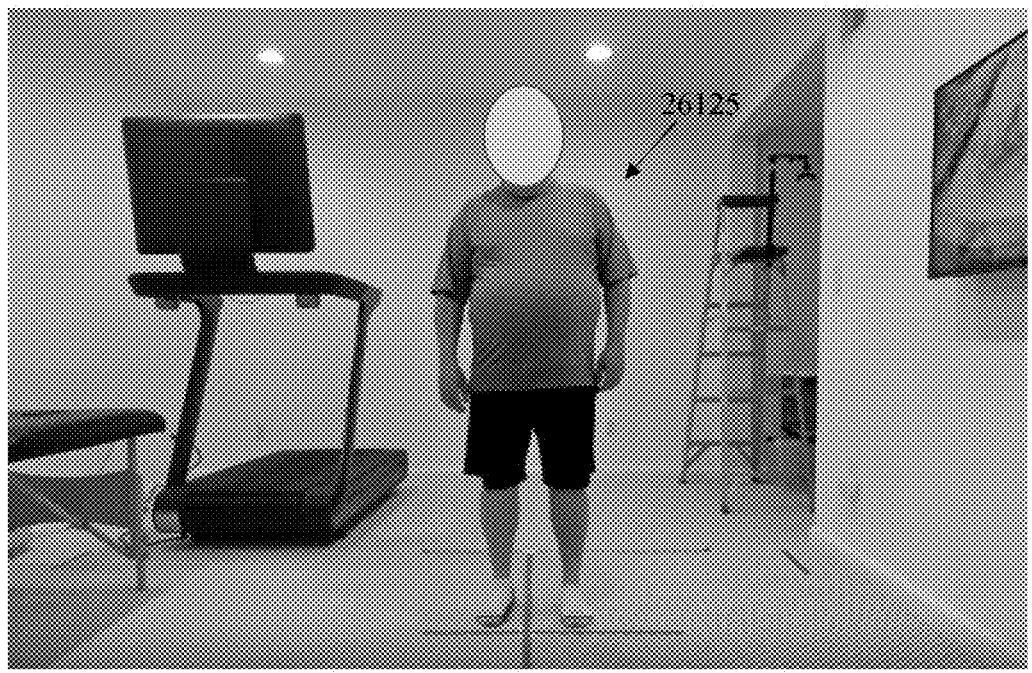
FIGS. 26A-26B illustrate the procedure for a patient performing a left trunk lateral bending range of motion measurement test, according to an aspect.
Figure 26B:
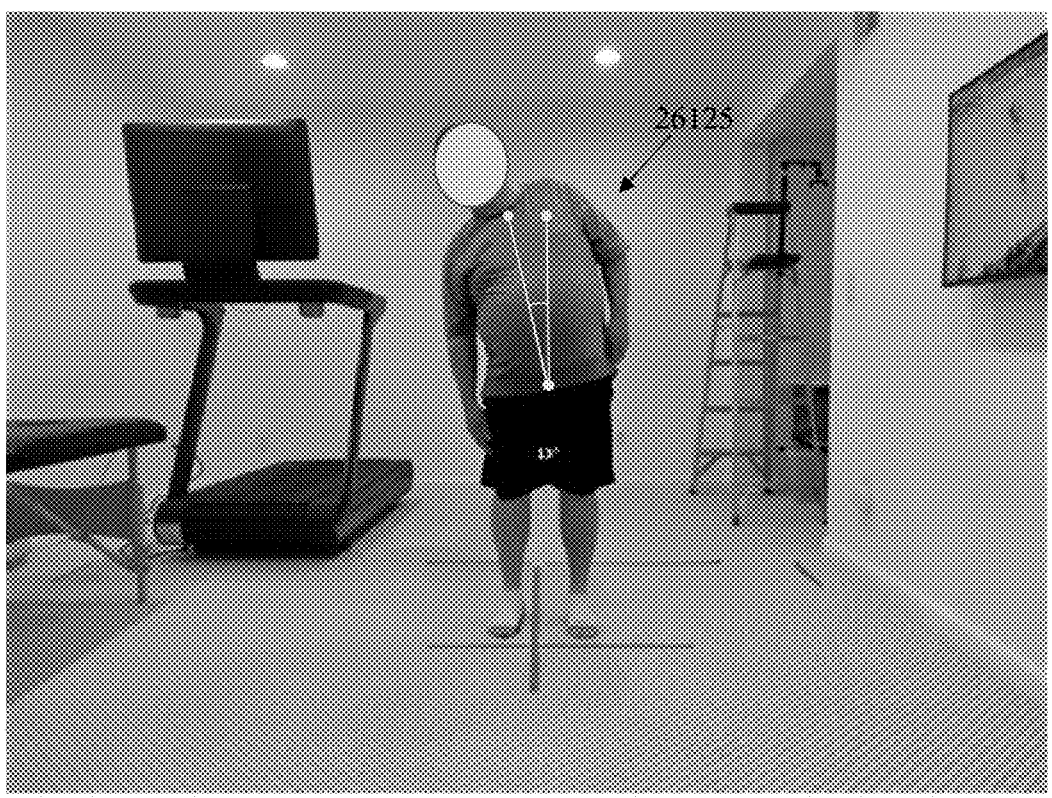

FIGS. 26A-26B illustrate the procedure for a patient 26125 performing a left trunk lateral bending range of motion measurement test, according to an aspect. As is understood, each of the range of motion measurement tests performed herein may be recorded by the disclosed MMH system, such that range of motion information may be obtained from a patient for a wide variety of different range of motion tests. Again, it should be understood that the MMH/computer system may be configured to analyze a video collected using a corresponding device (e.g., a camera) in order to collect ROM measurements to perform a corresponding motion test. One such test may be a "trunk lateral bending" range of motion test (also known as lateral flexion). Trunk lateral bending is a movement where the patient's torso bends to one side, reducing the distance between their rib cage and their pelvis on that respective side. This action assesses the range of motion and flexibility of their spine and their lateral trunk muscles. To measure lateral trunk bending accurately, key anatomical landmarks such as the point midway between the left and right anterior superior iliac spines (ASIS) and the sternal notch may be utilized.

For the trunk lateral bending range of motion test, the patient 26125 may begin standing upright with their feet shoulder-width apart for stability. Their arms can be placed by their sides or on their hips. From this starting position, the patient 26125 bends their torso directly to one side (either left or right), without leaning forward or backward. This movement should be performed smoothly and in a controlled manner, keeping the patient's hips facing forward and their legs straight to isolate the movement to their trunk. The keypoints on a patient that may be tracked in order to measure the patient's trunk lateral bending range of motion during the test are the midpoint between their left and right ASIS and their sternal notch. The Midpoint between the left and right ASIS is a central point at the pelvis that serves as the lower reference for trunk movement, helping to ensure that the bending action is isolated to the upper torso without hip displacement, whereas the sternal Notch (located at the top of the sternum) moves laterally away from the centerline as the trunk bends to one side. Tracking the movement of the sternal notch provides a clear measure of the degree of lateral bending. The range of motion for trunk lateral bending is quantified by measuring the angle formed between a vertical line from the midpoint between the ASIS to the sternal notch, and the new position of the sternal notch after bending, which is measured to be 13 degrees for the right side of the patient 26125 in FIG. 26A-26B.

Figure 27A:
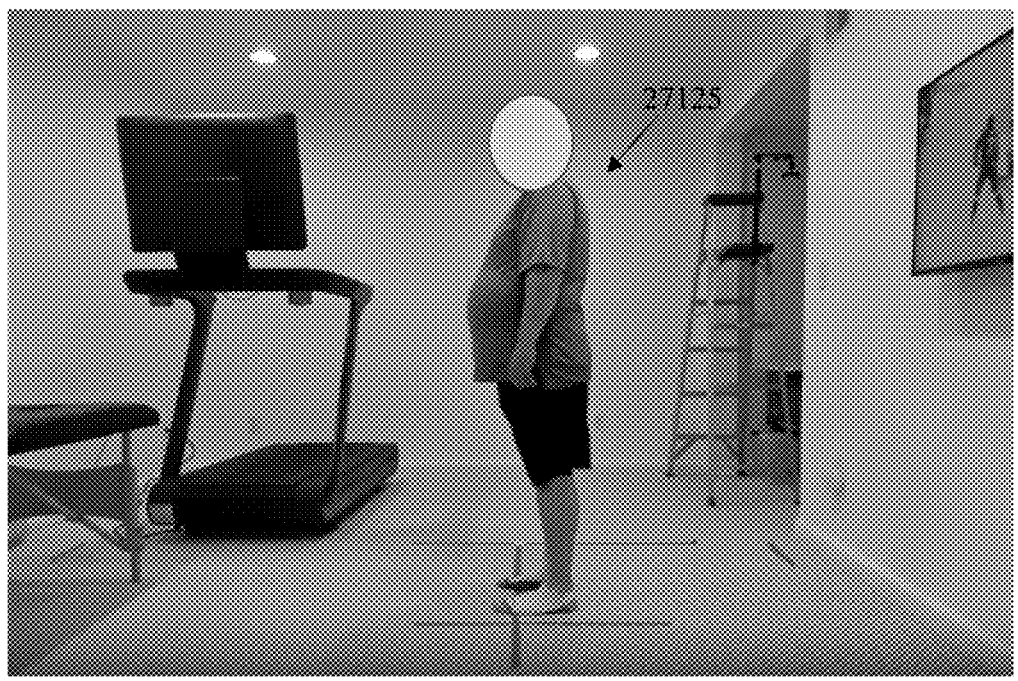
FIGS. 27A-27B illustrate the procedure for a patient performing a trunk flexion range of motion measurement test, according to an aspect.
Figure 27B:
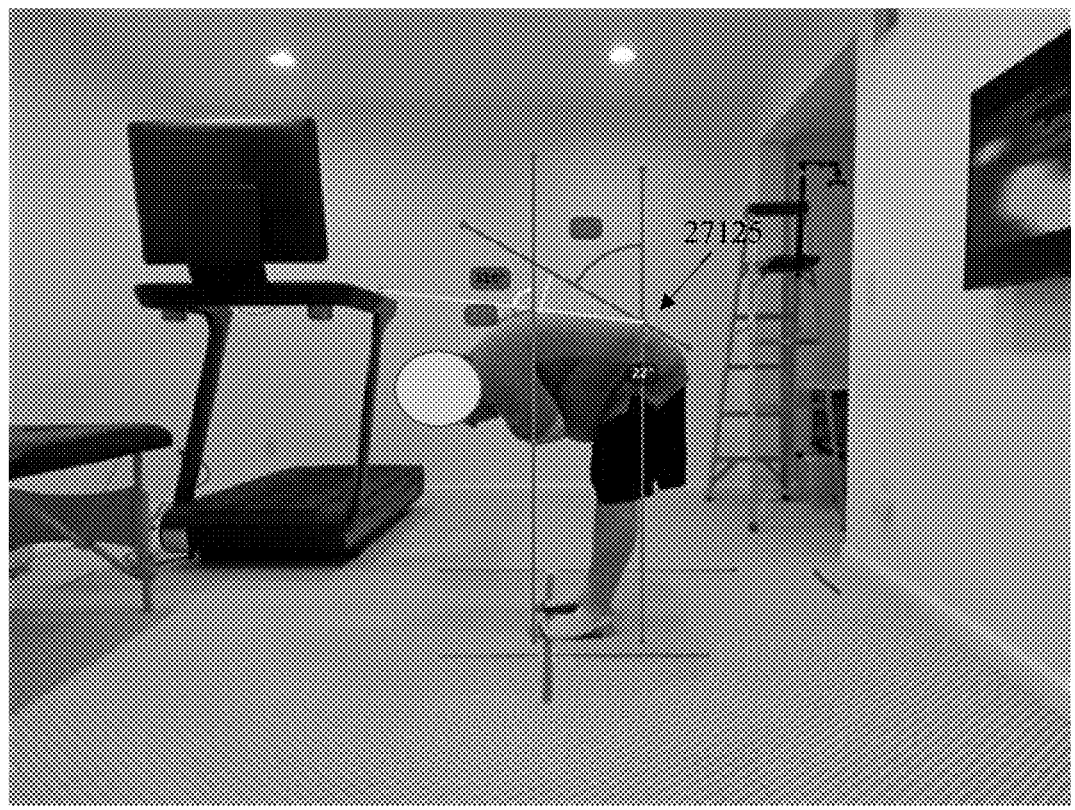

FIGS. 27A-27B illustrate the procedure for a patient 27125 performing a trunk flexion range of motion measurement test, according to an aspect. Trunk flexion is a movement where the patient's torso bends forward from their hips, reducing the angle between their chest and their legs. This action is crucial for assessing the range of motion and flexibility of the abdominal muscles, the lower back, and the spine of a patient 27125. To accurately measure trunk flexion the MMI system may be configured to track corresponding anatomical landmarks as keypoints.

For the trunk flexion range of motion test, the patient 27125 may begin standing upright with their feet shoulder-width apart for stability. Their arms can be placed by their sides, across their chest or extended straight forward parallel to the ground, depending on the specific measurement requirements. From this starting position, the patient 27125 may bend forward at the waist as far as comfortably possible without bending their knees. This movement should be smooth and controlled, ensuring the focus is on isolating the movement to the trunk to avoid any compensatory movements from the lower limbs or hips.

The keypoints for this range of motion test may be the head of the humerus, head of the femur and lateral condyle of the femur. The keypoint at the head of the humerus, located at a corresponding upper arm, serves as an upper reference that moves forward with the upper body during flexion. It provides an indicator of how much the upper torso moves in relation to the hips. The keypoint at the head of the corresponding femur serves as a central pivot point at the hip, indicating the base from which the upper body flexes. It remains relatively stable as the torso bends. The keypoint at the lateral condyle of the femur, located near a corresponding knee, helps ensure the lower limbs remain stationary and provides a lower boundary for measuring the relative movement of the upper body during flexion. For ROM measurement tests that do not explicitly measure range of motion for the left or right side of a patient's body (or a corresponding left or right part of the patient's body), keypoints may be located on either a patient's left side or on their right side, as long as that side's keypoints may be accurately tracked by a camera. Keypoints for a measurement test may all be located on the same lateral side of a patient's body, unless specified otherwise.

The range of motion for trunk flexion is quantified by measuring the angle formed by a line from the lateral condyle of the femur to the lateral head of the femur and another line from the lateral head of the femur extending through the mid axillary line towards the head of the humerus, where one line aligns with the upper body trajectory and the other with the baseline established at the hip, with the fulcrum located at the lateral head of the femur. As seen in FIG. 27B, the disclosed patient's range of motion for trunk flexion is 22 degrees.

Figure 28A:
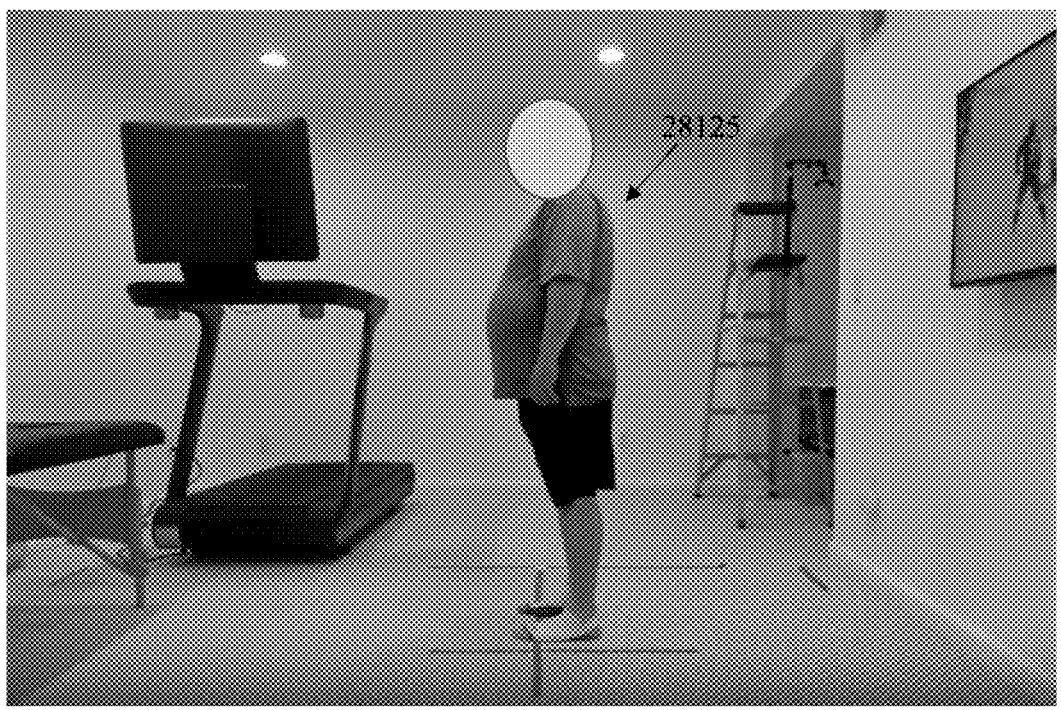
FIGS. 28A-28B illustrate the procedure for a patient performing a trunk extension range of motion measurement test, according to an aspect.
Figure 28B:
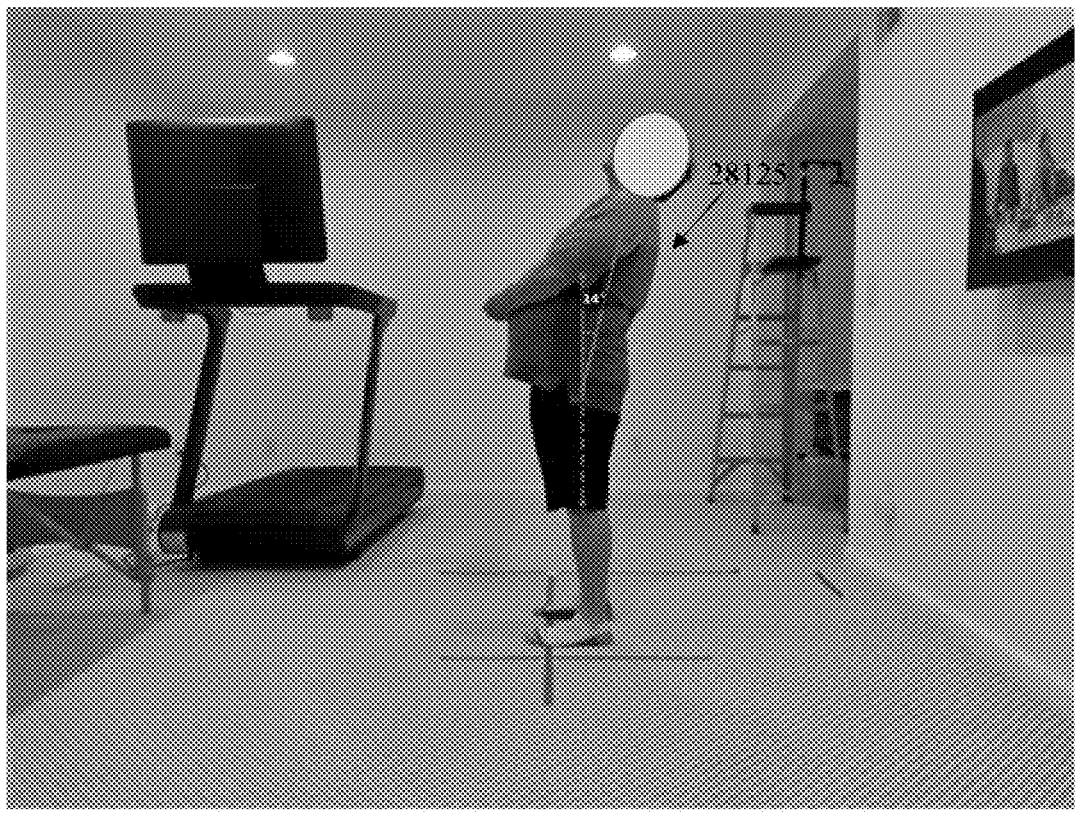

FIGS. 28A-28B illustrate the procedure for a patient 28125 performing a trunk extension range of motion measurement test, according to an aspect. Trunk extension is the movement where the patient's torso bends backward, increasing the angle between the front of the thighs and the torso. This movement is crucial for evaluating the range of motion and strength of the back muscles and spinal flexibility.

For the trunk extension range of motion test, the patient 28125 may begin standing upright with their feet shoulder-width apart to ensure stability, with their arms placed at the sides, on their hips, or crossed over their chest, based on comfort, and to avoid influencing the movement. From the upright position, the patient 28125 may gently bend their torso backward from their hips as far as comfortably possible without bending their knees. The movement should be performed smoothly and controlled, focusing on isolating the movement to their upper body and avoiding any compensatory movements from their legs.

The keypoints for the trunk extension range of motion test may include the lateral condyle of the femur, the lateral head of the femur and the mid axillary line toward the head of the humerus. The keypoint on the lateral condyle of the femur may serve as a lower reference point, helping to ensure the lower body remains stable and does not contribute to the trunk movement. The keypoint on the lateral head of the femur (located near the hip) provides a pivotal reference for the movement at the hip level, indicating the base from which the upper body extends. The keypoint on the mid axillary line towards the head of the humerus (said line being along the side of the body from the lateral aspect of the torso extending upward) is crucial in measuring how much the upper body moves relative to the lower body.

The range of motion for trunk extension is quantified by measuring the angle formed by a line from the lateral condyle of the femur to the lateral head of the femur and another line from the lateral head of the femur extending through the mid axillary line towards the head of the humerus, where one line aligns with the upper body trajectory and the other with the baseline established at the hip, with the fulcrum located at the lateral head of the femur. In the embodiment of FIG. 28B, the measured range of motion for trunk extension is 14 degrees. The disclosed range of motion tests described in FIGS. 24A-28B may be classified as back/trunk range of motion tests, for simplicity. These back/trunk range of motion tests may be performed as part of a back/trunk assessment, similarly to the hereinabove described gait assessment. Furthermore, by performing this described back assessment, the MMH system may be configured to generate a back/trunk diagnosis by evaluating the resultant range of motion values to assess and suitably report a patient's MSK health within their back region.

Figure 29A:
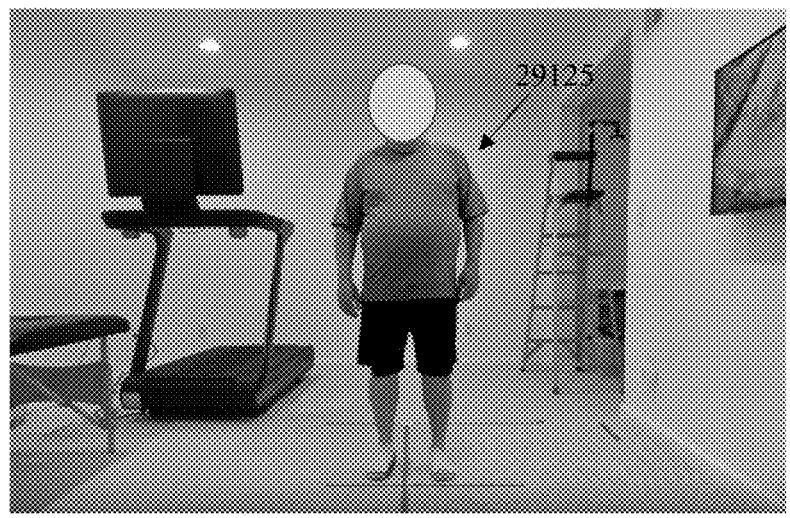
FIGS. 29A-29C illustrate the procedure for a patient performing a shoulder abduction range of motion measurement test, according to an aspect.
Figure 29B:
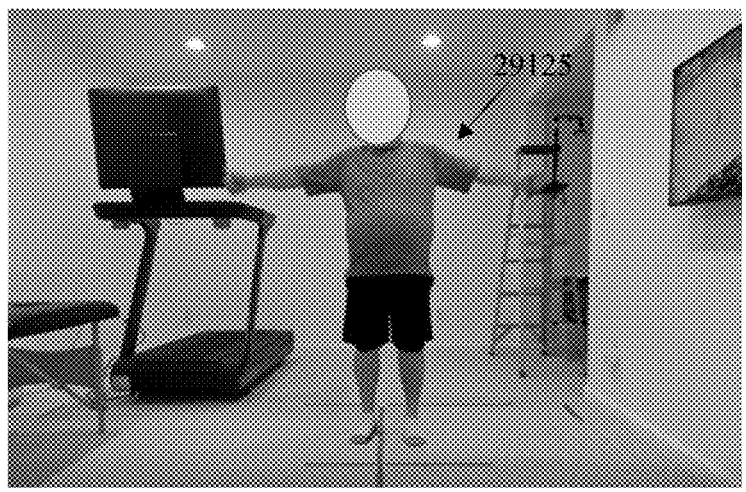
Figure 29C:
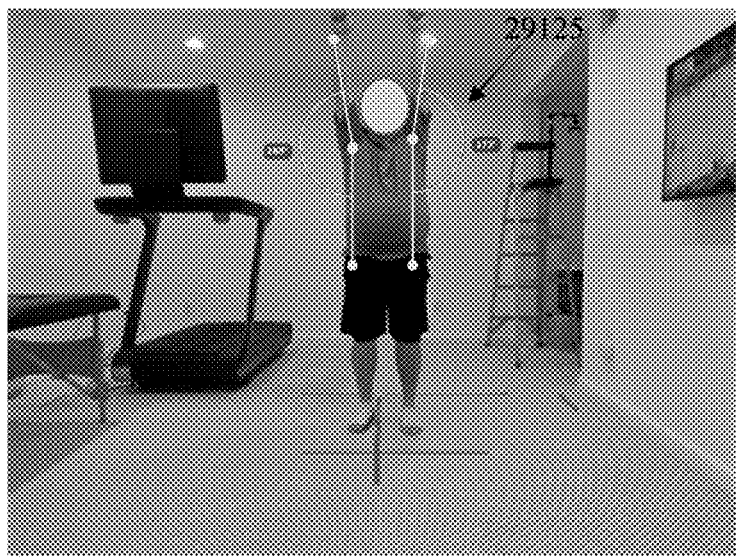

FIGS. 29A-29C illustrate the procedure for a patient 29125 performing a shoulder abduction range of motion measurement test, according to an aspect. Shoulder abduction is a movement where the patient's arm is lifted away from their body along the frontal plane, moving from a position by the side of their body to a position perpendicular to their torso, or even higher towards a fully vertical position. This movement is essential for assessing the range of motion and strength of their shoulder joint and its surrounding musculature.

For the shoulder abduction range of motion test, the patient 29125 may begin with their corresponding arm hanging naturally at their side, with the palm facing their body. Their anterior shoulder point serves as the pivot, and the cubital fossa is aligned with the side of their body. The patient then raises their arm sideways, away from their body, without rotating their forearm or their palm, maintaining a straight elbow if possible until their arm is raised as close to parallel with the floor as comfortably possible or further towards a vertical position.

The keypoints for the shoulder abduction range of motion measurement test may include the anterior shoulder point, the cubital fossa of the elbow and a vertical line perpendicular to the floor. The keypoint for the anterior shoulder point remains stationery and acts as the pivot point from which the arm is abducted. The keypoint for the cubital fossa of the elbow moves in an arc as the arm is raised. The trajectory and final position of the cubital fossa help indicate the degree of abduction. The vertical line perpendicular to the floor acts as a reference line against which the movement of the arm can be measured. It helps determine how far the arm has moved away from the body's side.

The range of motion for shoulder abduction is quantified by measuring the angle formed between the arm and the vertical line when the arm is raised. Starting from zero degrees when the arm is at the side, the measurement goes up to 180 degrees if the arm can be lifted to be straight upward, aligned with the vertical line. As can be seen in FIG. 29C, the range of motion for the patient's left and right shoulder abduction are 172 degrees and 169 degrees, respectively.

As is understood, certain stretches may be performed in multiple directions (e.g., left or right) or may otherwise be performed by a left or right portion of the body. In such instances, it should be understood that the keypoints may be located on the corresponding side of a patient's body, depending on the test being performed. For example, for a patient's left shoulder abduction test, the keypoints may include the anterior shoulder point for their left shoulder and the cubital fossa of their left elbow. For range of motion tests that do not measure left or right lateral movement or a specific lateral side of the patient's body, such as the trunk flexion range of motion measurement test of FIGS. 27A-27B, keypoints on either the patient's left side or right side may be used to get an accurate measurement.

Figure 30A:
FIGS. 30A-30C illustrate the procedure for a patient performing a front view elbow flexion range of motion measurement test, according to an aspect.
Figure 30B:
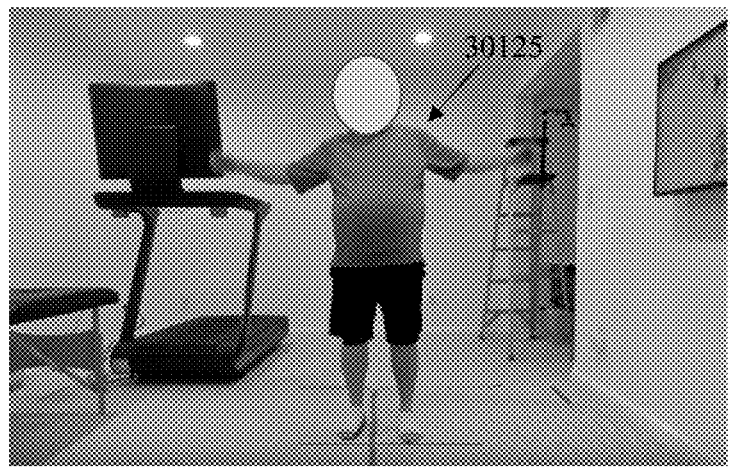
Figure 30C:
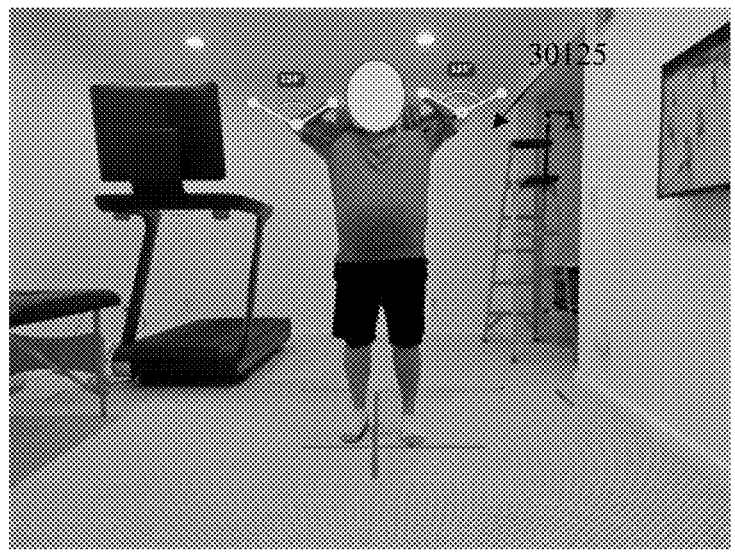

FIGS. 30A-30C illustrate the procedure for a patient 30125 performing a front view elbow flexion range of motion measurement test, according to an aspect. Elbow flexion is the movement where the patient's forearm is bent towards their upper arm, decreasing the angle at the elbow joint. It is a fundamental movement for assessing the functionality and range of motion of the elbow.

For the front view elbow flexion range of motion test, the patient 30125 may begin with their corresponding arm extended straight along their side, with their elbow fully extended and their palm facing forward. This position allows clear visibility and measurement of the key anatomical landmarks/keypoints. The patient may then flex their elbow, bringing their forearm up towards their shoulder. The movement should be smooth and controlled, ideally keeping their upper arm stationary, to isolate the movement to the elbow joint.

The keypoints for the front view elbow flexion range of motion measurement test may include the anterior head of the humerus, the medial epicondyle of the humerus and the styloid process of the ulna at the wrist. The keypoint at the anterior head of the humerus serves as the proximal reference point at the upper arm, indicating the base of the movement. The keypoint at the medial epicondyle of the humerus, located on the inner side of the elbow, acts as a central pivot point for the movement, providing a clear marker for the degree of flexion at the elbow. The keypoint at the styloid process of the ulna at the wrist acts as a landmark at the distal end of the forearm that moves in an arc as the elbow is flexed. The path and endpoint of the styloid process are crucial for determining the extent of the forearm's movement during flexion.

The range of motion for the front view elbow flexion range of motion measurement test is quantified by measuring the angle formed between the upper arm and the forearm at the point of maximum flexion, where one arm aligns with the anterior head of the humerus, and the other aligns with the styloid process of the ulna. As can be seen in FIG. 30C, the patient's left and right elbow flexion range of motion measurements for the front view elbow flexion range of motion measurement test are 125 degrees and 124 degrees, respectively. It should be understood that corresponding view designations (e.g., "front view" for when the camera is aimed at the front of a patient, "side view" for when the camera is aimed at the side of a patient", etc.) may be utilized to distinguish different range of motion measurement tests for the same body region/part, such as the front view elbow flexion range of motion measurement test shown in FIGS. 30A-30C, and the side view elbow flexion range of motion measurement test shown in FIGS. 38A-38B.

Figure 31A:
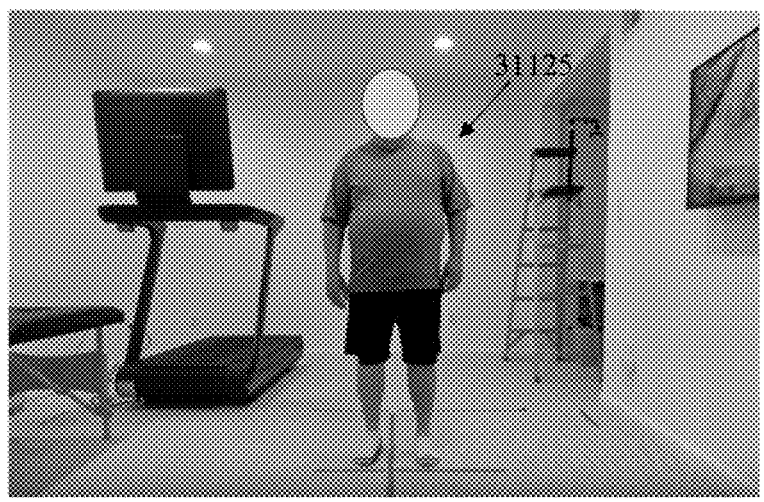
FIGS. 31A-31C illustrate the procedure for a patient performing a shoulder adduction range of motion measurement test, according to an aspect.
Figure 31B:
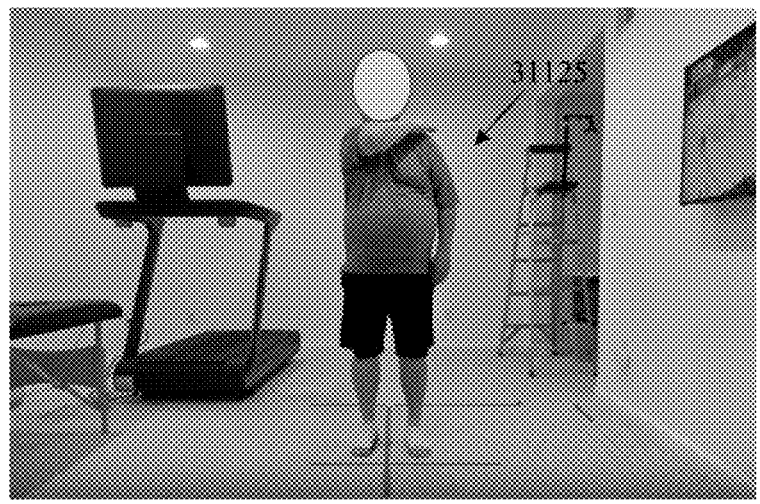
Figure 31C:
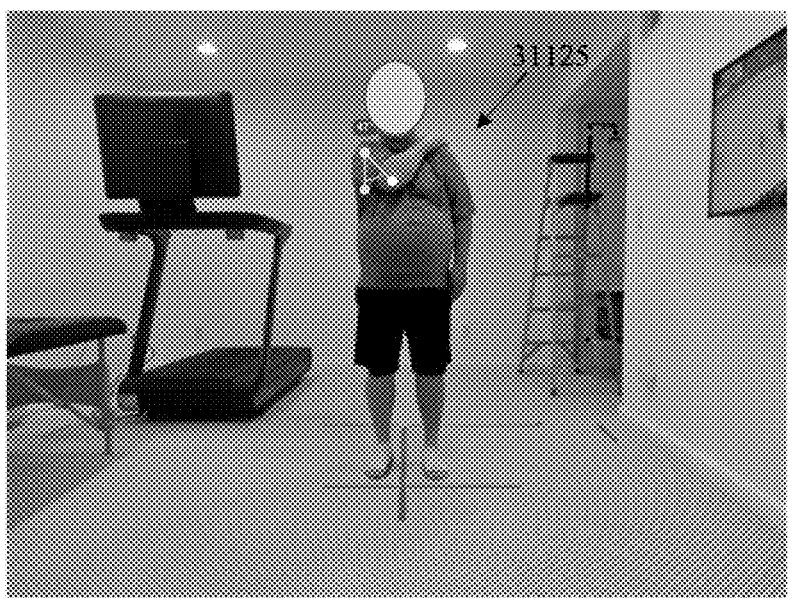

FIGS. 31A-31C illustrate the procedure for a patient 31125 performing a shoulder adduction range of motion measurement test, according to an aspect. Shoulder adduction is the movement of bringing the patient's arm down to the side of their body from an abducted (raised) position, moving their arm across the frontal plane towards the body. This action is vital for assessing the shoulder joint's range of motion and the functioning of its surrounding muscles.

For the shoulder adduction range of motion test, the patient 31125 may begin with their arms abducted, raised to their side at an angle approximately parallel to the floor or as high as it can comfortably go without strain. The anterior shoulder point acts as the pivot for this movement, and the lateral epicondyle of the elbow is positioned outward, away from their torso. From the raised position, the patient lowers their arm back down towards the side of their body. The movement should be smooth and controlled, ensuring their arm stays in the same plane without forward or backward rotation.

The keypoints for the shoulder adduction range of motion measurement test may include the anterior shoulder point, the lateral epicondyle of the elbow and a vertical line perpendicular to the floor. The keypoint at the anterior shoulder point remains stationary, serving as the axis around which the arm adducts. The keypoint at the lateral epicondyle of the elbow, located at the elbow, moves downward in an arc as the arm is lowered. The trajectory of the lateral epicondyle helps in determining the extent of adduction. The vertical line perpendicular to the floor serves as a reference to assess how close the arm returns to the body's side, aiding in measuring the arm's vertical position relative to the torso.

The range of motion for shoulder adduction is quantified by the angle formed between the line created by the shaft of the humerus in the neutral position and a new line as it moves towards the midline of the body with the axis at the head of the humerus. As can be seen in FIG. 31C, the patient's right shoulder adduction range of motion is 47 degrees.

Figure 32A:
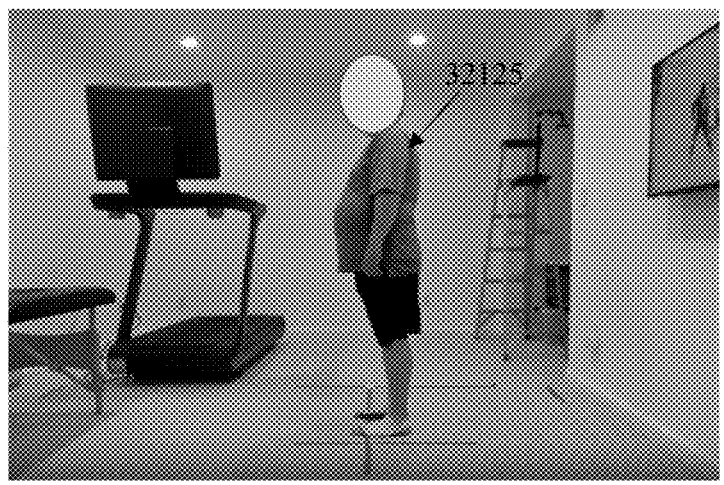
FIGS. 32A-32C illustrate the procedure for a patient performing a shoulder flexion range of motion measurement test, according to an aspect.
Figure 32B:
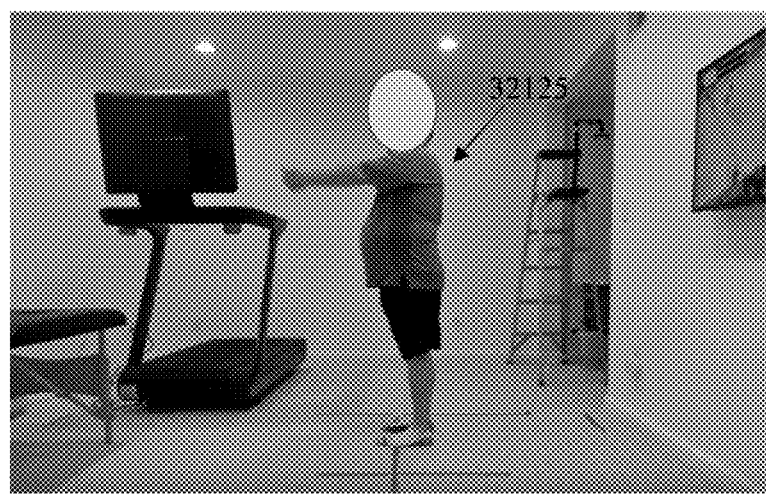
Figure 32C:
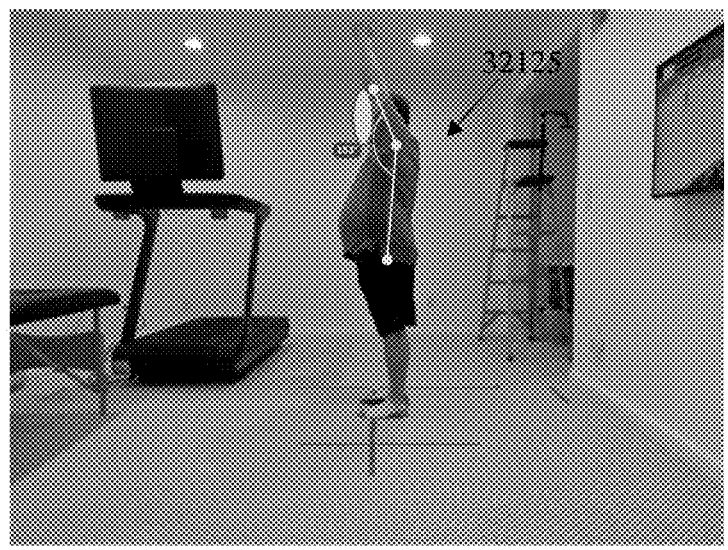

FIGS. 32A-32C illustrate the procedure for a patient 32125 performing a shoulder flexion range of motion measurement test, according to an aspect. Shoulder flexion is the movement where the patient's arm is raised forward from a position by the side of their body to a position in front, perpendicular to their torso, and potentially continuing towards a fully vertical position above their head. This movement is key for assessing the range of motion, strength, and health of the shoulder joint and its associated muscles.

For the shoulder flexion range of motion test, the patient 32125 may begin with their arm at their side, palm facing their body. The lateral shoulder point serves as the pivot for the movement, and the olecranon of the elbow (the prominent bone at the elbow) is aligned with the side of their body. The patient 32125 may then raise their arm forward, keeping their elbow straight if possible. The movement continues upward until their arm is in front of their body and as high as comfortably possible without straining, ideally reaching a position where their arm is vertical or near vertical.

The keypoints for the shoulder flexion range of motion measurement test may include the lateral shoulder point, the olecranon of the elbow and a vertical line perpendicular to the ground. The keypoint at the lateral shoulder point remains stationary, acts as the axis of rotation for the shoulder during the flexion. The keypoint at the olecranon of the elbow moves in a vertical arc, tracking the path of the elbow. This trajectory helps in determining the extent of the arm's elevation. The vertical line perpendicular with the floor is a reference line against which the final position of the arm can be measured, showing how far the arm has been raised in relation to a perpendicular stance.

The range of motion for shoulder flexion is quantified by measuring the line along the mid axillary line of the trunk and the line created by the shaft of the humerus in the neutral position with the axis at the head of the humerus with the new line created when moved into the flexion position. As can be seen in FIG. 32C, the patient's left shoulder flexion range of motion is 152 degrees.

Figure 33A:
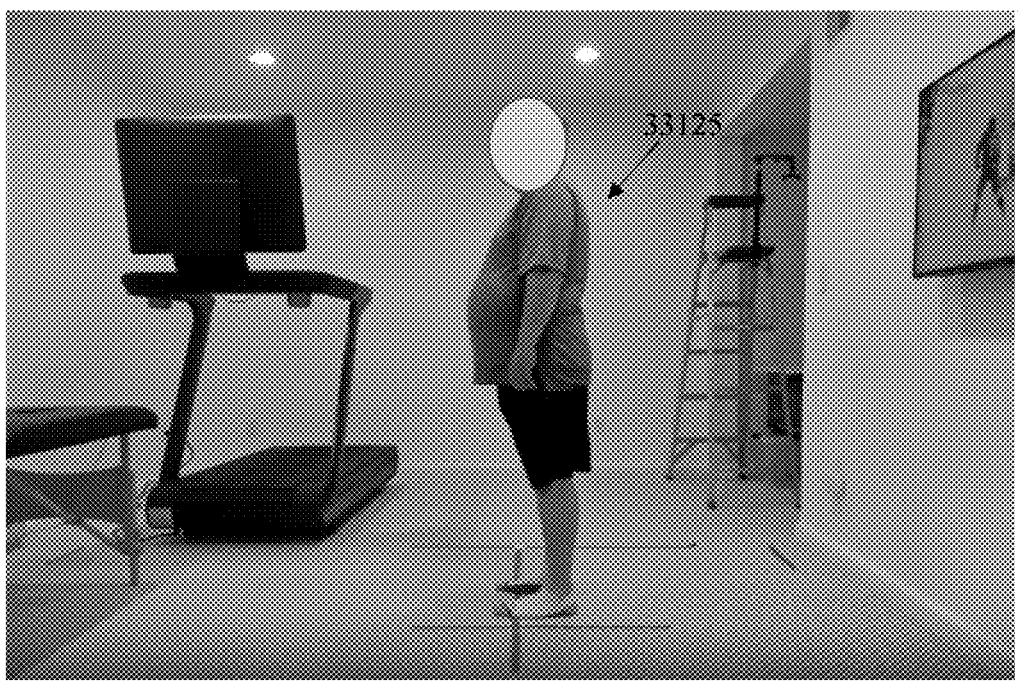
FIGS. 33A-33B illustrate the procedure for a patient performing a shoulder extension range of motion measurement test, according to an aspect.
Figure 33B:
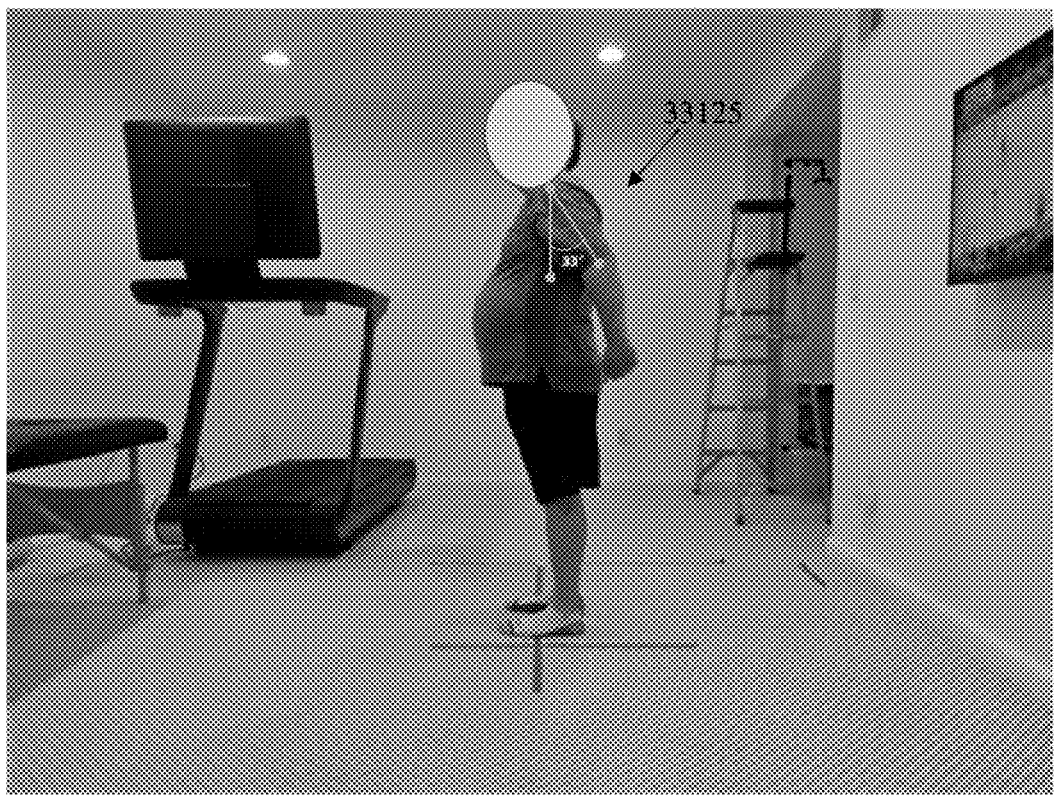

FIGS. 33A-33B illustrate the procedure for a patient 33125 performing a shoulder extension range of motion measurement test, according to an aspect. Shoulder extension is the movement where the patient's arm moves backward from a position by the side of the body, away from the front plane. This movement assesses the range of motion and strength of the posterior shoulder muscles and is vital for shoulder joint functionality.

For the shoulder extension range of motion test, the patient 33125 may begin with their arm at their side, palm facing their body. The lateral shoulder point serves as the pivot, and the lateral epicondyle of their elbow (located on the outer aspect of the elbow) is aligned with the side of their body. The patient may then move their arm backward, keeping their elbow straight. This motion is carried out until a comfortable limit is reached without forcing the movement or straining the muscles.

The keypoints for the shoulder extension range of motion measurement test may include the lateral shoulder point, the lateral epicondyle of the elbow and a vertical line to the floor. The keypoint at the lateral shoulder point remains stationary and acts as the axis of rotation for the shoulder during the extension. The keypoint at the lateral epicondyle of the elbow moves in a backward arc, as the arm extends back, and its path helps to determine the degree of extension. The vertical line perpendicular to the floor serves as a reference to measure how far the arm moves away from the body's front plane and towards the back.

The range of motion for shoulder extension is quantified by measuring the line along the mid axillary line of the trunk and the line created by the shaft of the humerus in the neutral position with the axis at the head of the humerus with the new line created when moved into the flexion position. As can be seen in FIG. 33B, the patient's left shoulder extension range of motion is 33 degrees.

Figure 34A:
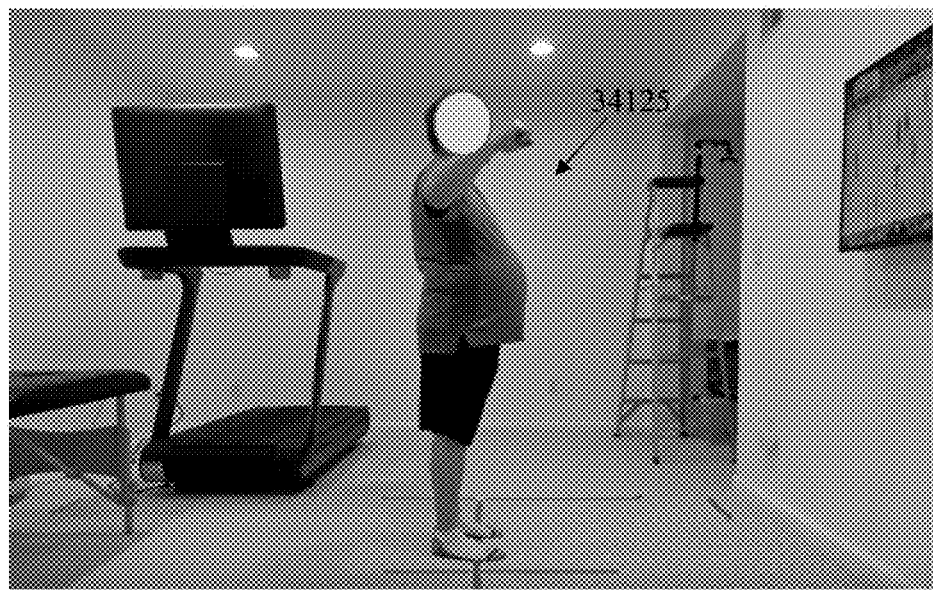
FIGS. 34A-34B illustrate the procedure for a patient performing a shoulder external rotation range of motion measurement test, according to an aspect.
Figure 34B:
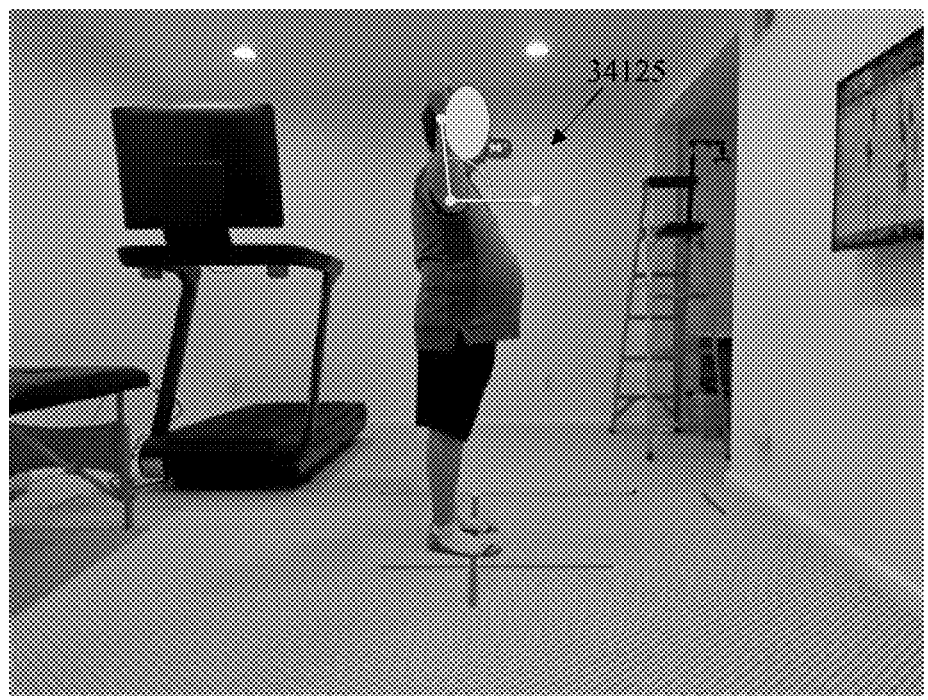

FIGS. 34A-34B illustrate the procedure for a patient 34125 performing a shoulder external rotation range of motion measurement test, according to an aspect. Shoulder external rotation is a movement where the patient's arm rotates outward at the shoulder joint, moving their forearm away from their body while their elbow is bent. This movement is crucial for assessing the rotational capacity and health of the shoulder's rotator cuff muscles and joint.

For the shoulder external rotation range of motion test, the patient 34125 may begin with the patient's elbow flexed at approximately 90 degrees, typically with their upper arm at their side, aligning their elbow with their torso. The olecranon process (the bony prominence of the elbow) should be pointing directly backward, and the wrist's styloid process should be in a neutral position. Next, while keeping their elbow bent and their upper arm stationary by their side, the patient may then rotate their forearm outward, away from their body. This rotation continues until their forearm reaches its maximum range without discomfort or compensatory body movements.

The keypoints for the shoulder external rotation range of motion measurement test may include the olecranon process of the elbow, the styloid process of the ulna at the wrist and a horizontal line parallel to the floor. The keypoint at the olecranon process of the elbow serves as a fixed pivot point and remains relatively stationary in terms of lateral movement, primarily providing a vertical reference for shoulder external rotation. The keypoint at the styloid process of the ulna at the wrist moves in an arc as the arm rotates externally, and its end position indicates the degree of external rotation. The horizontal line acts as a reference to assess the level of the styloid process during rotation. The movement of the wrist's styloid process above or below this line can provide additional insights into the range and symmetry of the motion.

The range of motion for shoulder external rotation is quantified by the angle formed between the initial and final positions of the forearm, relative to the horizontal line. As can be seen in FIG. 34B, the patient's right shoulder external rotation range of motion is 96 degrees.

Figure 35A:
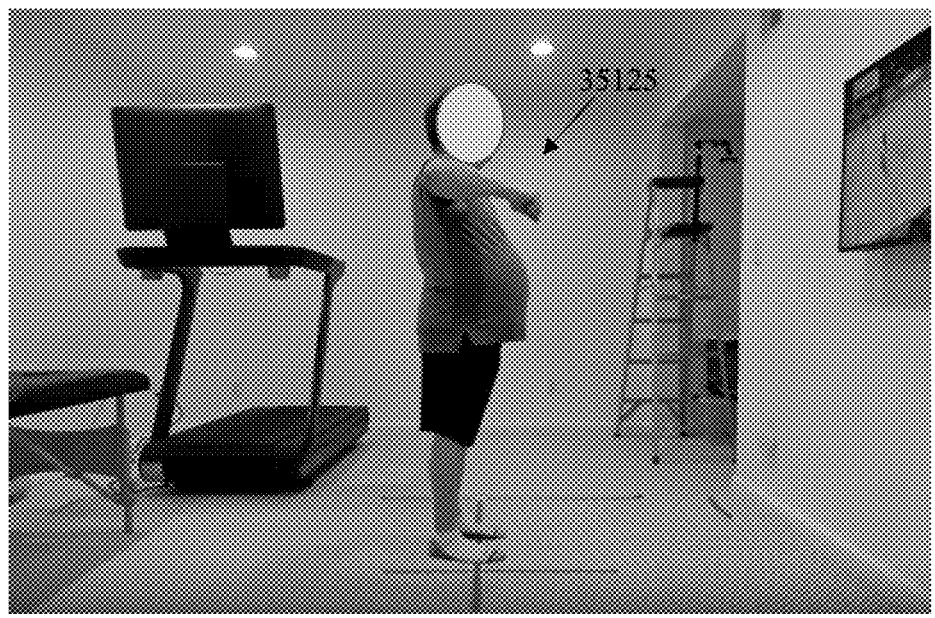
FIGS. 35A-35B illustrate the procedure for a patient performing a shoulder internal rotation range of motion measurement test, according to an aspect.
Figure 35B:
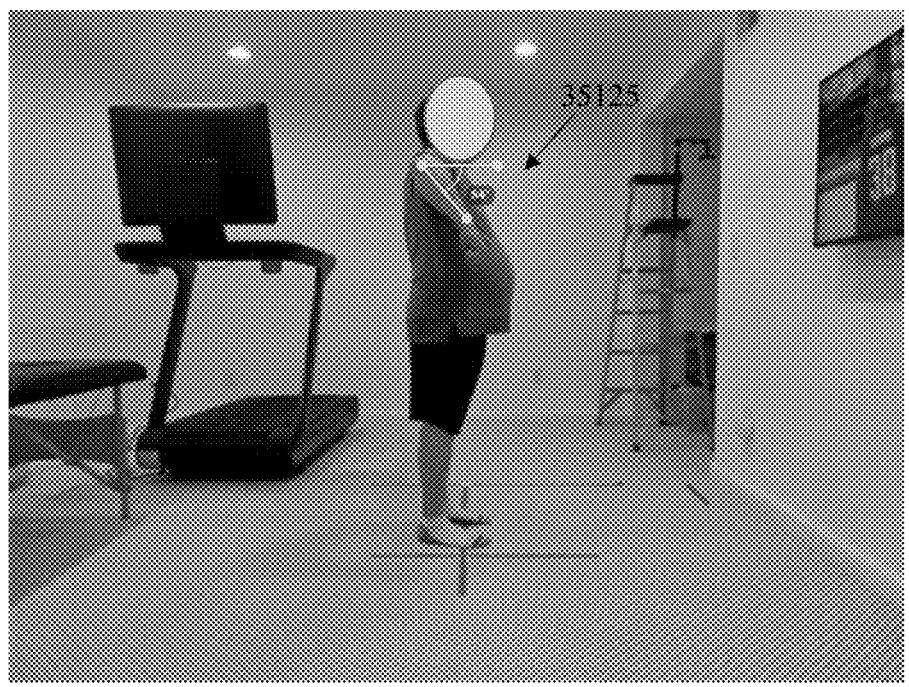

FIGS. 35A-35B illustrate the procedure for a patient 35125 performing a shoulder internal rotation range of motion measurement test, according to an aspect. Shoulder internal rotation is the movement where the patient's arm rotates inward toward their body at the shoulder joint, moving their forearm across the front of their body while keeping their elbow bent. This movement is key for evaluating the rotational capacity and health of the internal rotator muscles of the shoulder.

For the shoulder internal rotation range of motion test, the patient 35125 may begin with their elbow flexed at approximately 90 degrees, upper arm stabilized at their side, and forearm extended outward to begin in a neutral or slightly externally rotated position. This setup focuses the movement on the rotation at the shoulder joint. The lateral epicondyle of the elbow marks the outside of the elbow joint, while the styloid process of the ulna at the wrist indicates the lower end of the forearm. Then, while keeping their elbow bent and close to their body, the patient 35125 rotates their forearm inward, moving their hand toward the midline of their body. The movement should be smooth and controlled, stopping when a comfortable limit of internal rotation is reached, which is typically when their hand moves across their body to the opposite side or as far as it can comfortably go.

The keypoints for the shoulder internal rotation range of motion measurement test may include the lateral epicondyle of the elbow, the styloid process of the ulna at the wrist and a vertical line parallel to the floor. The keypoint at the lateral epicondyle of the elbow serves as a stationary reference point at the elbow, providing a center of rotation. The keypoint at the styloid process of the ulna at the wrist moves in a medial arc as the forearm rotates inward. Monitoring the path and endpoint of this point measures the extent of internal rotation. The horizontal line parallel to the floor acts as a baseline to ensure that the forearm remains horizontal during the measurement and helps to assess the movement trajectory of the wrist's styloid process accurately.

The range of motion for shoulder internal rotation is quantified by observing the angle between the initial position of the forearm and its final position relative to the horizontal line. As seen in FIG. 35B, the patient's right shoulder internal rotation range of motion is 54 degrees.

Figure 36A:
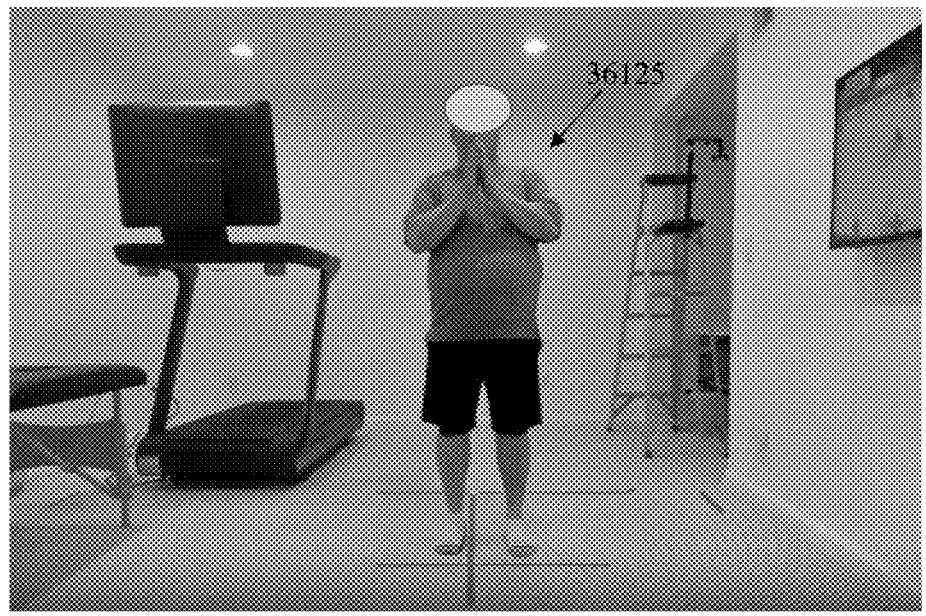
FIGS. 36A-36B illustrate the procedure for a patient performing a front view wrist extension range of motion measurement test, according to an aspect.
Figure 36B:
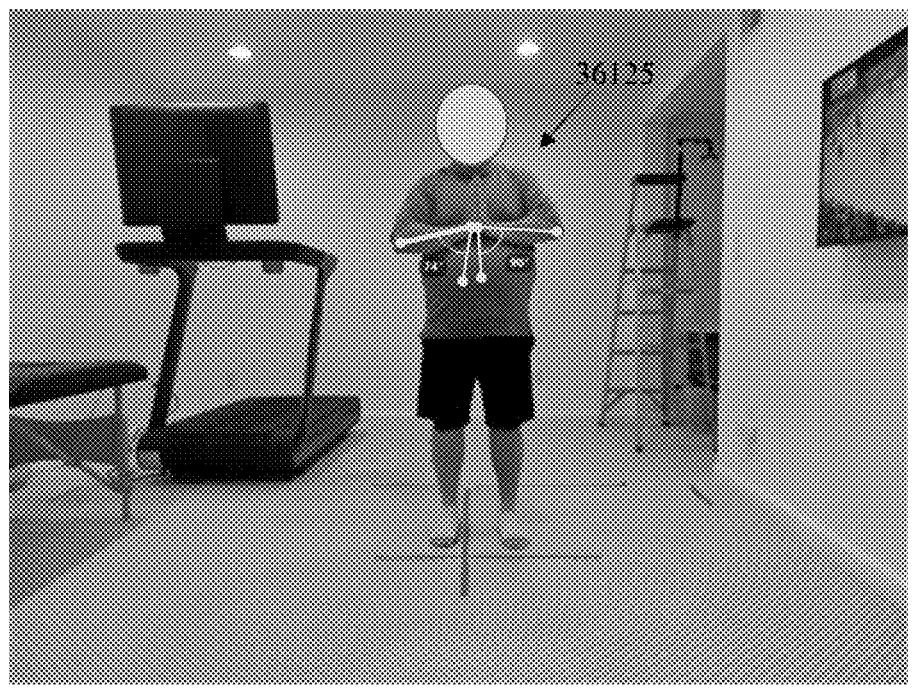

FIGS. 36A-36B illustrate the procedure for a patient 36125 performing a front view wrist extension range of motion measurement test, according to an aspect. Wrist extension is the movement where the back of the hand moves away from the forearm, increasing the angle between the hand and the forearm. This motion is key for evaluating the functionality and range of motion of the wrist joint, particularly important for actions that involve lifting or holding objects.

For the front view wrist extension range of motion test, the patient 36125 may begin with their forearm and wrist in a neutral position, extended straight out. Their palm should face downwards, and their fingers should be relaxed or slightly curled, depending on the specific requirements of the measurement setup. From the neutral position, the patient extends their wrist, moving the back of their hand upward, away from the forearm. The movement should be performed smoothly and controlled, focusing on isolating the movement to the wrist.

The keypoints for the front view wrist extension range of motion measurement test may include the lateral epicondyle of the elbow, the styloid process of the ulna and a line parallel with the $5^{th}$ metacarpal bone. The keypoint at the lateral epicondyle of the elbow serves as a fixed reference point from which wrist movement originates and can be tracked. The keypoint at the styloid process of the ulna acts as a clear marker for the movement of the wrist joint during extension. The line parallel to the $5^{th}$ metacarpal bone line helps in assessing the alignment and movement of the hand relative to the forearm, ensuring the measurement accurately tracks the motion of wrist extension without lateral deviation.

The range of motion for the front view wrist extension range of motion measurement test is quantified by measuring the angle between the forearm and a line extending parallel to the $5^{th}$ metacarpal bone from the wrist point, where one line aligns with the forearm (following the lateral epicondyle), and the other aligns with a line parallel to the 5th metacarpal, with the fulcrum positioned at the styloid process of the ulna. As seen in FIG. 36B, the patient's left and right wrist extension ranges of motion for the front view wrist extension range of motion measurement test are 90 degrees and 74 degrees, respectively.

Figure 37A:
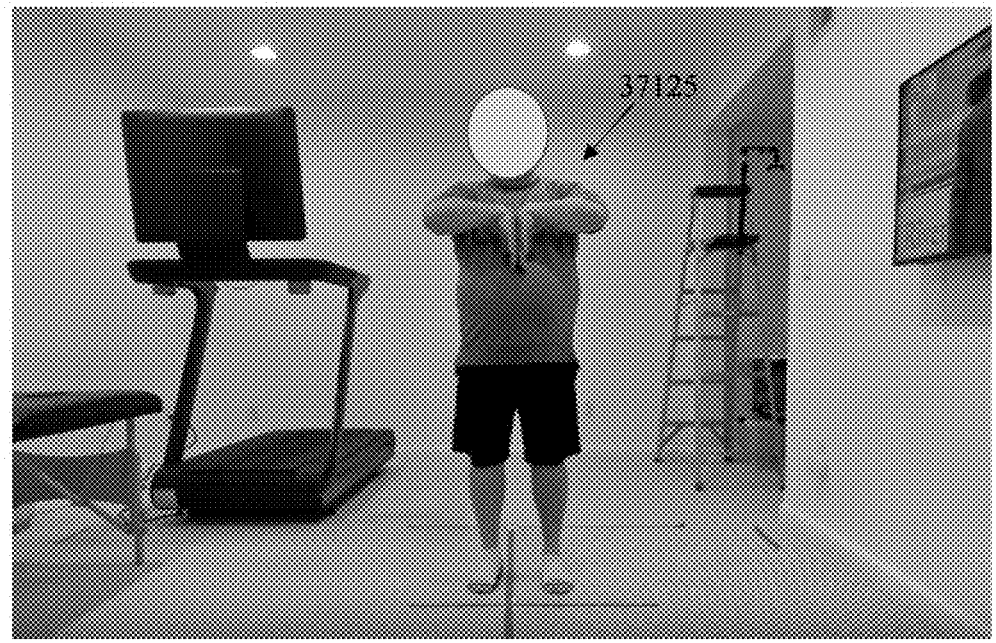
FIGS. 37A-37B illustrate the procedure for a patient performing a front view wrist flexion range of motion measurement test, according to an aspect.
Figure 37B:
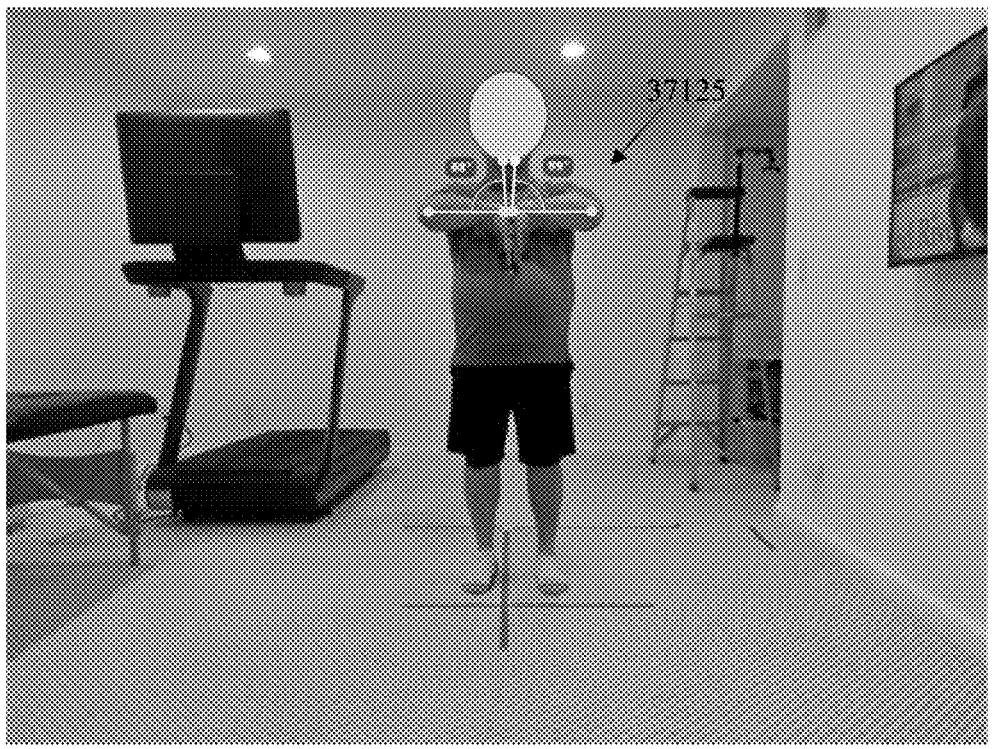

FIGS. 37A-37B illustrate the procedure for a patient 37125 performing a front view wrist flexion range of motion measurement test, according to an aspect. Wrist flexion is the movement where the palm of the hand moves towards the inner forearm, decreasing the angle between the hand and the forearm. This action is essential for evaluating the range of motion and functionality of the wrist joint.

For the front view wrist flexion range of motion test, the patient 37125 may begin with their forearm and wrist in a neutral position, extended straight out. Their palm should face downwards, and their fingers should be relaxed or slightly curled, depending on the specific measurement setup. From the starting position, the patient 37125 flexes their wrist, moving their hand downward towards the direction of the inner forearm. Their fingers can remain relaxed or slightly curled, and the movement should be smooth and controlled, focusing on isolating the movement to the wrist.

The keypoints for the front view wrist flexion range of motion measurement test may include the lateral epicondyle of the elbow, the styloid process of the ulna and a line parallel to the $5^{th}$ metacarpal bone. The keypoint at the lateral epicondyle of the elbow acts as a fixed reference point from which wrist movement originates and can be tracked. The keypoint at the styloid process of the ulna provides a clear marker for the movement of the wrist joint during flexion. The line parallel to the $5^{th}$ metacarpal bone helps in assessing the alignment and movement of the hand relative to the forearm, ensuring the measurement accurately tracks the motion of wrist flexion without lateral deviation.

The range of motion for the front view wrist flexion range of motion measurement test is quantified by measuring the angle between the forearm and a line extending parallel to the 5th metacarpal bone from the wrist point, where one line aligns with the forearm (following the lateral epicondyle), and the other aligns with a line parallel to the 5th metacarpal, with the fulcrum positioned at the styloid process of the ulna. As seen in FIG. 37B, the patient's left and right wrist flexion ranges of motion for the front view wrist flexion range of motion measurement test are 89 degrees and 88 degrees, respectively.

Figure 38A:
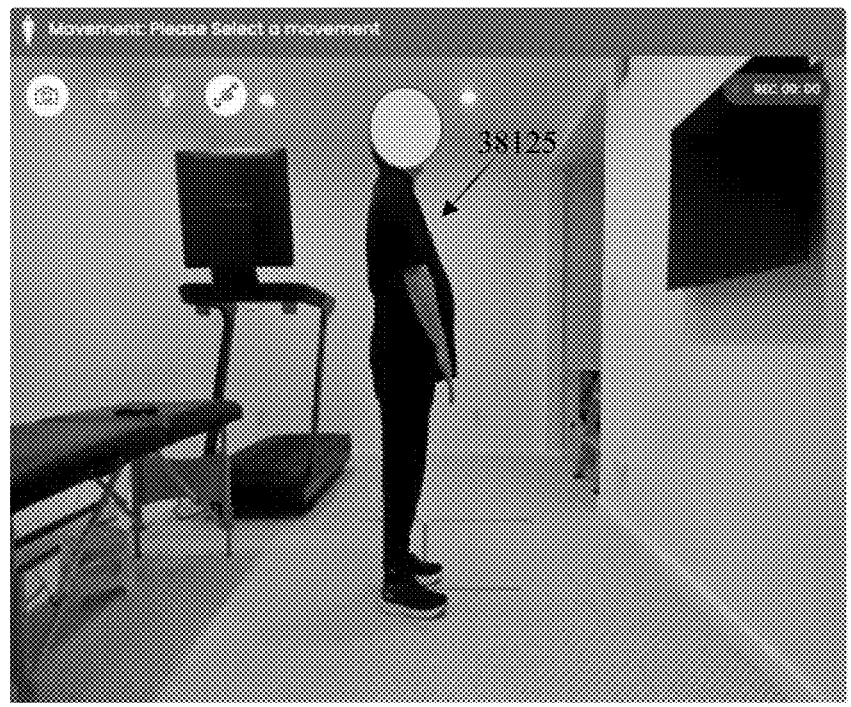
FIGS. 38A-38B illustrate the procedure for a patient performing a side view elbow flexion range of motion measurement test, according to an aspect.
Figure 38B:
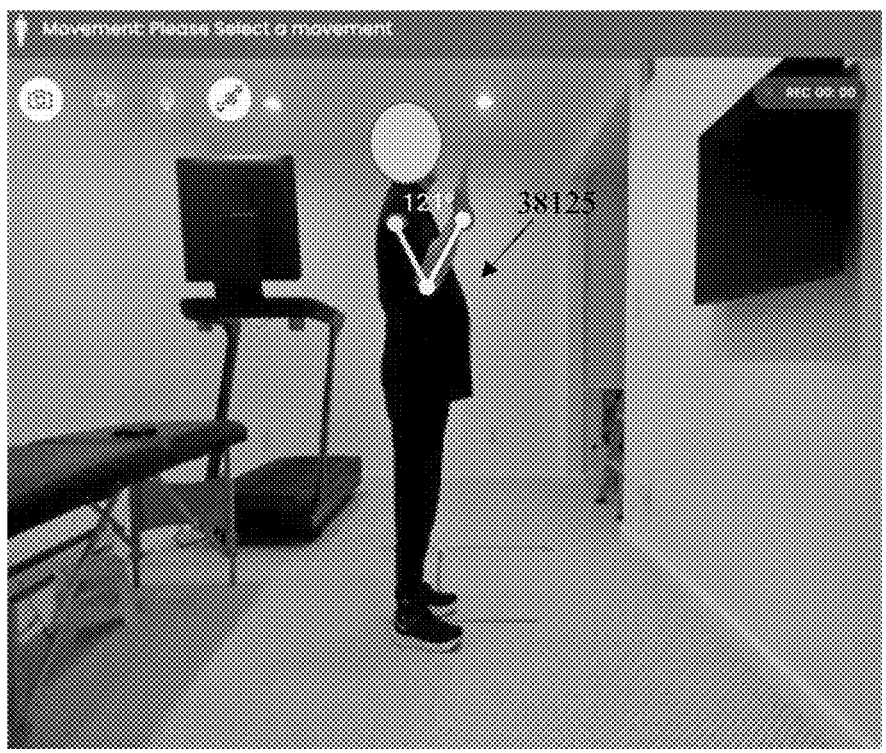

FIGS. 38A-38B illustrate the procedure for a patient 38125 performing a side view elbow flexion range of motion measurement test, according to an aspect. Elbow flexion is the movement where the forearm is bent towards the upper arm, decreasing the angle at the elbow joint. It is a fundamental movement for assessing the functionality and range of motion of the elbow.

For the side view elbow flexion range of motion test, the patient 38125 may begin with their arm extended straight along their side, with their elbow fully extended and their palm facing forward. This position allows clear visibility and measurement of the key anatomical landmarks. The patient 38125 then flexes their elbow, bringing their forearm up towards their shoulder. The movement is smooth and controlled, ideally keeping the upper arm stationary, to isolate the movement to the elbow joint.

The keypoints for the side view elbow flexion range of motion measurement test may include the anterior head of the humerus, the medial epicondyle of the humerus and the styloid process of the ulna at the wrist. The keypoint at the anterior head of the humerus serves as the proximal reference point at the upper arm, indicating the base of the movement. The keypoint at the medial epicondyle of the humerus acts as a central pivot point for the movement, providing a clear marker for the degree of flexion at the elbow. The keypoint at the styloid process of the ulna at the wrist moves in an arc as the elbow is flexed. The path and endpoint of the styloid process are crucial for determining the extent of the forearm's movement during flexion.

The range of motion for the side view elbow flexion range of motion measurement test is quantified by measuring the angle formed between the upper arm and the forearm at the point of maximum flexion, where the fulcrum is where the upper arm joins with the forearm and one line aligns with the shaft of the humerus, and the other aligns with the shaft of the ulna. As seen in FIG. 38B, the patient's right elbow flexion range of motion for the side view elbow flexion range of motion measurement test is 121 degrees.

Figure 39A:
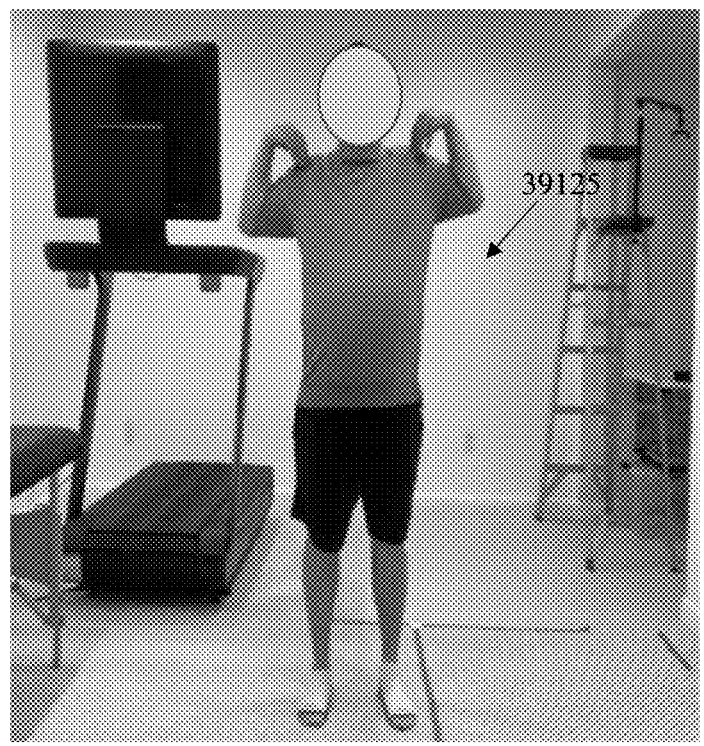
FIGS. 39A-39B illustrate the procedure for a patient performing an elbow extension range of motion measurement test, according to an aspect.
Figure 39B:
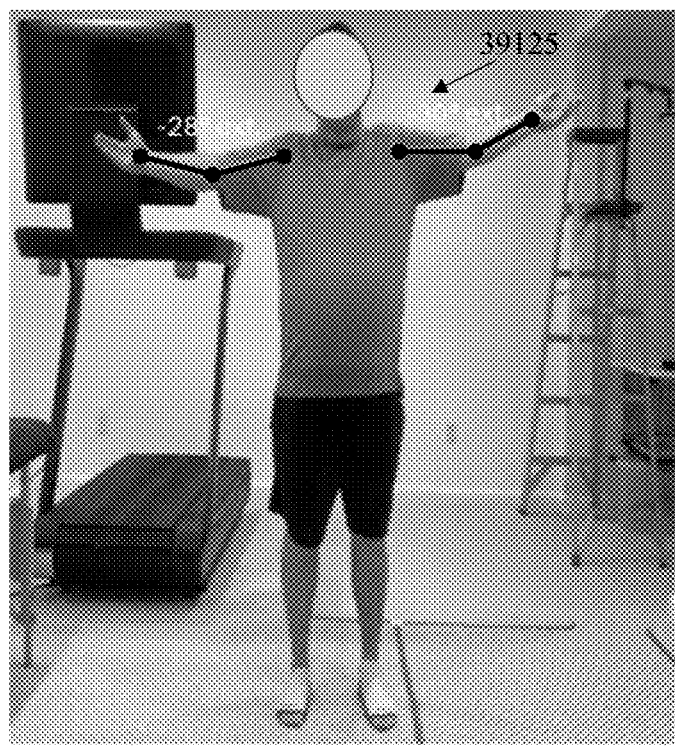

FIGS. 39A-39B illustrate the procedure for a patient 39125 performing an elbow extension range of motion measurement test, according to an aspect. Elbow extension is the movement where the patient moves their forearm away from their upper arm, straightening the elbow joint. This action is crucial for assessing the functionality and range of motion of the elbow.

For the elbow extension range of motion test, the patient 39125 may begin with their elbow in a flexed position, typically with their forearm and hand oriented towards their shoulder. This can be performed either seated or standing, ensuring the upper arm remains stationary and aligned with the torso. From the flexed position, the patient 39125 extends their forearm away from their upper arm, moving towards a straightened position. The movement should be controlled and smooth, ideally without moving the upper arm to isolate the extension at the elbow.

The keypoints for the elbow extension range of motion measurement test may include the lateral epicondyle of the humerus, the lateral head of the humerus and the styloid process of the radius. The keypoint at the lateral epicondyle of the humerus serves as a pivot point for the movement of the elbow joint. The keypoint at the lateral head of the humerus provides a reference point at the upper arm, near the shoulder, helping to assess the alignment and stability of the arm during the movement. The keypoint at the styloid process of the radius moves as the forearm extends. Tracking the path and endpoint of the styloid process is crucial for measuring the extent of the elbow extension.

The range of motion for elbow extension is quantified by measuring the angle formed between the upper arm and the forearm at the point of maximum flexion, where the fulcrum is where the upper arm joins with the forearm and one line aligns with the shaft of the humerus, and the other aligns with the shaft of the ulna. As seen in FIG. 39B, the patient's left and right elbow extension ranges of motion are −30 degrees and −28 degrees, respectively.

Figure 40A:
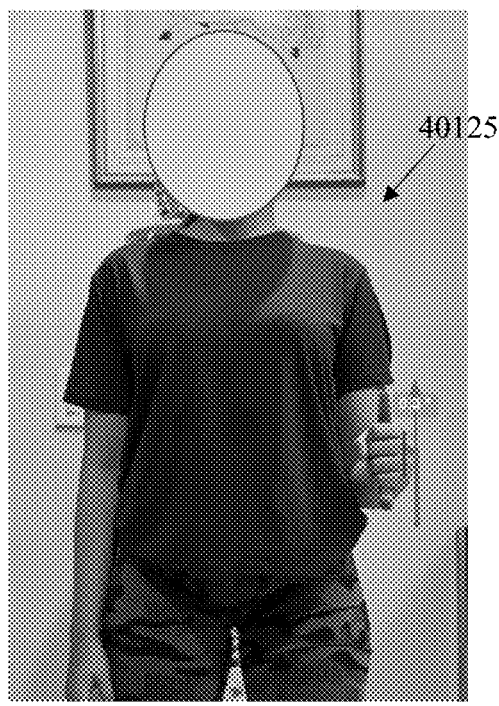
FIGS. 40A-40B illustrate the procedure for a patient performing a forearm pronation range of motion measurement test, according to an aspect.
Figure 40B:
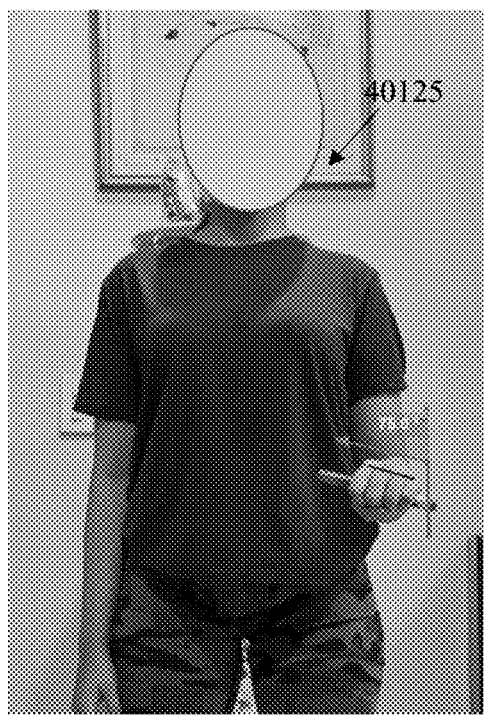

FIGS. 40A-40B illustrate the procedure for a patient 40125 performing a forearm pronation range of motion measurement test, according to an aspect. Forearm Pronation is the rotational movement of the forearm that turns the palm downward when the elbow is at a 90-degree angle. This movement is critical for assessing the range of motion and functionality of the forearm's rotational muscles and joints.

For the forearm pronation range of motion test, the patient 40125 may begin with their forearm extended and their elbow flexed at 90 degrees, ensuring that their forearm and wrist are in a neutral position. Their palm should face upwards or towards their body. From the neutral position, the patient 40125 rotates their forearm to turn their palm downward, moving towards full pronation. This movement is executed without altering the position of the wrist, which remains in a neutral stance throughout.

The keypoints for the forearm pronation range of motion measurement test may include an initial reference line, a second reference line done before the movement and a new line done after the movement. The initial reference line is drawn between the 3rd and 4th metacarpal heads and the center of the wrist. This initial reference line serves as a baseline measurement to establish the starting orientation of the hand relative to the forearm. The second reference line is between the 5th metacarpal head and the 2nd metacarpal head before movement. This second reference line provides a reference for the initial lateral spread of the hand before pronation. The new line is drawn between the 5th metacarpal head and the 2nd metacarpal head after rotating the forearm to full pronation. This new line indicates the change in position of these points relative to the forearm, reflecting the degree of pronation achieved.

The range of motion for forearm pronation is quantified by measuring the change in the angle between the line drawn between the $2^{nd}$ and $5^{th}$ metacarpal heads and a new line formed after rotating the fist medially with the axis being at the center point between the 3rd and 4th metacarpal heads. As seen in FIG. 40B, the patient's left forearm pronation range of motion is 75.0 degrees.

Figure 41A:
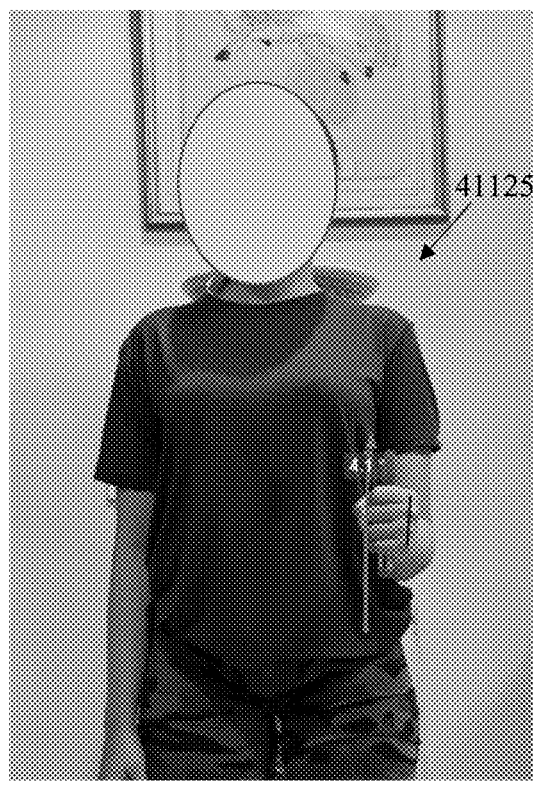
FIGS. 41A-41B illustrate the procedure for a patient performing a forearm supination range of motion measurement test, according to an aspect.
Figure 41B:

FIGS. 41A-41B illustrate the procedure for a patient 41125 performing a forearm supination range of motion measurement test, according to an aspect. Forearm supination is the rotational movement of the forearm that turns the palm upward when the elbow is flexed at a 90-degree angle. This movement is crucial for assessing the range of motion and functionality of the forearm's supinator muscles and the joints involved in rotation.

For the forearm supination range of motion test, the patient 41125 may begin with their forearm extended and their elbow flexed at 90 degrees, ensuring that their forearm and wrist are in a neutral position. Their palm should start facing downwards or towards their body if starting from a pronated position. From the initial position, the patient 41125 rotates their forearm to turn their palm upward, moving towards full supination. This movement should be executed without altering the position of the wrist, which remains neutral throughout the rotation.

The keypoints for the forearm supination range of motion measurement test may include an initial reference line, a second reference line before movement and a new line after movement. The initial reference line is between the 3rd and 4th metacarpal heads and the center of the wrist. This initial reference line serves as a baseline to establish the starting orientation of the hand relative to the forearm. The second reference line is between the 5th metacarpal head and the 2nd metacarpal head before rotation. This second reference line provides a reference for the initial lateral orientation of the hand before supination. The new line is drawn between the 5th metacarpal head and the 2nd metacarpal head after rotating the forearm to full supination. This new line indicates the change in position of these points relative to the forearm, reflecting the degree of supination achieved.

The range of motion for forearm supination is quantified by measuring the change in the angle between the line drawn between the 2nd and 5th metacarpal heads and a new line formed after rotating the fist medially with the axis being at the center point between the 3rd and 4th metacarpal heads. As seen in FIG. 41B, the patient's left forearm supination range of motion is 102.6 degrees.

Figure 42A:
FIGS. 42A-42B illustrate the procedure for a patient performing a side view wrist flexion range of motion measurement test, according to an aspect.
Figure 42B:

FIGS. 42A-42B illustrate the procedure for a patient 42125 performing a side view wrist flexion range of motion measurement test, according to an aspect. Wrist flexion is the movement where the palm of the patient's hand moves towards their inner forearm, decreasing the angle between the hand and the forearm. This movement is essential for assessing the range of motion and functionality of the wrist joint.

For the side view wrist flexion range of motion test, the patient 42125 may begin with the patient's forearm and wrist in a neutral position, extended straight out. Their palm should face downwards or sideways depending on the comfort of the patient 42125. From the starting position, the patient 42125 flexes their wrist, moving their hand downward towards the direction of their inner forearm. Their fingers can remain relaxed or slightly curled, and the movement should be smooth and controlled.

The keypoints for the side view wrist flexion range of motion measurement test may include the lateral aspect of the styloid process of the ulna (wrist point), the 5$^{th}$ metacarpal head and the midline of the lateral ulnar. The keypoint at the lateral aspect of the styloid process of the ulna acts as a fixed reference point from which wrist movement originates and can be tracked. The keypoint at the 5$^{th}$ metacarpal head moves as the hand flexes downward, providing a clear indication of the hand's displacement relative to the forearm. The keypoint at the midline of the lateral ulnar serves to measure the alignment and the angle change of the forearm to the hand.

The range of motion for the side view wrist flexion range of motion measurement test is quantified by measuring the angle between the forearm and a line extending through midline of the 5th metacarpal bone from the wrist point, with the fulcrum positioned at the styloid process of the ulna. As seen in FIG. 42B, the patient's right wrist flexion range of motion for the side view wrist flexion range of motion measurement test is 58 degrees.

Figure 43A:
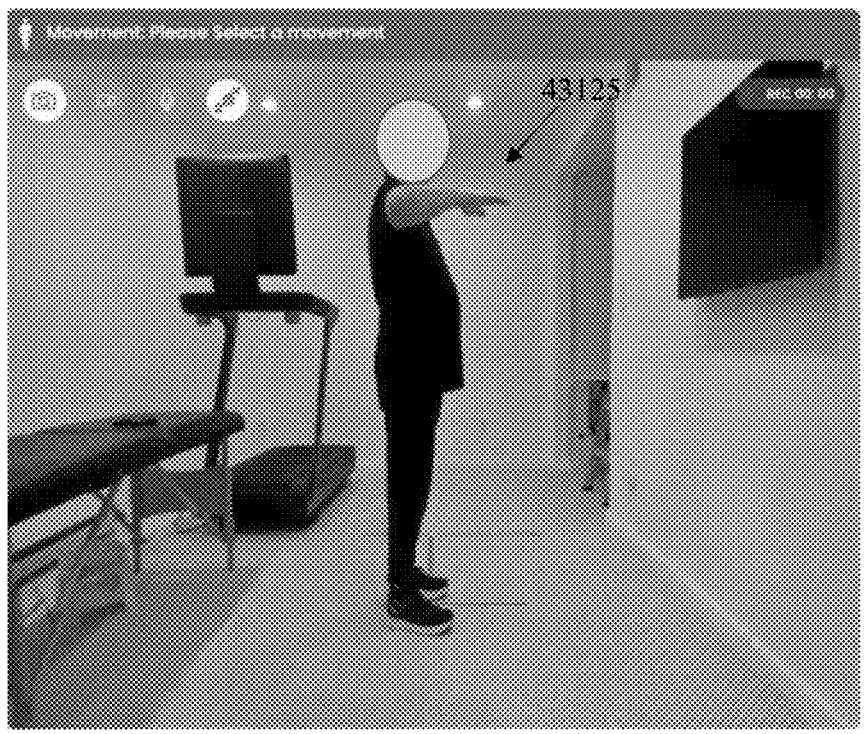
FIGS. 43A-43B illustrate the procedure for a patient performing a side view wrist extension range of motion measurement test, according to an aspect.
Figure 43B:
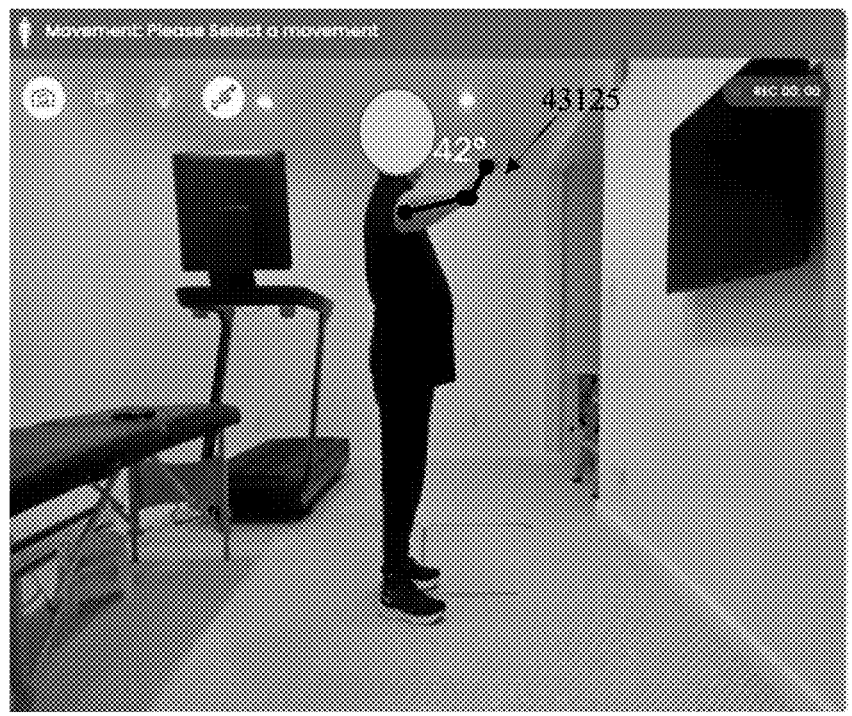

FIGS. 43A-43B illustrate the procedure for a patient 43125 performing a side view wrist extension range of motion measurement test, according to an aspect. Wrist extension is the movement where the back of the hand moves away from the forearm, increasing the angle between the hand and the forearm. This motion is key for evaluating the functionality and range of motion of the wrist joint, which is essential for various everyday activities and specific tasks that require lifting or holding objects.

For the side view wrist extension range of motion test, the patient 43125 may begin with their forearm and wrist in a neutral position, extended straight out. Their palm should face downwards, and their fingers should be relaxed or slightly curled, depending on the specific requirements of the measurement setup. From the neutral position, the patient 43125 extends their wrist, moving the back of their hand upward, away from their forearm. The movement should be performed smoothly and controlled, focusing on isolating the movement to the wrist.

The keypoints for the side view wrist extension range of motion measurement test may include the lateral aspect of the styloid process of the ulna, the 5$^{th}$ metacarpal head, and the midline of the lateral ulnar. The keypoint at the lateral aspect of the styloid process of the ulna serves as a fixed reference point from which the movement of the wrist originates and can be tracked accurately. The keypoint at the 5$^{th}$ metacarpal head provides a clear indicator of the hand's displacement relative to the forearm. The keypoint at the midline of the lateral ulnar (a line along the lateral side of the ulna) serves to measure the alignment and the angle change of the forearm relative to the hand.

The range of motion for the side view wrist extension range of motion measurement test is quantified by measuring the angle between the forearm and a line extending through midline of the 5th metacarpal bone from the wrist point, with the fulcrum positioned at the styloid process of the ulna. As seen in FIG. 43B, the patient's right wrist extension range of motion for the side view wrist extension range of motion measurement test is 42 degrees.

Figure 44A:
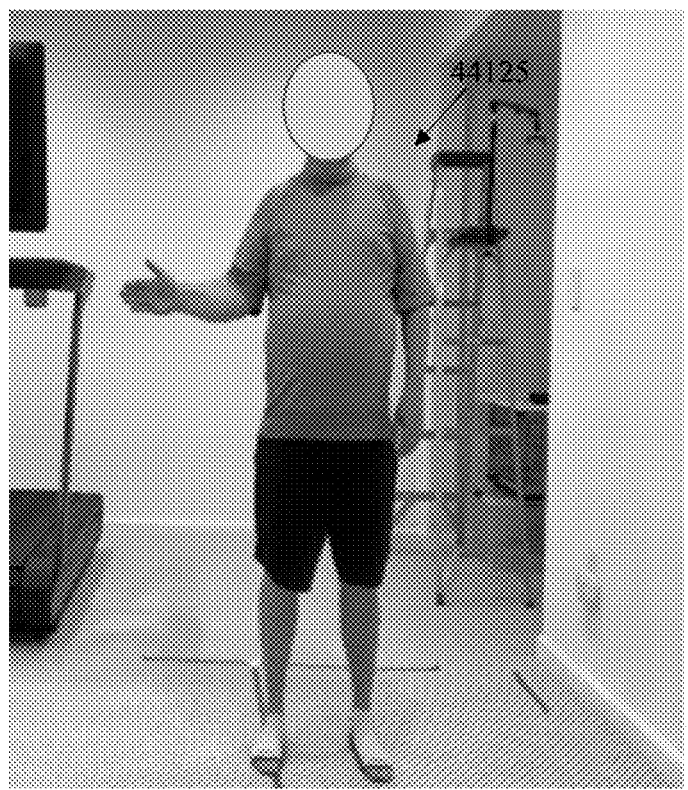
FIGS. 44A-44B illustrate the procedure for a patient performing an ulnar deviation range of motion measurement test, according to an aspect.
Figure 44B:
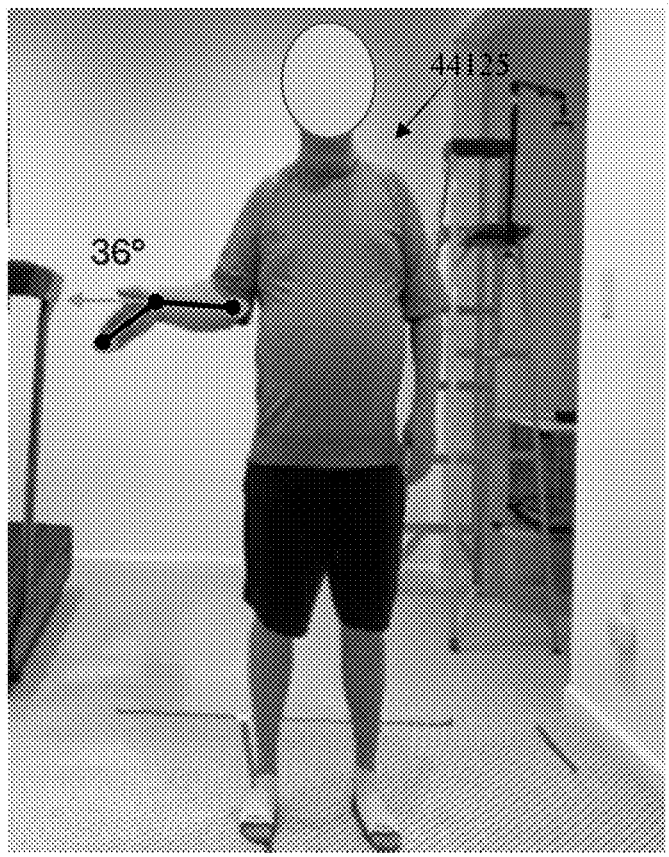

FIGS. 44A-44B illustrate the procedure for a patient 44125 performing an ulnar deviation range of motion measurement test, according to an aspect. Ulnar deviation, also known as ulnar flexion, is the movement where the hand moves towards the ulnar side (towards the little finger side) of the forearm. This action is crucial for assessing the range of motion and health of the wrist joint, particularly the ligaments and tendons on the medial side of the wrist.

For the ulnar deviation range of motion test, the patient 44125 may begin with their forearm extended and their wrist in a neutral position, typically with their palm facing downwards or sideways towards their body. From the starting position, the patient 44125 moves their hand towards the ulnar side, effectively bringing the hand closer to the forearm's ulnar side. Their fingers can remain relaxed or slightly curled, and the movement should be smooth and controlled, focusing on isolating the movement to the wrist.

The keypoints for the ulnar deviation range of motion measurement test may include the center of the wrist between the ulnar and the radial styloid processes, the dorsal midline of the forearm, and the head of the third metacarpal. The keypoint at the center of the wrist between the ulnar and radial styloid processes acts as a pivot for the wrist movement, situated centrally at the wrist and serving as a primary reference for the direction and extent of the deviation. The keypoint at the dorsal midline of the forearm provides a consistent baseline for evaluating the wrist's movement in the form of a reference line along the back of the forearm helps ensure that the forearm remains in a neutral, stable position during the measurement. The keypoint at the head of the third metacarpal moves laterally towards the ulnar side during the test. Tracking the displacement of this metacarpal head provides a clear measure of how far the wrist deviates.

The range of motion for ulnar deviation is quantified by measuring the angle between the dorsal midline of the forearm and a line extending from the center of the wrist through the head of the 3rd metacarpal, where one line aligns with the dorsal midline of the forearm, and the other aligns with the trajectory of the 3rd metacarpal, with the fulcrum positioned at the center of the wrist. As seen in FIG. 44B, the patient's right ulnar deviation range of motion is 36 degrees.

Figure 45A:
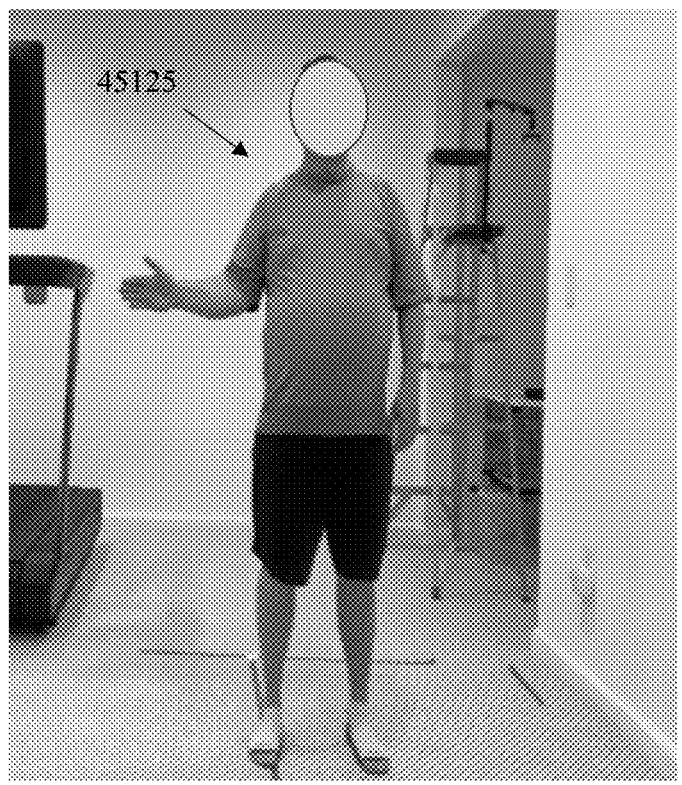
FIGS. 45A-45B illustrate the procedure for a patient performing a radial deviation range of motion measurement test, according to an aspect.
Figure 45B:
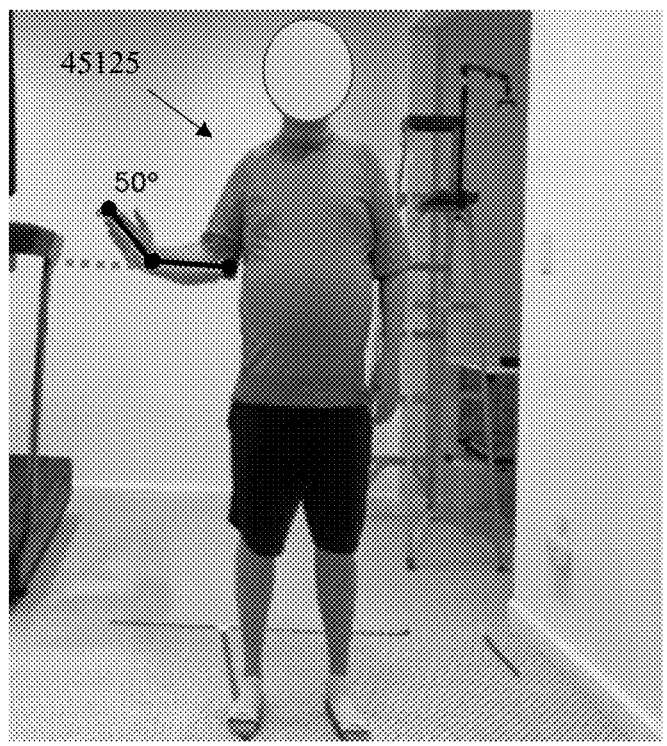

FIGS. 45A-45B illustrate the procedure for a patient 45125 performing a radial deviation range of motion measurement test, according to an aspect. Radial deviation, also known as radial flexion, is the movement where the hand moves towards the radial side (towards the thumb side) of the forearm. This action is important for assessing the range of motion and functionality of the wrist joint, particularly focusing on the lateral (thumb side) structures of the wrist.

For the radial deviation range of motion test, the patient 45125 may begin with their forearm extended and their wrist in a neutral position, typically with their palm facing downwards or sideways towards their body. From the starting position, the patient 45125 moves their hand towards their radial side, effectively bringing the hand closer to the forearm's radial side. Their fingers are fully extended, and the movement should be smooth and controlled, focusing on isolating the movement to the wrist.

The keypoints for the radial deviation range of motion measurement test may include the center of the wrist between the ulnar and the radial styloid processes, the dorsal midline of the forearm and the head of the 3$^{rd}$ metacarpal. The keypoint at the center of the wrist between the ulnar and radial styloid processes serves as the pivot for the wrist movement, located centrally at the wrist and providing a primary reference for the direction and extent of the deviation. The keypoint at the dorsal midline of the forearm provides a consistent baseline for evaluating the wrist's movement. The keypoint at the head of the 3$^{rd}$ metacarpal moves laterally towards the radial side during the test. Tracking the displacement of this metacarpal head provides a clear measure of how far the wrist deviates.

The range of motion for radial deviation is quantified by measuring the angle between the dorsal midline of the forearm and a line extending from the center of the wrist through the midline of the 3rd metacarpal bone, with the fulcrum positioned at the center of the wrist. As seen in FIG. 45B, the patient's right radial deviation range of motion is 50 degrees. The disclosed range of motion tests described in FIGS. 29A-45B may be classified as arm/upper extremities range of motion tests, for simplicity. These arm/upper extremity range of motion tests may be performed as part of an arm/upper extremity assessment, similarly to the hereinabove described gait assessment. Furthermore, by performing this described upper extremity assessment, the MMH system may be configured to generate an upper extremity diagnosis by evaluating the resultant range of motion values to assess and suitably report a patient's MSK health within their upper extremities region.

Figure 46A:
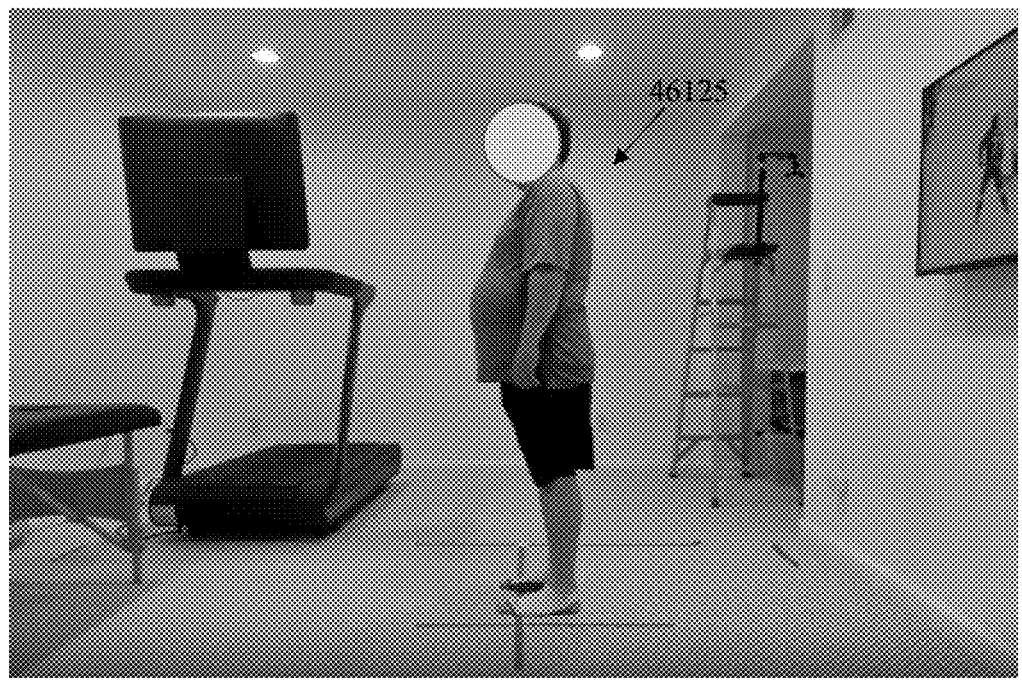
FIGS. 46A-46B illustrate the procedure for a patient performing a hip flexion range of motion measurement test, according to an aspect.
Figure 46B:
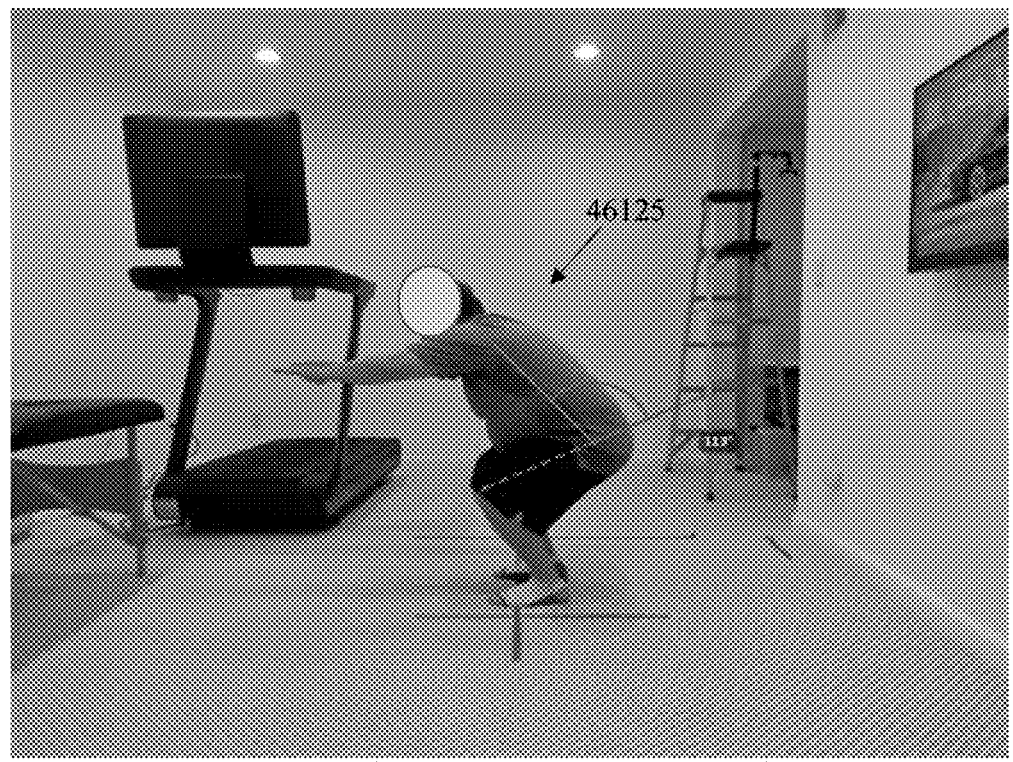

FIGS. 46A-46B illustrate the procedure for a patient 46125 performing a hip flexion range of motion measurement test, according to an aspect. Hip flexion is the movement where the thigh is brought towards the torso, decreasing the angle between the thigh and the pelvis. This movement is crucial for assessing the range of motion and the health of the hip joint. The lateral head of the humerus is utilized as a starting point for measurements, providing a comprehensive reference for overall body posture or as a static point in AI calculations.

For the hip flexion range of motion test, the patient 46125 may begin in a standing or lying position with their legs extended straight. If standing, balance support may be necessary. Next, The patient 46125 flexes their hip by lifting their knee and thigh upwards towards their chest. This movement should be performed smoothly, keeping the knee either bent or straight, depending on the specific assessment requirement.

The keypoints for the hip flexion range of motion measurement test may include the lateral head of the humerus, the lateral head of the femur and the lateral condyle of the femur. The keypoint at the lateral head of the humerus is used as an additional reference for upper body posture or as a static reference point in AI models, ensuring upper body stability or alignment during hip extension. The keypoint at the lateral head of the femur serves as a proximal reference point near the hip joint, indicating the base of the movement. The keypoint at the lateral condyle of the femur acts as a distal landmark that moves closer to the body as the hip is flexed. Its path provides an indication of how much the leg is lifted.

The range of motion for hip flexion is quantified by measuring the angle formed between the torso and the thigh at the point of maximum flexion, where one line aligns with the torso and the other extends along the lateral aspect of the thigh, with the pivot point over the hip joint. As seen in FIG. 46B, the patient's hip flexion range of motion is 113 degrees.

Figure 47A:
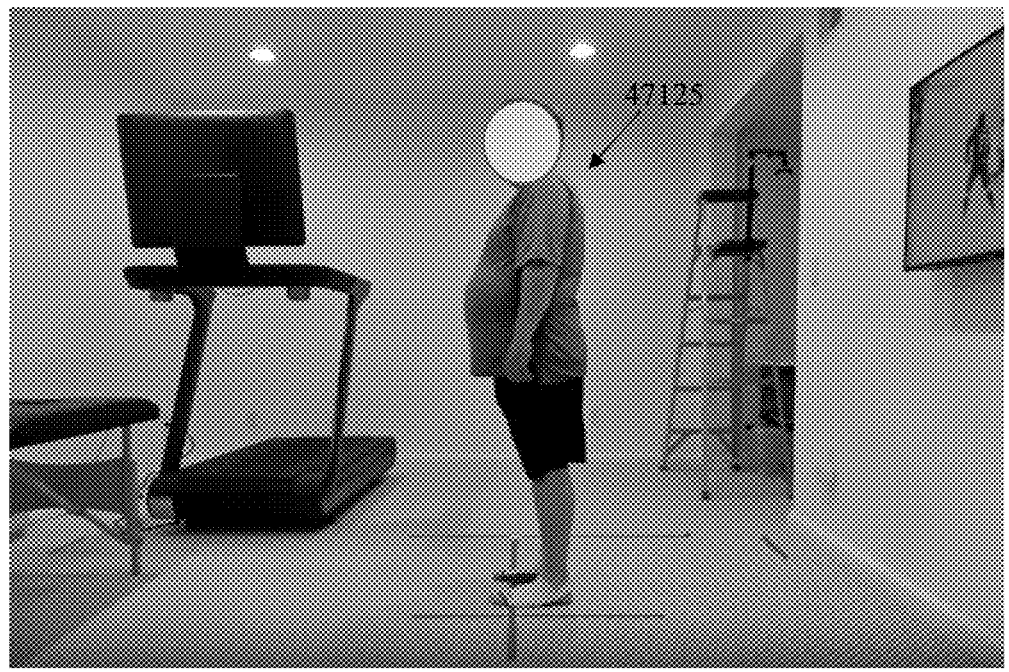
FIGS. 47A-47B illustrate the procedure for a patient performing a hip extension range of motion measurement test, according to an aspect.
Figure 47B:
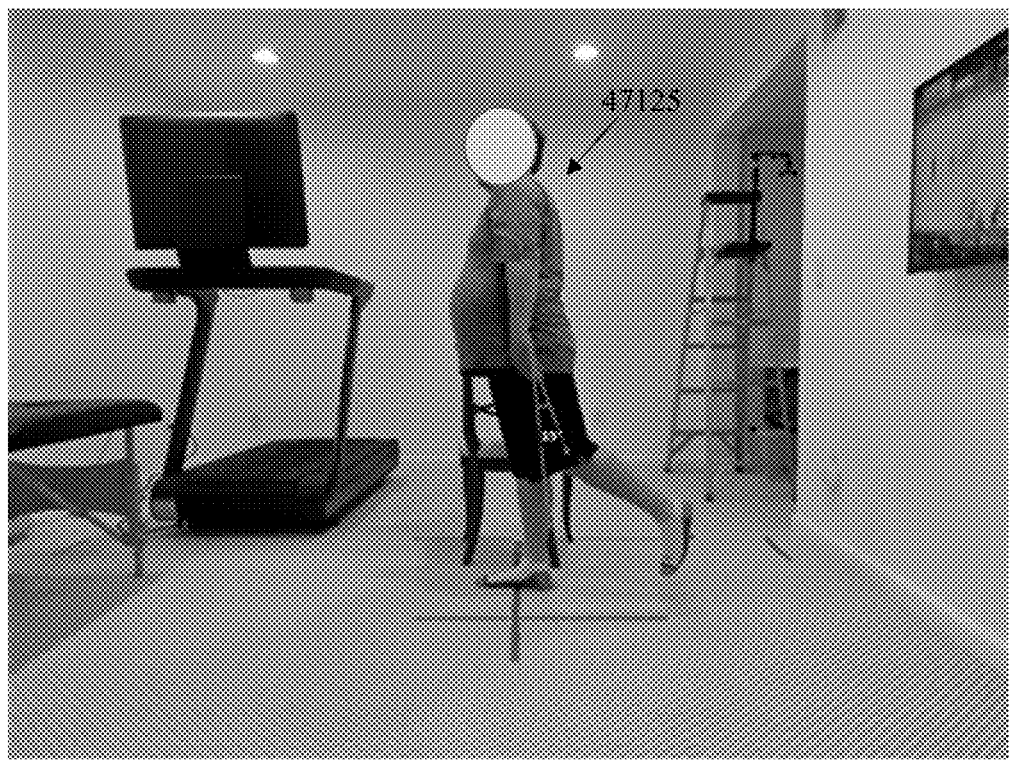

FIGS. 47A-47B illustrate the procedure for a patient 47125 performing a hip extension range of motion measurement test, according to an aspect. Hip extension is the movement where the thigh moves backward from the body, increasing the angle between the thigh and the pelvis. This is a fundamental movement for assessing the functionality and range of motion of the hip joint, crucial for walking, running, and many other activities. The lateral head of the humerus is utilized as a starting point for measurements, providing a comprehensive reference for overall body posture or as a static point in AI calculations.

For the hip extension range of motion test, the patient 47125 may begin standing straight with their feet together, or lying face down if the measurement is to be taken in a prone position. Their body should be aligned, with their legs straight and arms relaxed at their sides. From the starting position, the patient 47125 extends their hip by moving their leg backward without bending their knee. The movement should be controlled, avoiding any rotation or lateral movement of the pelvis to isolate the hip extension.

The keypoints for the hip extension range of motion measurement test may include the lateral head of the humerus, the lateral head of the femur, and the lateral condyle of the femur. The keypoint at the lateral head of the humerus is used as an additional reference for upper body posture or as a static reference point in AI models, ensuring upper body stability or alignment during hip extension. The keypoint at the lateral head of the femur acts as the main pivot point near the hip joint, serving as the base of the movement. The keypoint at the lateral condyle of the femur moves backward as the hip extends, providing a clear indication of the leg's displacement relative to the pelvis.

The range of motion for hip extension is quantified by measuring the angle between the torso and the thigh at the maximum extension point. This measurement is done with the individual in a standing position, where one line aligns with the torso and the other extends along the lateral aspect of the thigh, with the fulcrum over the hip joint. As seen in FIG. 47B, the patient's hip extension range of motion is 15 degrees.

Figure 48A:
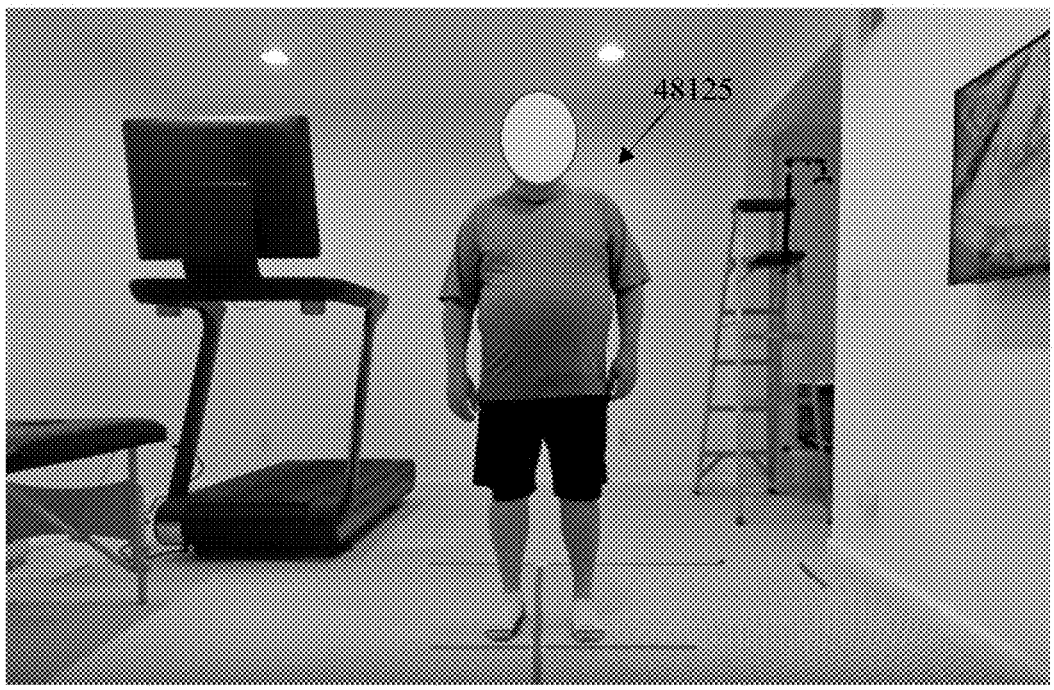
FIGS. 48A-48B illustrate the procedure for a patient performing a hip abduction range of motion measurement test, according to an aspect.
Figure 48B:

FIGS. 48A-48B illustrate the procedure for a patient 48125 performing a hip abduction range of motion measurement test, according to an aspect. Hip abduction is the movement where the leg moves away from the midline of the body, typically performed in a standing or lying position. This movement is essential for assessing the range of motion and the functionality of the hip joint, particularly the muscles and ligaments on the outer thigh and hip.

For the hip abduction range of motion test, the patient 48125 may begin in a standing position with their feet together, or lying on their side with the leg to be tested on top, keeping their body straight. In standing, the weight should be evenly distributed, and in lying, the bottom leg can be slightly bent for stability. From the starting position, the individual lifts their leg outward away from the midline of the body, keeping their knee straight or slightly bent. The movement should be controlled and continue until a comfortable limit is reached without rotating their pelvis or compensating with other body movements.

The keypoints for the hip abduction range of motion measurement test may include the anterior head of the femur and the distal femur between the medial and lateral condyles. The keypoint at the anterior head of the femur serves as the main pivot point near the hip joint, providing a central reference for the initiation and extent of the leg's abduction. The keypoint at the distal femur between the medial and lateral condyles acts as a secondary reference point that moves laterally as the leg abducts. Observing the path and endpoint of this region helps in determining the degree of abduction.

The range of motion for hip abduction is quantified by measuring the angle formed between the abducted leg and a line representing the body's midline. This measurement is done with the individual in a stable, standing position, where one line aligns with the body's midline and the other extends along the thigh, with the pivot over the hip joint. As seen in FIG. 48B, the patient's left hip abduction range of motion is 36 degrees.

Figure 49A:
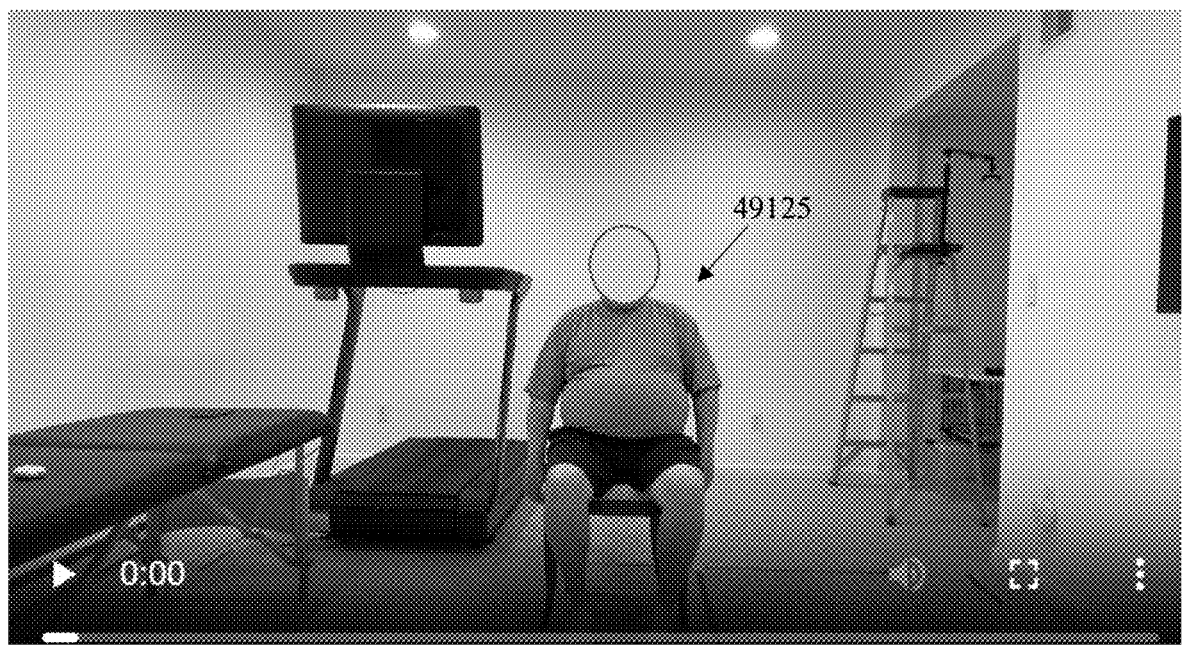
FIGS. 49A-49B illustrate the procedure for a patient performing a hip external rotation range of motion measurement test, according to an aspect.
Figure 49B:
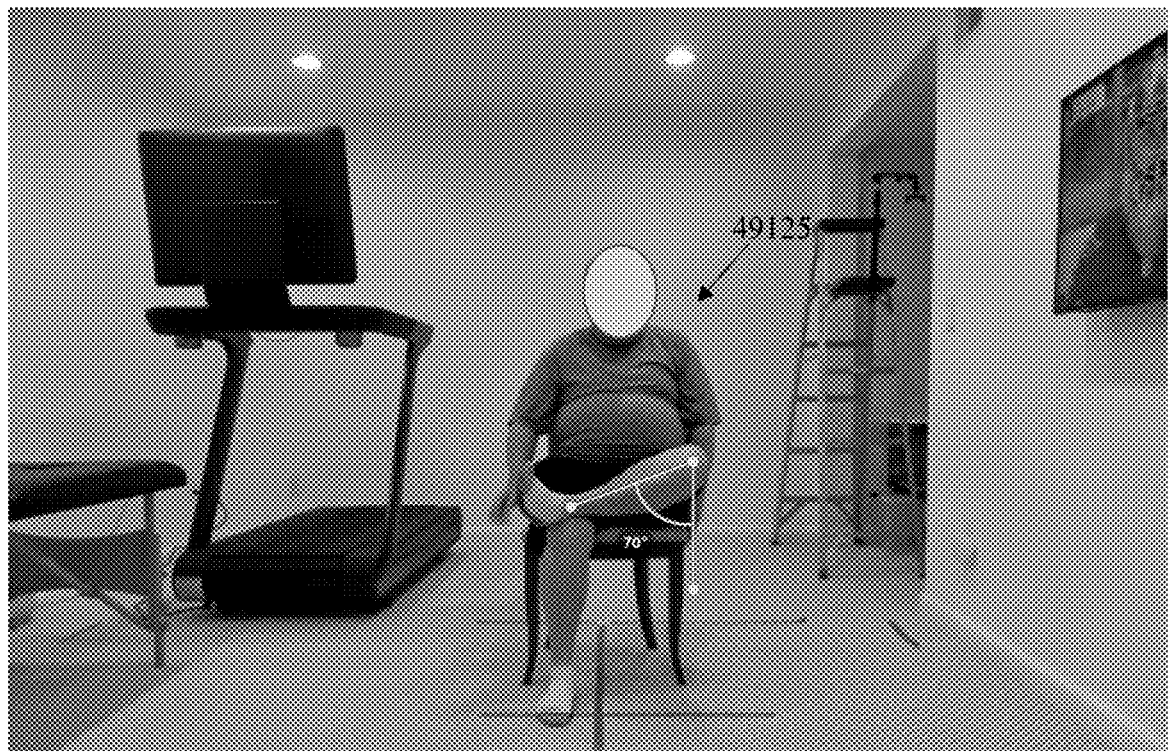

FIGS. 49A-49B illustrate the procedure for a patient 49125 performing a hip external rotation range of motion measurement test, according to an aspect. Hip external rotation involves rotating the thigh outward away from the midline of the body, which is essential for assessing the flexibility and functionality of the hip joint and its surrounding muscles. This movement is particularly significant for activities that require turning or pivoting motions.

For the hip external rotation range of motion test, the patient 49125 may begin seated or lying down with their hip and knee flexed at approximately 90 degrees. This position stabilizes the pelvis and isolates the movement to the hip. From the starting position, the patient 49125 rotates their thigh outward, turning their foot inward while keeping their knee in place. The movement should be performed smoothly and continue until a comfortable limit is reached without straining or involving other parts of the body.

The keypoints for the hip external rotation range of motion measurement test may include the lateral condyle of the tibia and the lateral malleolus. The keypoint at the lateral condyle of the tibia serves as a fixed reference point that helps determine the rotation angle of the tibia, which indirectly reflects hip external rotation. The keypoint at the lateral malleolus (located at the outer ankle) moves as the foot turns inward during the hip's external rotation. Tracking the movement of the lateral malleolus provides clear data on how much the lower leg and foot rotate, offering insights into the hip rotation.

The range of motion for hip external rotation is quantified by measuring the angle of the foot and lower leg. This measurement is done by placing one line aligned with the tibia and the other aligned with the axis of the foot, using the center of the patella as the pivot point with the measurement relative to the neutral starting position. As seen in FIG. 49B, the patient's left hip external rotation range of motion is 70 degrees.

Figure 50A:
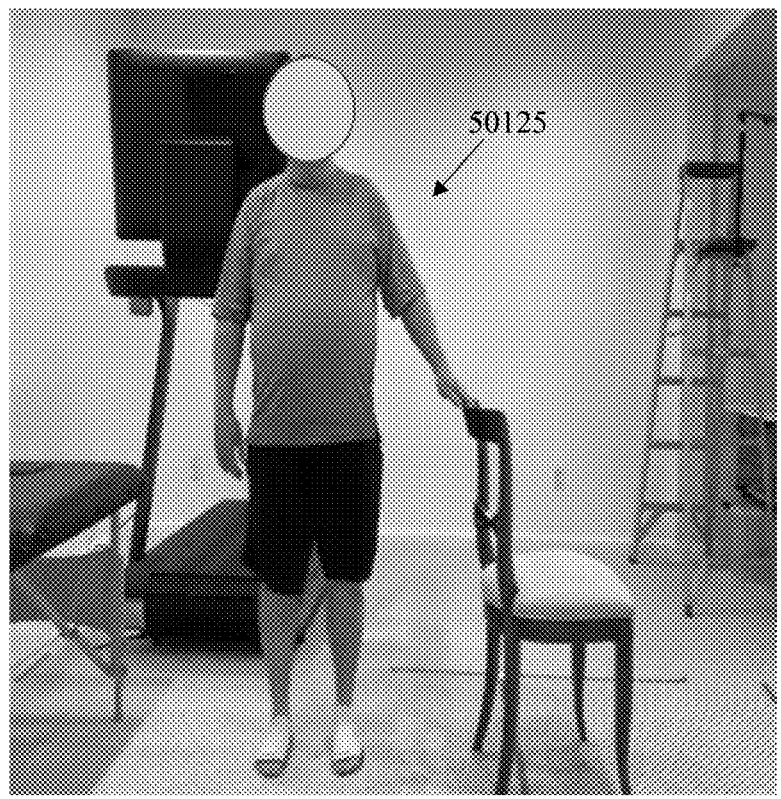
FIGS. 50A-50B illustrate the procedure for a patient performing a hip adduction range of motion measurement test, according to an aspect.
Figure 50B:
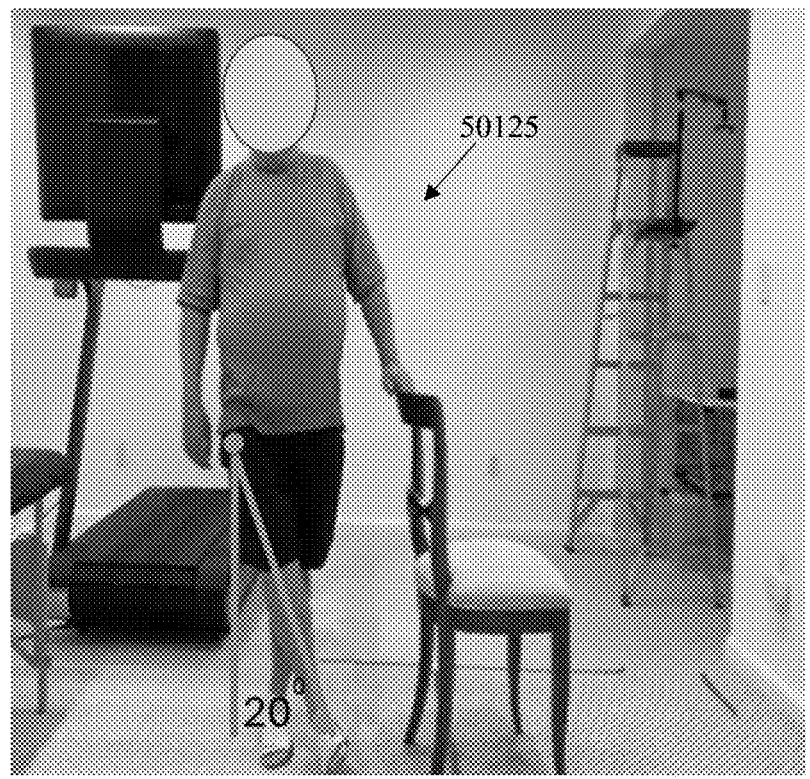

FIGS. 50A-50B illustrate the procedure for a patient 50125 performing a hip adduction range of motion measurement test, according to an aspect. Hip adduction is the movement where the leg is brought towards the midline of the body from an abducted (outward) position, crossing over the standing leg if performed in a standing position. This action is critical for assessing the range of motion and functionality of the muscles on the inner thigh and the stability of the hip joint.

For the hip adduction range of motion test, the patient 50125 may begin in a standing or lying position. In standing, the weight should be shifted to one leg, allowing the other leg to move freely. In a lying position, the individual lies on their side with the leg to be tested on top. From the starting position, the patient 50125 moves the testing leg inward towards the midline of the body. In a standing position, this may involve crossing the leg in front of the standing leg. The movement should be smooth and controlled, ensuring that the pelvis remains stable to isolate the movement to the hip.

The keypoints for the hip adduction range of motion measurement test may include the anterior head of the femur and the distal femur between the medial and lateral condyle. The keypoint at the anterior head of the femur acts as the main pivot point near the hip joint, providing a central reference for the initiation and extent of the leg's adduction. The keypoint at the distal femur between the medial and lateral condyles acts as a secondary reference point that moves towards the midline as the leg adducts. Monitoring the path and endpoint of this area helps in determining the degree of adduction.

The range of motion for hip adduction is quantified by measuring the angle formed between the adducted leg and a line representing the body's midline. This measurement is done with the individual in a stable position, where one line is parallel with the body's midline and the shaft of the femur, and the other with the fulcrum over the hip joint. As seen in FIG. 50B, the patient's right hip adduction rotation range of motion is 20 degrees.

Figure 51A:
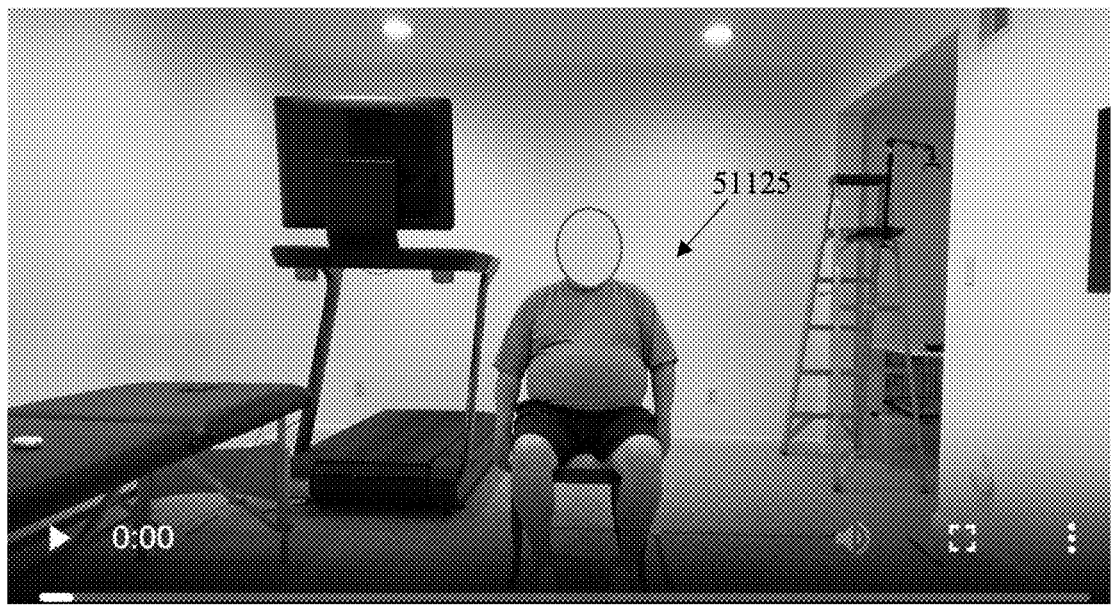
FIGS. 51A-51B illustrate the procedure for a patient performing a hip internal rotation range of motion measurement test, according to an aspect.
Figure 51B:
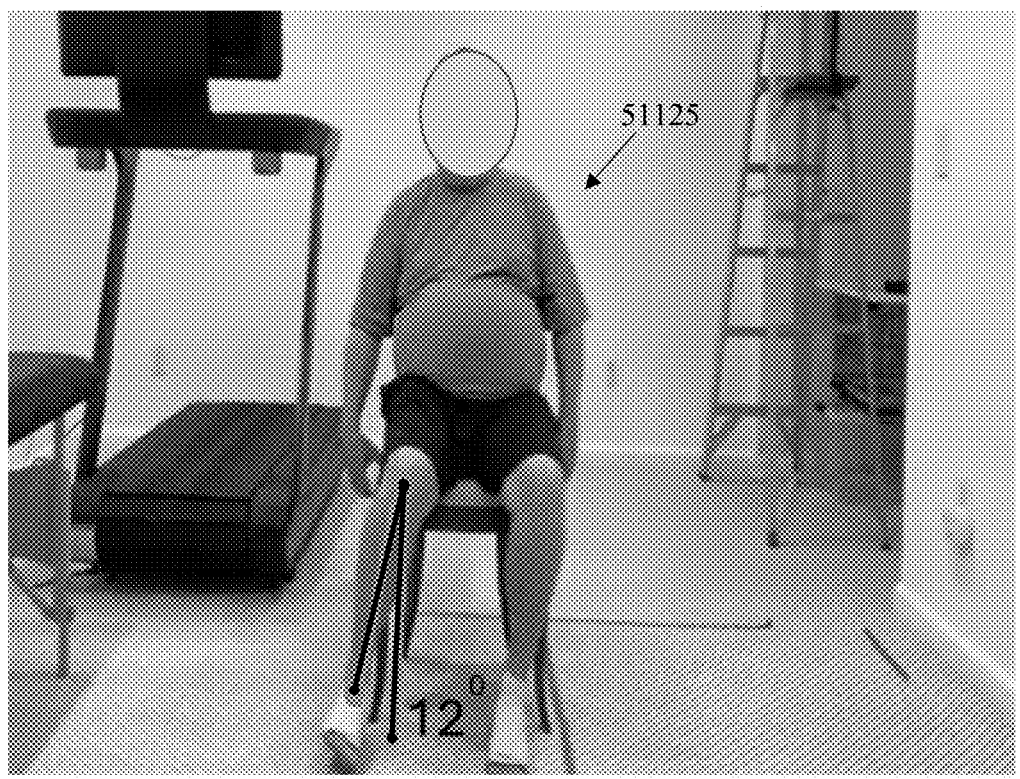

FIGS. 51A-51B illustrate the procedure for a patient 51125 performing a hip internal rotation range of motion measurement test, according to an aspect. Hip internal rotation is the movement where the thigh rotates inward toward the midline of the body, which is essential for assessing the flexibility and functionality of the hip joint and its surrounding muscles. This movement is significant for many functional activities, including walking and turning.

For the hip internal rotation range of motion test, the patient 51125 may begin seated or lying down with their hip and knee flexed at approximately 90 degrees. This position stabilizes the pelvis and isolates the movement to the hip. From the starting position, the patient 51125 rotates their thigh inward, turning their foot outward while keeping their knee in place. The movement should be performed smoothly and continue until a comfortable limit is reached without straining or involving other parts of the body.

The keypoints for the hip internal rotation range of motion measurement test may include the lateral condyle of the tibia and the lateral malleolus. The keypoint at the lateral condyle of the tibia serves as a fixed reference point that helps determine the rotation angle of the tibia, which indirectly reflects hip internal rotation. The keypoint at the lateral malleolus point moves as the foot turns outward during the hip's internal rotation. Tracking the movement of the lateral malleolus provides clear data on how much the lower leg and foot rotate, offering insights into the hip rotation.

The range of motion for hip internal rotation is quantified by measuring the angle of the foot and lower leg relative to a neutral starting position. The measurement is done by placing one line aligned with the tibia and the other with the axis of the foot, using the center of the patella as the pivot point. As seen in FIG. 51B, the patient's right hip internal rotation range of motion is 12 degrees.

Figure 52A:
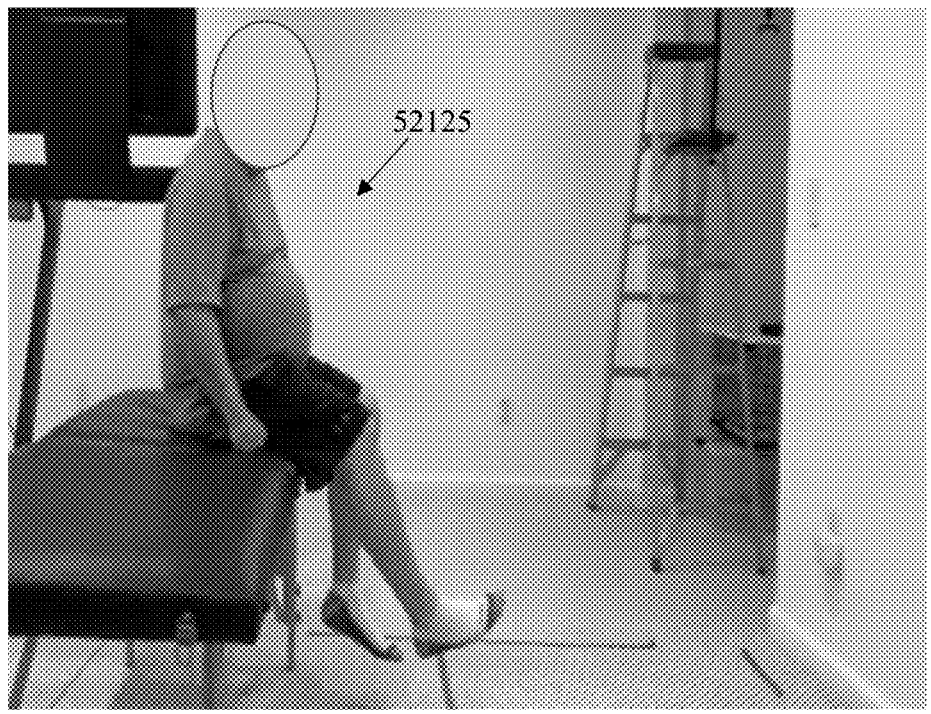
FIGS. 52A-52B illustrate the procedure for a patient performing an ankle dorsiflexion range of motion measurement test, according to an aspect.
Figure 52B:
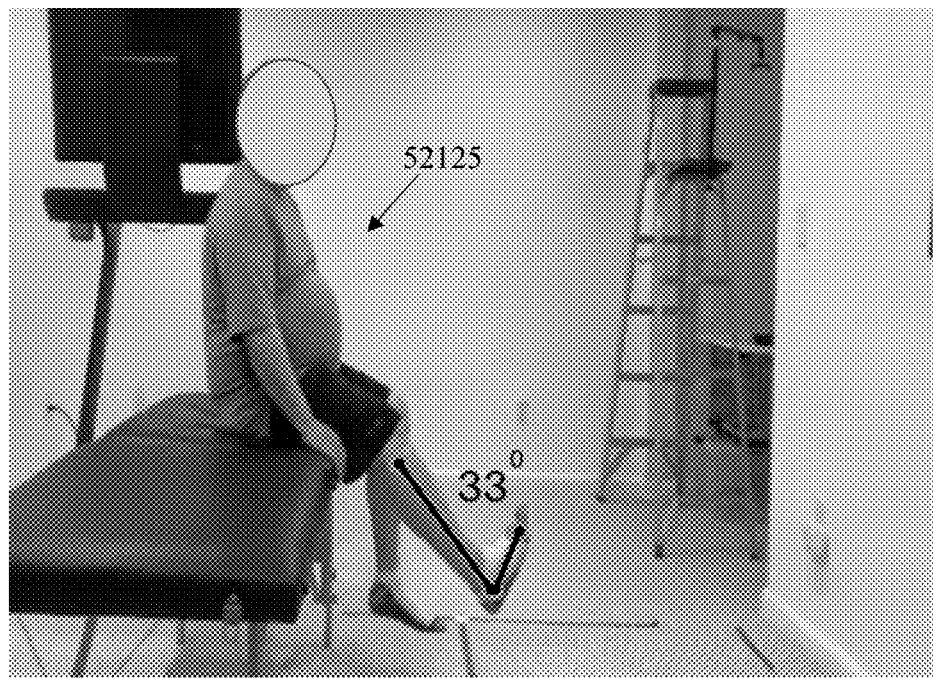

FIGS. 52A-52B illustrate the procedure for a patient 52125 performing an ankle dorsiflexion range of motion measurement test, according to an aspect. Ankle dorsiflexion is the movement where the toes are brought closer to the shin, reducing the angle between the dorsum of the foot and the lower leg. This motion is crucial for assessing the range of motion at the ankle joint, particularly important for gait and various activities requiring foot movement.

For the ankle dorsiflexion range of motion test, the patient 52125 may begin seated with their foot hanging off the edge of a surface or standing with their foot flat on the ground. Their knee can be either bent or straight, depending on the specific assessment requirements. From the starting position, the patient 52125 flexes their ankle by pulling their toes upward toward their shin. Their heel should remain on the ground or the surface if seated, ensuring the movement isolates at the ankle.

The keypoints for the ankle dorsiflexion range of motion measurement test may include the lateral condyle of the fibula, the lateral malleolus, the ankle and a line parallel to the $5^{th}$ metatarsal. The keypoint at the lateral condyle of the fibula (near the top of the fibula near the knee) acts as a reference point for the upper part of the lateral aspect of the lower leg. The keypoint at the lateral malleolus provides a clear marker for the movement of the ankle joint as it participates directly in the dorsiflexion. The keypoint at the ankle (specifically referring to the joint area) is where the actual movement of dorsiflexion occurs and can be monitored for movement extent. The line parallel to the 5$^{th}$ metatarsal helps assess the alignment and movement of the foot relative to the lower leg, ensuring that the measurement tracks the true dorsiflexion motion without lateral deviation.

The range of motion for ankle dorsiflexion is quantified by measuring the angle formed between the lower leg and the foot. This is done by a line that is aligned with the lateral aspect of the fibula (or parallel to the tibia), and the other aligning with a line parallel to the 5th metatarsal, pivoting at the ankle joint. As seen in FIG. 52B, the patient's right ankle dorsiflexion range of motion is 33 degrees.

Figure 53A:
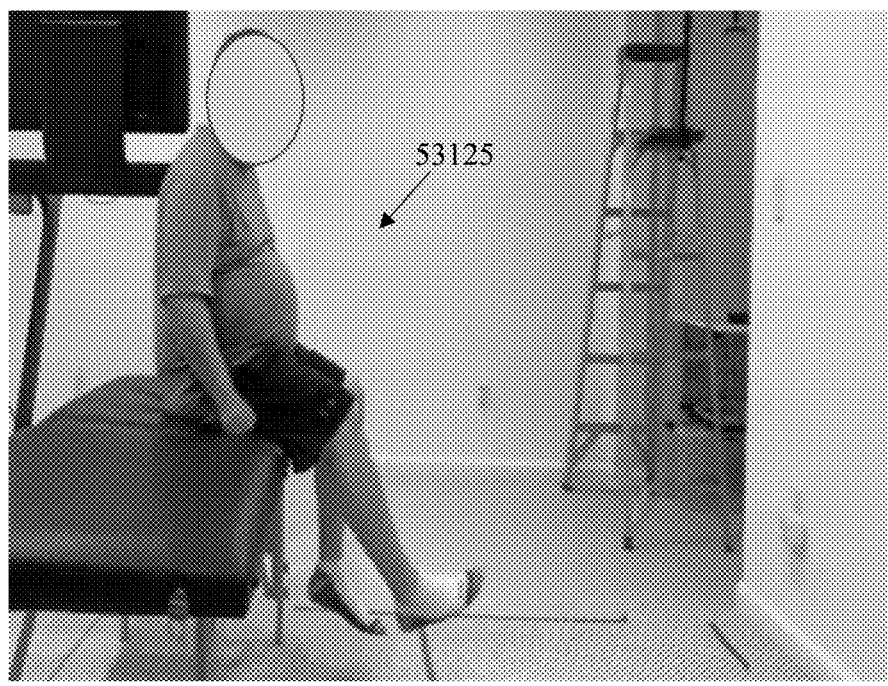
FIGS. 53A-53B illustrate the procedure for a patient performing an ankle plantarflexion range of motion measurement test, according to an aspect.
Figure 53B:
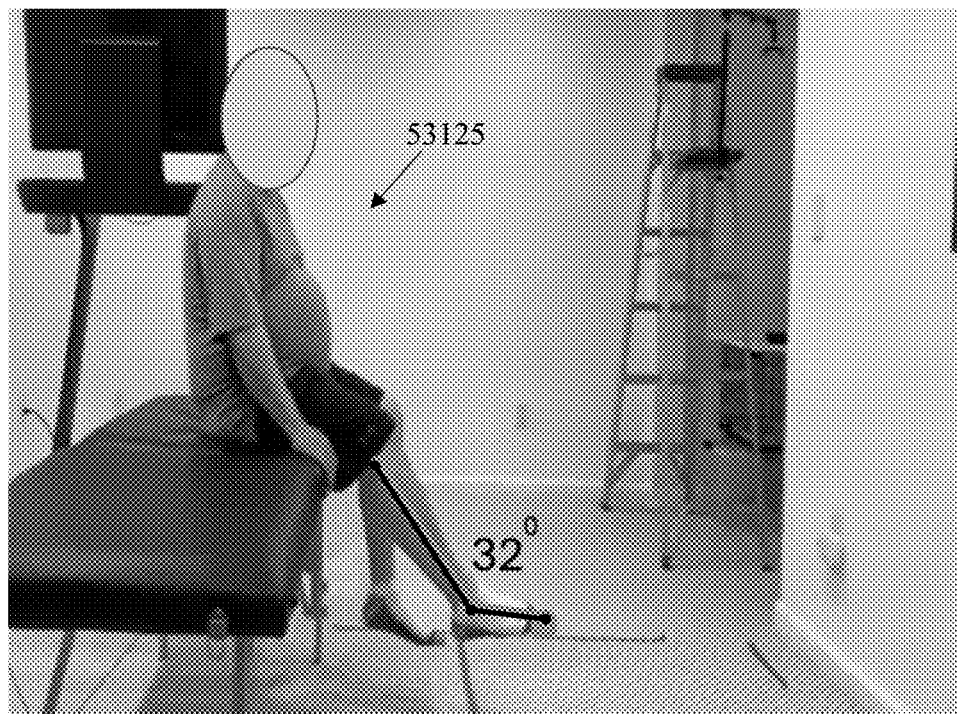

FIGS. 53A-53B illustrate the procedure for a patient 53125 performing an ankle plantarflexion range of motion measurement test, according to an aspect. Ankle plantarflexion is the movement where the toes point downward away from the shin, increasing the angle between the foot and the lower leg. This motion is essential for evaluating the functionality and range of motion of the ankle joint, particularly important for actions like pushing off during walking or running.

For the ankle plantarflexion range of motion test, the patient 53125 may begin seated with their foot hanging off the edge of a surface or standing with their foot flat on the ground. Their knee can be either bent or straight, depending on the specific assessment requirements. From the starting position, the patient 53125 extends their ankle by pointing their toes downward, moving away from their shin. The movement should be smooth and controlled, focusing on isolating the movement at the ankle.

The keypoints for the ankle plantarflexion range of motion measurement test may include the lateral condyle of the fibula, the lateral malleolus, the ankle and a line parallel to the 5$^{th}$ metatarsal. The keypoint at the lateral condyle of the fibula acts as a reference point for the upper part of the lateral aspect of the lower leg. The keypoint at the lateral malleolus serves as a clear marker for the movement of the ankle joint during plantarflexion. The keypoint at the ankle is a point central to observing the movement of plantarflexion and monitoring its extent. The line parallel to the 5$^{th}$ metatarsal helps in assessing the alignment and movement of the foot relative to the lower leg, ensuring the measurement accurately tracks the motion of plantarflexion without lateral deviation.

The range of motion for ankle plantarflexion is quantified by measuring the angle between the lower leg and the foot as the foot points downward. This is measured by creating a line that aligns with the lateral aspect of the fibula (or parallel to the tibia), and the other aligning with a line parallel to the 5th metatarsal, pivoting at the ankle joint. As seen in FIG. 52B, the patient's right ankle plantarflexion range of motion is 32 degrees.

Figure 54A:
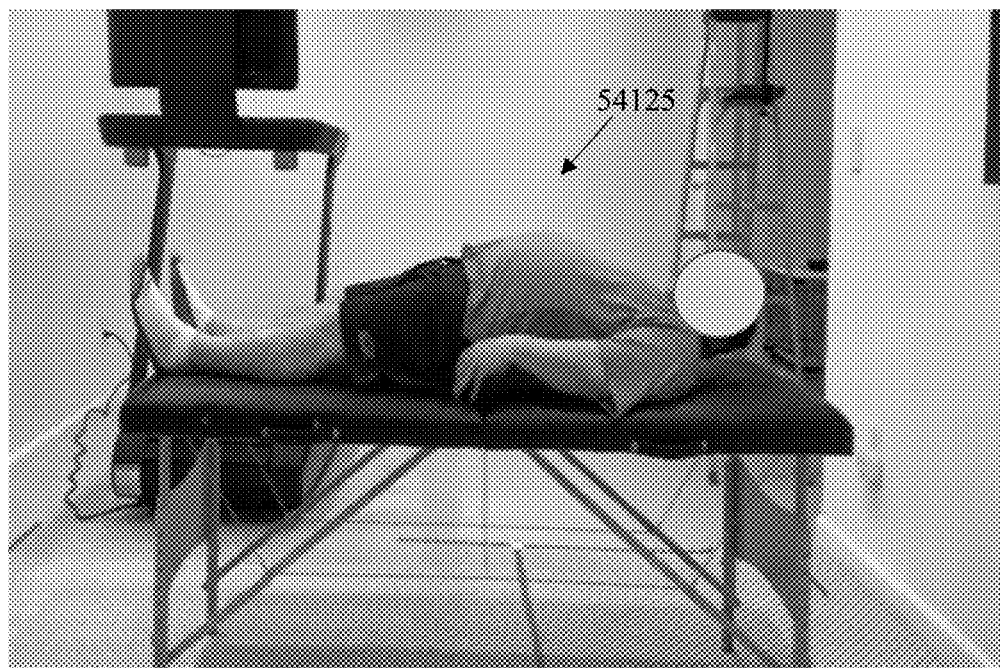
FIGS. 54A-54B illustrate the procedure for a patient performing a knee flexion range of motion measurement test, according to an aspect.
Figure 54B:
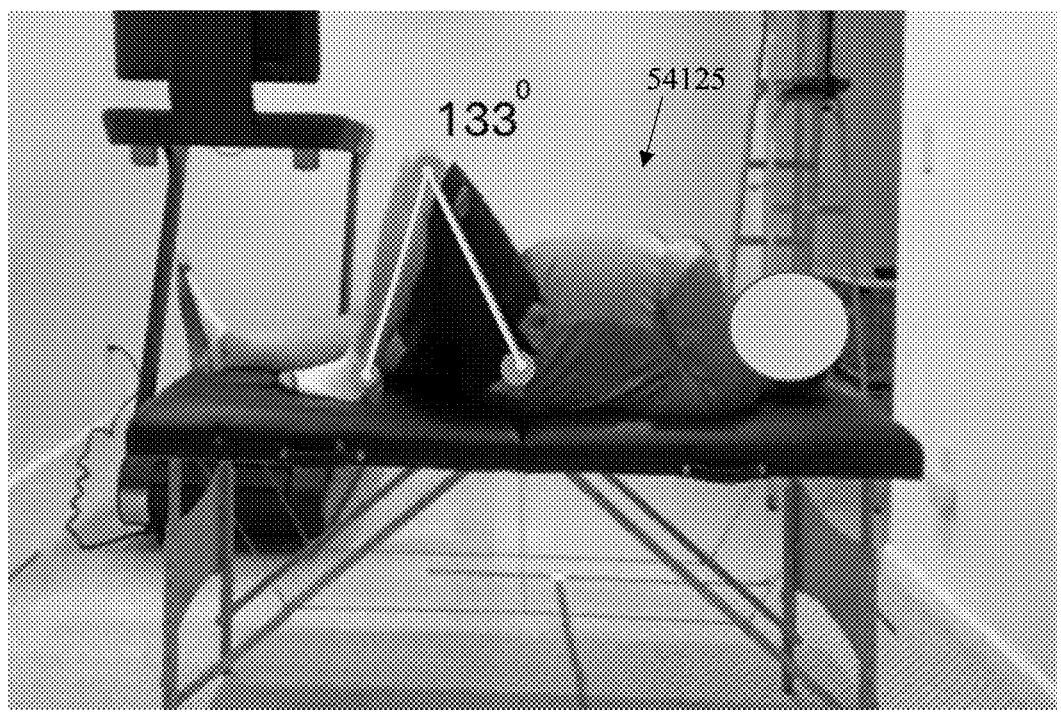

FIGS. 54A-54B illustrate the procedure for a patient 54125 performing a knee flexion range of motion measurement test, according to an aspect. Knee flexion is the movement where the lower leg bends towards the thigh, decreasing the angle at the knee joint. This action is crucial for assessing the functionality and range of motion of the knee joint, vital for activities such as walking, running, sitting, and climbing stairs.

For the knee flexion range of motion test, the patient 54125 may begin either seated or lying down, with the knee in an extended (straight) position. This initial position helps isolate the knee joint for accurate measurement and ensures the alignment of the hip and ankle. From the extended position, the individual flexes their corresponding knee by bending their lower leg towards their thigh. The movement should be smooth and controlled, with the focus on isolating the movement at the knee to prevent any compensatory movements from the hip or ankle.

The keypoints for the knee flexion range of motion measurement test may include the head of the hip (Grater Trochanter), the lateral condyle of the corresponding femur, and the lateral epicondyle of the ankle. The keypoint at the head of the hip serves as the proximal reference point at the hip, providing a stable base from which the movement of the knee can be measured. This keypoint at the head of the hip remains stationary, ensuring the alignment of the femur during knee flexion. The keypoint at the lateral condyle of the femur, which is a bony prominence located near the knee, acts as a pivot point for knee flexion, providing a central marker for the extent of movement at the knee. The keypoint at the lateral epicondyle of the ankle moves towards the buttock as the knee flexes, tracing the path of the lower leg as it bends.

The range of motion for knee flexion is quantified by measuring the angle formed between the corresponding thigh and lower leg at the point of maximum flexion. This is measured by creating a line along the thigh (following the line from the head of the hip to the lateral condyle of the femur), and another that extends along the lower leg. As seen in FIG. 54B, the patient's left knee flexion range of motion is 133 degrees.

Figure 55A:
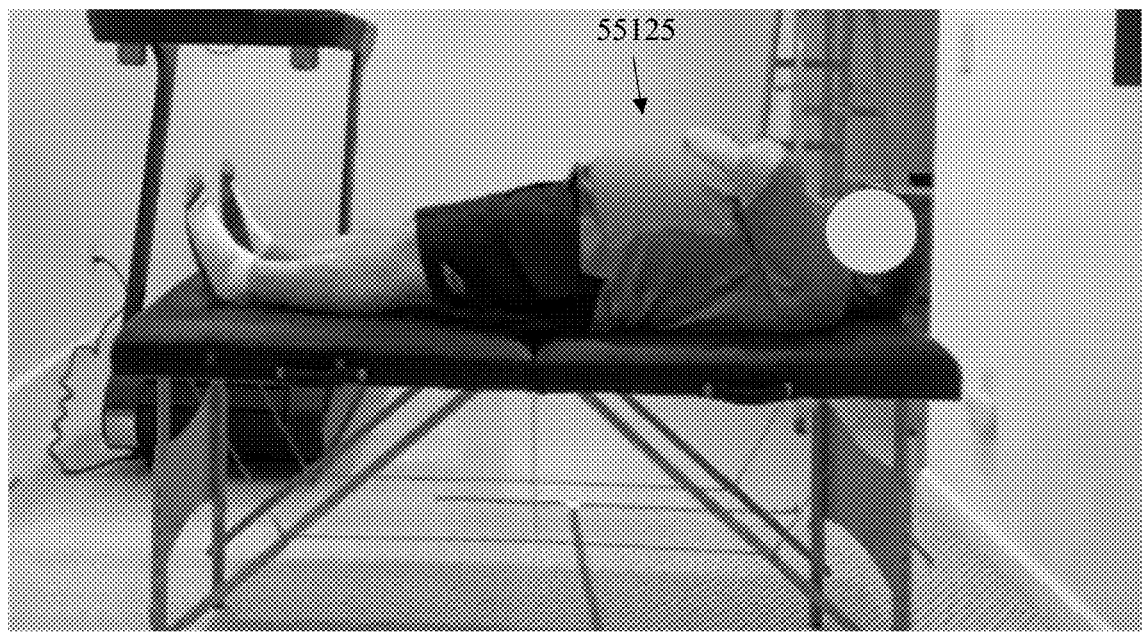
FIGS. 55A-55B illustrate the procedure for a patient performing a knee extension range of motion measurement test, according to an aspect.
Figure 55B:
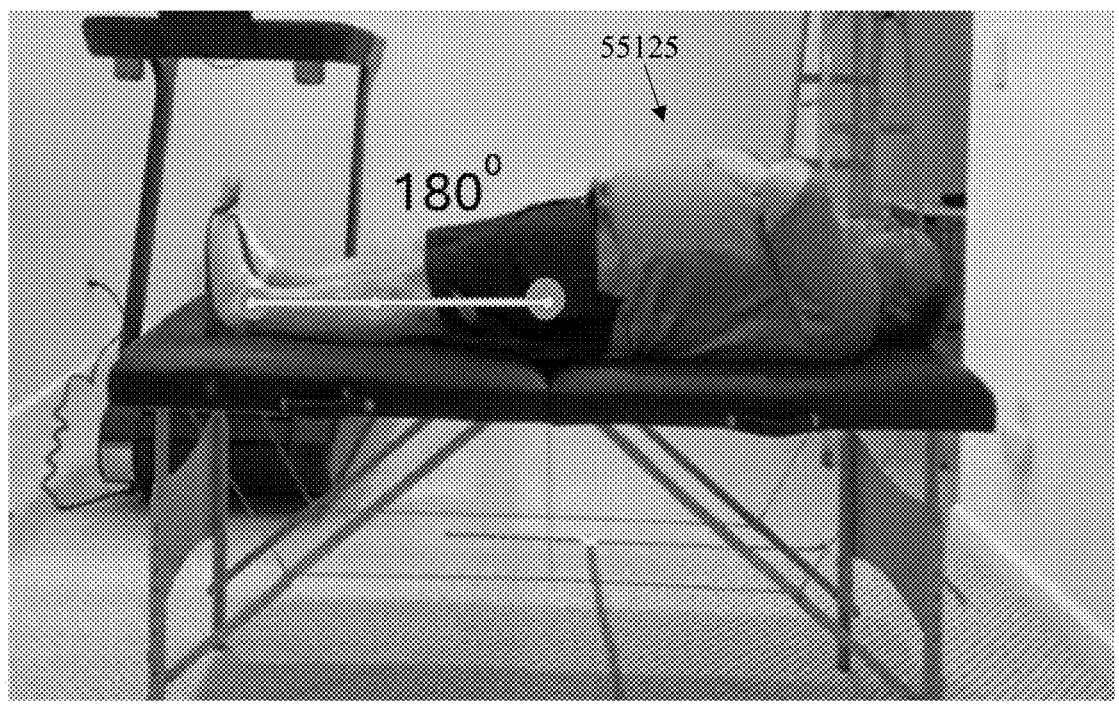

FIGS. 55A-55B illustrate the procedure for a patient 55125 performing a knee extension range of motion measurement test, according to an aspect. Knee extension is the movement where the lower leg straightens out from the bent position, aligning with the thigh and increasing the angle at the knee joint. This movement is critical for evaluating the functionality and range of motion of the knee joint, which is essential for walking, running, and standing activities.

For the knee extension range of motion test, the patient 55125 may begin either seated or lying down with the corresponding knee in a flexed (bent) position. This position isolates the knee for precise measurement and ensures that the hip and ankle remain aligned without additional stress. From the flexed position, the individual extends the knee by straightening the leg. The movement should be smooth and controlled, focusing on isolating the movement to the knee to avoid any compensatory movements from the hip or ankle.

The keypoints for the knee extension range of motion measurement test may include the head of the hip, the lateral condyle of the corresponding femur and the lateral epicondyle of the ankle. The keypoint at the head of the hip serves as the proximal reference point at the hip, providing a stable base from which the movement of the knee can be measured. It remains stationary and helps to ensure the alignment of the femur during knee extension. The keypoint at the lateral condyle of the femur serves as a pivot point for knee extension, providing a central marker for the extent of movement at the knee. The keypoint at the lateral epicondyle of the ankle moves as the knee extends, providing a distal reference that helps track the alignment and endpoint of the lower leg as it straightens.

The range of motion for knee extension is quantified by measuring the angle formed between the thigh and the lower leg at the point of maximum extension. This measurement is created by using one line that aligns with the thigh (following the line from the head of the hip to the lateral condyle of the femur), and the other extending along the lower leg (following the line from the lateral condyle of the femur to the lateral epicondyle of the ankle), with the fulcrum located at the lateral condyle of the femur. As seen in FIG. 55B, the patient's left knee extension range of motion is 180 degrees.

The disclosed range of motion tests described in FIGS. 46A-55B may be classified as legs/lower extremities range of motion tests for simplicity. These leg/lower extremity range of motion tests may be performed as part of a leg/lower extremity assessment, similarly to the hereinabove described gait assessment. Furthermore, by performing this described lower extremity assessment, the MMH system may be configured to generate a lower extremity diagnosis by evaluating the resultant range of motion values to assess and suitably report a patient's MSK health within their lower extremities region.

Figure 56A:
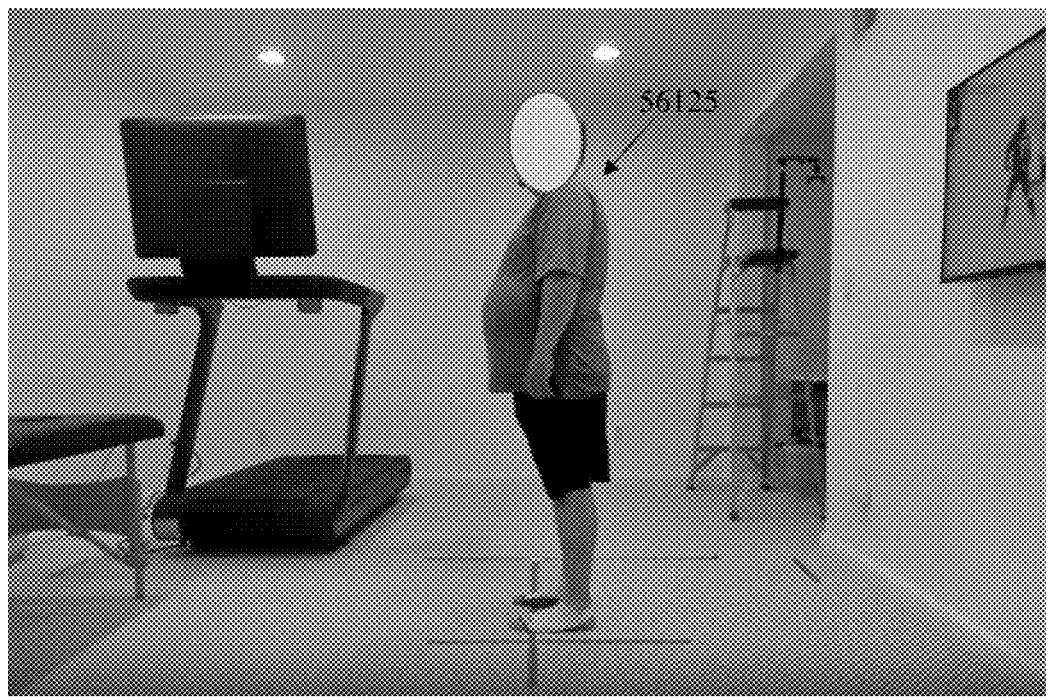
FIGS. 56A-56B illustrate the procedure for a patient performing a cervical extension range of motion measurement test, according to an aspect.
Figure 56B:
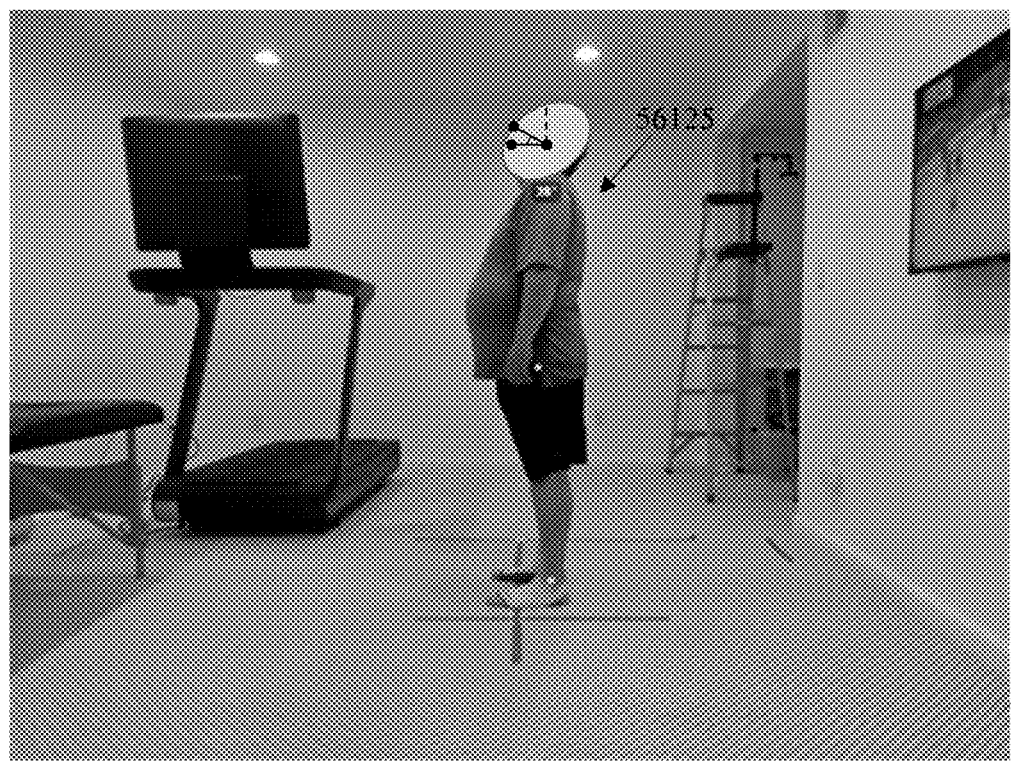

FIGS. 56A-56B illustrate the procedure for a patient 56125 performing a cervical extension range of motion measurement test, according to an aspect. Cervical extension is the movement of tilting the head backward, which opens up the angle between the neck and the jawline. It is crucial for assessing the range of motion and health of the cervical spine.

For the cervical extension range of motion test, the patient 56125 may begin in a neutral, upright head position with their eyes looking forward. In this position, the tip of their nose and the center of their chin are aligned vertically over their chest, and their ears are aligned with their shoulders. The patient 56125 then gradually tilts their head backward. This movement involves lifting their face upward while the back of their head moves downward, akin to looking up at the ceiling.

The keypoints for the cervical extension range of motion measurement test may include the tip of the nose, the center of the anterior aspect of the chin and the external auditory meatus (ear). The keypoint at the tip of the nose moves upward, describing a backward arc, as the head extends back. The keypoint at the center of the anterior aspect of the chin moves upward and slightly forward during the test, providing a clear indicator of the degree of extension. The keypoint at the external auditory meatus moves in a small arc backward. The path and angle change relative to a neutral starting position can be measured to quantify the extension.

For cervical extension, measure the angle formed between a line that goes from the external auditory meatus of the ear to the tip of the nose in the neutral position and a new line formed after full extension with the external auditory meatus as the fulcrum. As seen in FIG. 56B, the patient's cervical extension range of motion is 28 degrees.

Figure 57A:
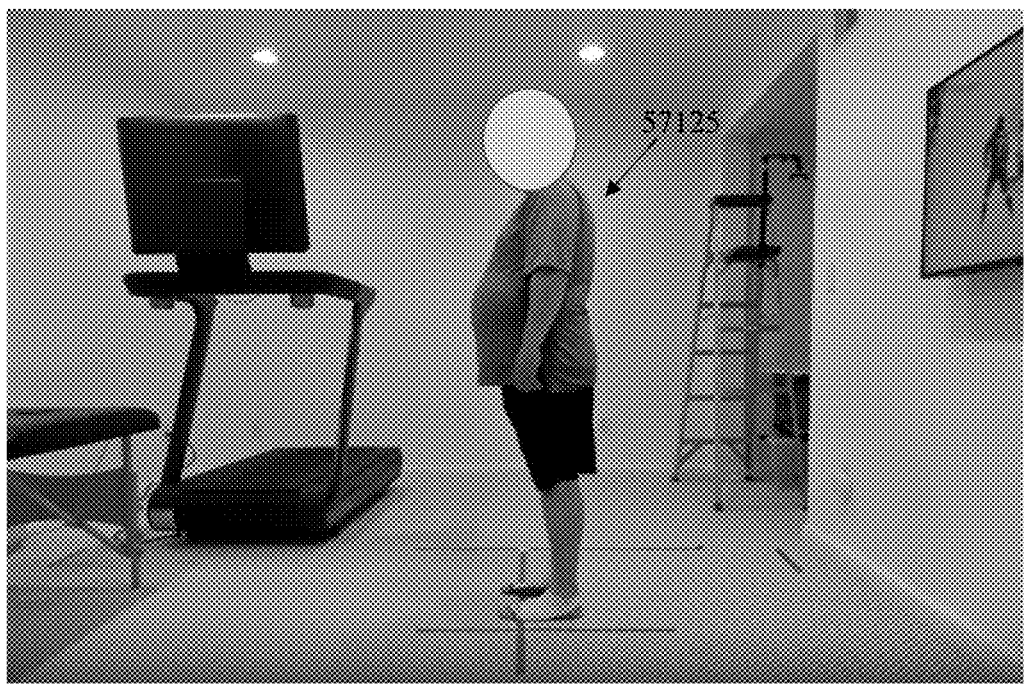
FIGS. 57A-57B illustrate the procedure for a patient performing a cervical flexion range of motion measurement test, according to an aspect.
Figure 57B:
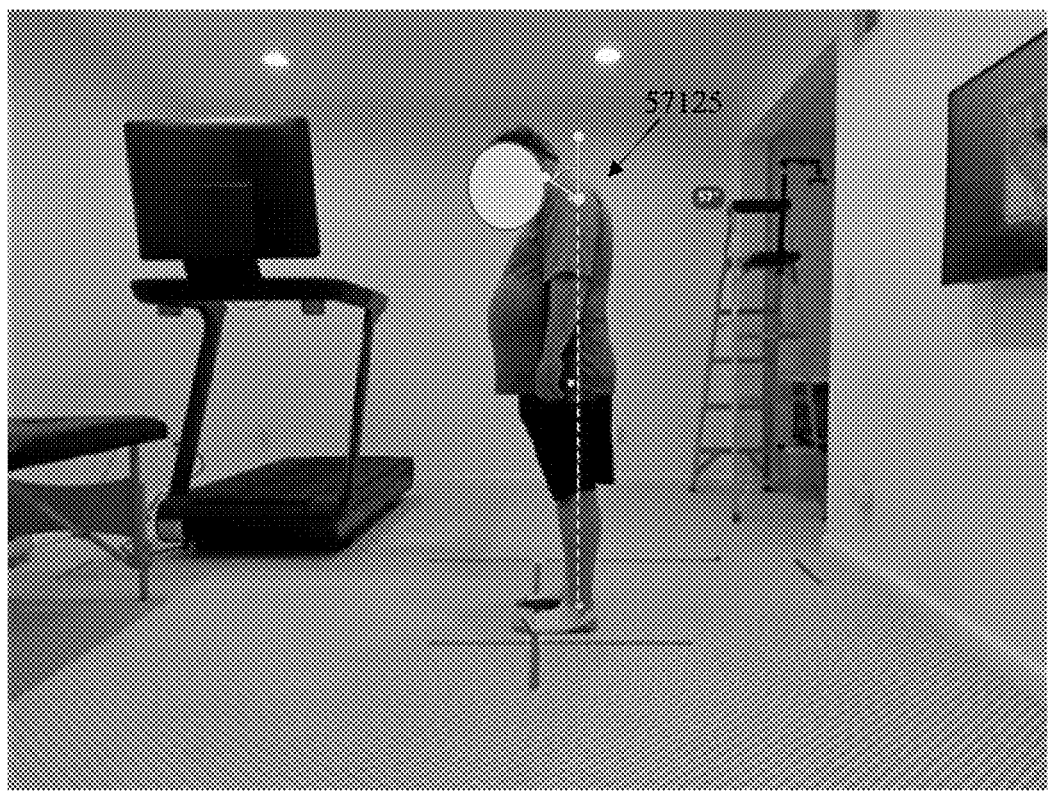

FIGS. 57A-57B illustrate the procedure for a patient 57125 performing a cervical flexion range of motion measurement test, according to an aspect. Cervical flexion involves the forward bending motion of the head, reducing the angle between the chin and the chest. This movement is essential for evaluating the neck's range of motion and overall spinal health.

For the cervical flexion range of motion test, the patient 57125 may begin with their head in a neutral position, eyes looking straight ahead. Their ears are ideally aligned with the shoulders, and their spine is in an upright posture. The patient 57125 flexes their neck by moving their chin downward towards their chest. This motion is carried out smoothly without straining, aiming to touch the chin to their chest or moving as close as comfortably possible.

The keypoints for the cervical flexion range of motion measurement test may include the shoulder point and the external auditory meatus. The keypoint at the shoulder point remains stationary and serves as a fixed reference point. This keypoint is crucial because it provides a baseline from which the movement of the ear can be measured. The keypoint at the external auditory meatus moves downward and forward relative to its starting position, as the head flexes forward.

For cervical flexion, measurements may be taken for the angle formed between a line that goes from the external auditory meatus of the ear to the tip of the nose in the neutral position and a new line formed after full extension with the external auditory meatus as the fulcrum. As seen in FIG. 57B, the patient's cervical flexion range of motion is 57 degrees.

Figure 58A:
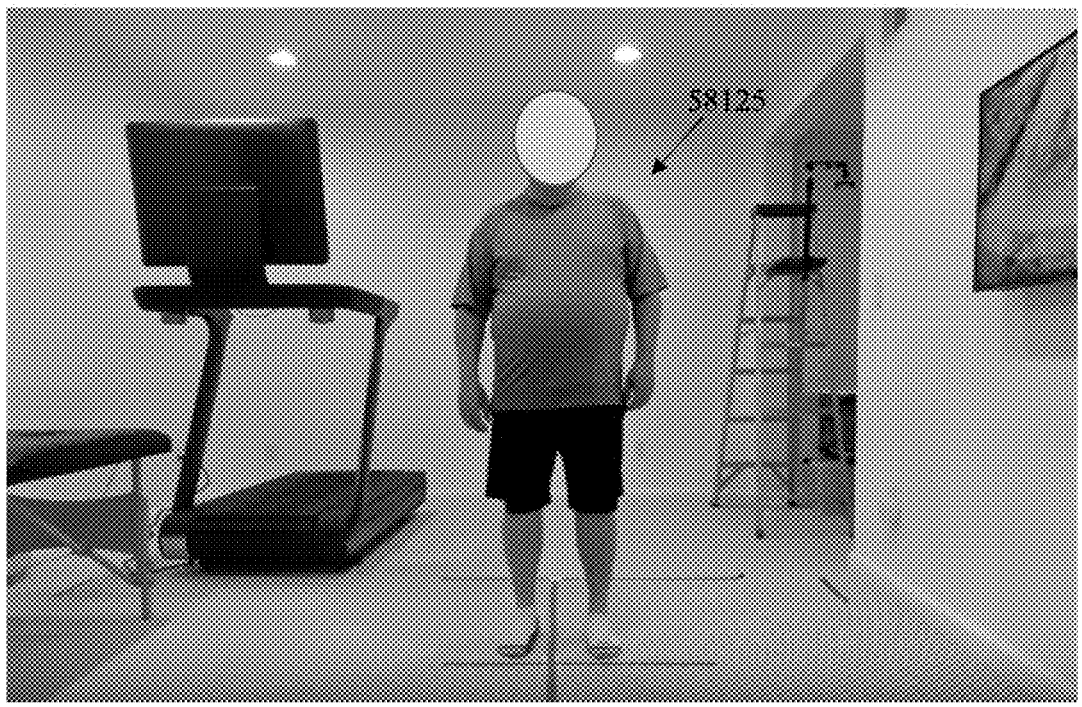
FIGS. 58A-58B illustrate the procedure for a patient performing a cervical rotation range of motion measurement test, according to an aspect.
Figure 58B:
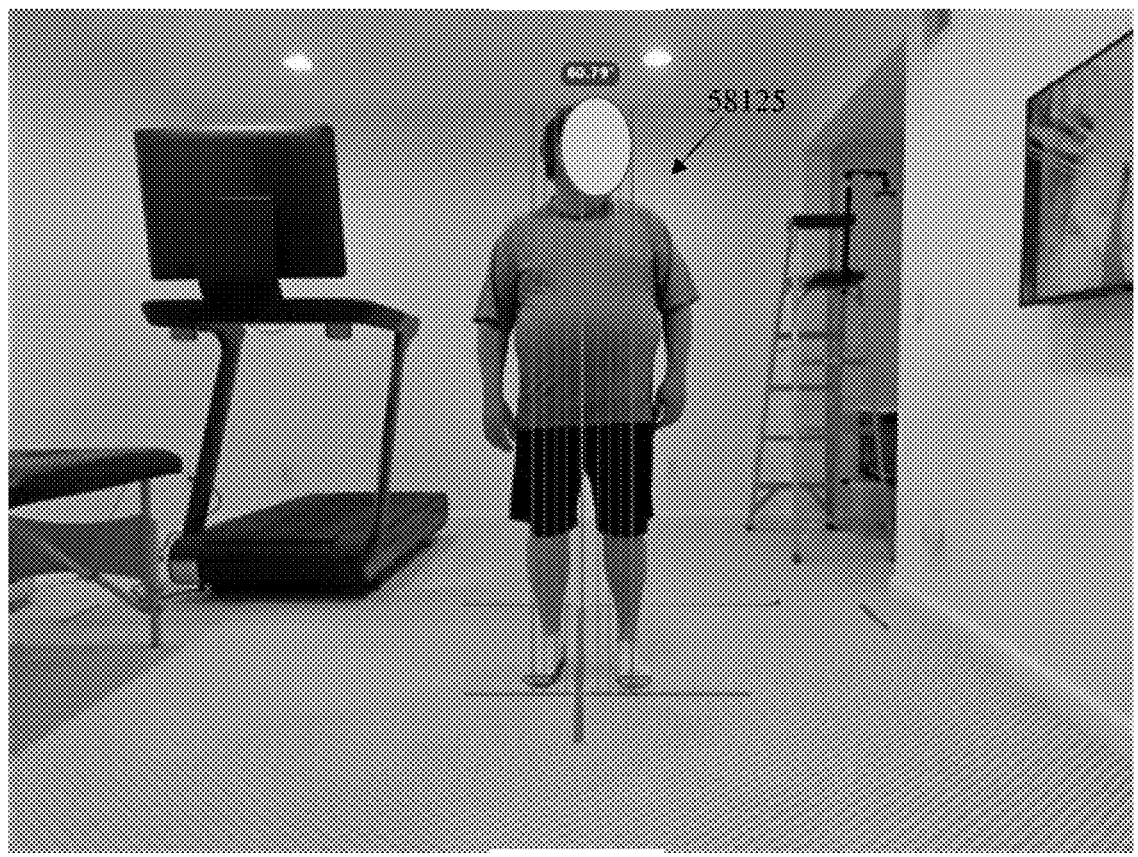

FIGS. 58A-58B illustrate the procedure for a patient 58125 performing a cervical rotation range of motion measurement test, according to an aspect. Cervical rotation involves the rotational movement of the head around the vertical axis of the spine, which is crucial for assessing the neck's range of motion and flexibility.

For the cervical rotation range of motion test, the patient 58125 may begin with their head in a neutral position, facing forward. The tip of their nose is aligned with the midline of their body, and their ears are level and perpendicular to their midline. Next, the patient 58125 rotates their head to one side, either left or right, aiming to align their chin as far over their corresponding shoulder as comfortably possible without moving their shoulders.

The keypoints for the cervical rotation range of motion measurement test may include the tip of the nose and the ear (relative to the midline). The keypoint at the tip of the nose moves horizontally away from the midline of the body as the head rotates. The keypoint at the ear (relative to the midline) allows for observation of how far the ear on the side of the rotation moves away from the midline, which can help gauge the extent of cervical rotation. In contrast, the ear on the opposite side moves toward the midline, such that said other ear can be used as an additional measurement point.

The range of motion for cervical rotation can be quantified by measuring the angle or the horizontal distance of the tip of the nose as it moves relative to the midline from its neutral to its rotated position. As seen in FIG. 58B, the patient's left cervical rotation range of motion is 60.79 degrees.

Figure 59A:
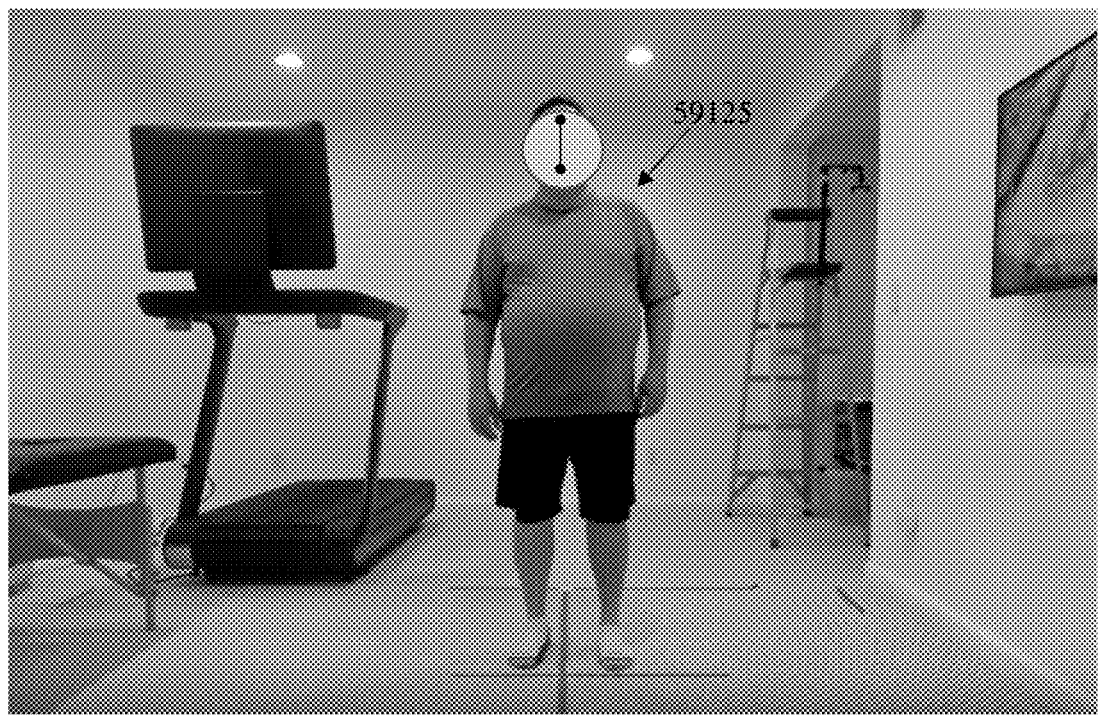
FIGS. 59A-59B illustrate the procedure for a patient performing a cervical lateral bending range of motion measurement test, according to an aspect.
Figure 59B:

FIGS. 59A-59B illustrate the procedure for a patient 59125 performing a cervical lateral bending range of motion measurement test, according to an aspect. Cervical lateral bending, also known as lateral flexion, is the movement where the head tilts to the side, reducing the space between the ear and the shoulder on that side. This movement is vital for assessing the flexibility and range of motion of the neck's lateral musculature and vertebral joints.

For the cervical lateral bending range of motion test, the patient 59125 may begin with their head in a neutral, upright position, facing forward, wherein the tip of their nose is aligned with the midline of their body, and their ears are level, perpendicular to their midline. Next, The patient 59125 bends their head to one side (either left or right), trying to bring their ear closer to the shoulder on the same side. This movement should be performed without elevating the shoulder or tilting the head forward or backward.

The keypoints for the cervical lateral bending range of motion measurement test may include the tip of the nose and the distance from the midline. The keypoint at the tip of the nose moves laterally away from the midline as their head tilts to the side. This lateral movement of the nose from its central position to its maximum deviation provides a measure of the degree of lateral bending. The distance from the midline (the horizontal distance from the tip of the nose to the midline changes as their head bends. This distance increases on the side towards which the head bends and decreases on the opposite side.

The range of motion for cervical lateral bending is quantified by measuring the lateral distance from the tip of the nose as it moves from the midline neutral position to the fully rotated position. As seen in FIG. 59B, the patient's left cervical lateral bending range of motion is 26 degrees. The disclosed range of motion tests described in FIGS. 56A-59B may be classified as neck range of motion tests, for simplicity. These neck range of motion tests/biomechanical movements may be performed as part of a neck assessment, similarly to the hereinabove described gait assessment. Furthermore, by performing this described neck assessment, the MMH system may be configured to generate a neck diagnosis by evaluating the resultant range of motion values to assess and suitably report a patient's MSK health within their neck region.

As described hereinabove, the disclosed AI bot of the MMH system may be configured to instruct/guide patients through ROM tests of a corresponding assessment in order to collect information needed to generate a diagnosis of a patient's MSK health for a corresponding region. In an embodiment, the MMH/computer system may be configured to conduct alternative assessments of patient's health such as cardiovascular health, neurologic health, dermatologic health, etc. Again, this corresponding computer system may have the same/similar architecture as the hereinabove described computer system utilized for gait assessment, including having a main portal, and AI bot, a patient portal, a central database, etc. Furthermore, for each assessment, the computer system may be configured to capture a corresponding video, analyze each frame for keypoints, and track and compare keypoint positions to determine relevant measurements and angles in the calculation of a patient's range of motion for said assessment.

It should be understood that for each stretch/measurement test described hereinabove, the referenced keypoints may be located on the corresponding limb/body part on a side of the body being assessed. For example for a left shoulder flexion range of motion measurement test, the keypoints may be the lateral shoulder point for the left shoulder, the olecranon of the left elbow and a vertical line perpendicular to the ground. Some range of motion measurement tests measuring a corresponding side movement may result in body parts on that same side being hidden from the camera, such as the cervical rotation range of motion measurement test of FIG. 58A-58B. In said tests, a keypoint mentioned, such as the keypoint at the ear, may be placed at the right ear for the left cervical rotation range of motion measurement test, as the left ear may be obscured by the rotation of the patient's head/neck, and this may be difficult to track accurately.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to.

Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

Claim limitations should be construed as means-plus-function limitations only if the claim recites the term "means" in association with a recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

What is claimed is:

1. A computer system for automatically performing medical diagnoses comprising:
   a main portal configured to allow data communication with a user device, thus allowing a user to access the computer system;
   an Artificial Intelligence (AI) bot in data communication with the main portal, the AI bot being configured to guide the user through a back assessment including a series of intake questions and machine-learned biomechanical movements, perform the back assessment and diagnose a patient, wherein the AI bot is further configured to receive video data of the patient performing the biomechanical movements, separate the video data into individual frames, and analyze each individual frame of the video using a custom trained model to identify coordinates of keypoints to generate a back diagnosis for the patient;
   a patient portal in data communication with a processing and communication module, and the AI bot, the patient portal being configured to allow the patient to access the back diagnosis; and
   a central database in data communication with the processing and communication module, an internal database, the AI bot and the patient portal, the central database being configured to facilitate an interconnection of the AI bot with the internal database,
   wherein the central database is configured to access an external database;
   wherein the internal database is configured to store data utilized by the AI bot to guide the user through the back assessment, perform the back assessment and diagnose the patient.

2. The back assessment of claim 1 comprising a trunk extension range of motion measurement test, wherein the keypoints comprise a lateral condyle of a corresponding femur, a lateral head of the corresponding femur and a mid axillary line toward the head of the corresponding humerus.

3. The computer system of claim 1, wherein the internal database comprises an EMMA bot storage database, an EMMA AI/ML storage database, a clinical management storage database and a risk value database.

4. The computer system of claim 1, wherein the external database comprises a managing and scheduling database, a medical records database and an IoMT database.

5. The computer system of claim 1, wherein the central database is configured to organize and temporarily store data being transferred between the corresponding databases that it is in data communication with.

* * * * *